(12) United States Patent
Kariko et al.

(10) Patent No.: US 10,232,055 B2
(45) Date of Patent: *Mar. 19, 2019

(54) RNA CONTAINING MODIFIED NUCLEOSIDES AND METHODS OF USE THEREOF

(71) Applicant: The Trustees of the University of Pennsylvania, Philadelphia, PA (US)

(72) Inventors: Katalin Kariko, Rydal, PA (US); Drew Weissman, Wynnewood, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/339,363

(22) Filed: Oct. 31, 2016

(65) Prior Publication Data

US 2017/0043037 A1  Feb. 16, 2017

Related U.S. Application Data

(63) Continuation of application No. 14/456,302, filed on Aug. 11, 2014, now Pat. No. 9,750,824, which is a continuation of application No. 13/839,023, filed on Mar. 15, 2013, now Pat. No. 8,835,108, which is a continuation of application No. 13/585,517, filed on Aug. 14, 2012, now Pat. No. 8,691,966, which is a continuation of application No. 11/990,646, filed as application No. PCT/US2006/032372 on Aug. 21, 2006, now Pat. No. 8,278,036.

(60) Provisional application No. 60/710,164, filed on Aug. 23, 2005.

(51) Int. Cl.
| | |
|---|---|
| C07H 21/04 | (2006.01) |
| A61K 48/00 | (2006.01) |
| C07K 14/47 | (2006.01) |
| C07K 14/505 | (2006.01) |
| C12N 15/117 | (2010.01) |
| C12N 15/67 | (2006.01) |
| C07H 21/02 | (2006.01) |
| C12Q 1/68 | (2018.01) |
| C12N 15/85 | (2006.01) |
| A61K 38/17 | (2006.01) |
| A61K 38/18 | (2006.01) |
| A61K 38/50 | (2006.01) |

(52) U.S. Cl.
CPC ........ *A61K 48/0066* (2013.01); *A61K 38/177* (2013.01); *A61K 38/1816* (2013.01); *A61K 38/50* (2013.01); *A61K 48/005* (2013.01); *A61K 48/0041* (2013.01); *A61K 48/0075* (2013.01); *C07H 21/02* (2013.01); *C07K 14/47* (2013.01); *C07K 14/4712* (2013.01); *C07K 14/505* (2013.01); *C12N 15/117* (2013.01); *C12N 15/67* (2013.01); *C12N 15/85* (2013.01); *C12Q 1/68* (2013.01); *C12Y 305/04004* (2013.01); *A61K 48/00* (2013.01); *C12N 2310/17* (2013.01); *C12N 2310/33* (2013.01); *C12N 2310/3341* (2013.01); *C12N 2800/95* (2013.01)

(58) Field of Classification Search
USPC ....................................................... 536/24.5
See application file for complete search history.

(56) References Cited

U.S. PATENT DOCUMENTS

| | | |
|---|---|---|
| 6,127,535 A | 10/2000 | Beigelman |
| 6,326,174 B1 | 12/2001 | Joyce et al. |
| 8,217,016 B2 | 7/2012 | Hoerr et al. |
| 2003/0171253 A1 | 9/2003 | Ma et al. |
| 2005/0032730 A1 | 2/2005 | Von Der Mulbe et al. |
| 2005/0089913 A1 | 4/2005 | Williams |
| 2005/0137155 A1 | 6/2005 | McSwiggen et al. |
| 2006/0008910 A1 | 1/2006 | MacLachlan et al. |
| 2006/0247195 A1 | 11/2006 | Ray |
| 2007/0280929 A1 | 12/2007 | Hoerr et al. |
| 2008/0267873 A1 | 10/2008 | Hoerr et al. |
| 2010/0239608 A1 | 9/2010 | Von Der Mulbe et al. |
| 2010/0303851 A1 | 12/2010 | Hoerr et al. |
| 2011/0077287 A1 | 3/2011 | Von Der Mulbe et al. |
| 2011/0269950 A1 | 11/2011 | Von Der Mulbe et al. |
| 2011/0311472 A1 | 12/2011 | Hoerr et al. |
| 2012/0009221 A1 | 1/2012 | Hoerr et al. |

FOREIGN PATENT DOCUMENTS

| | | |
|---|---|---|
| WO | WO 99/14346 | 3/1999 |
| WO | WO 99/33982 | 7/1999 |
| WO | WO 99/040186 | 8/1999 |

(Continued)

OTHER PUBLICATIONS

Heilman et al., "Internal 6-methyladenine residues increase the in vitro translation efficiency of dihydrofolate reductase messenger RNA," The International Journal of Biochemistry & Cell Biology, 1996, 28:823-829.

(Continued)

*Primary Examiner* — Kimberly Chong
(74) *Attorney, Agent, or Firm* — Riverside Law LLP

(57) ABSTRACT

This invention provides RNA, oligoribonucleotide, and polyribonucleotide molecules comprising pseudouridine or a modified nucleoside, gene therapy vectors comprising same, methods of synthesizing same, and methods for gene replacement, gene therapy, gene transcription silencing, and the delivery of therapeutic proteins to tissue in vivo, comprising the molecules. The present invention also provides methods of reducing the immunogenicity of RNA, oligoribonucleotide, and polyribonucleotide molecules.

15 Claims, 16 Drawing Sheets

Specification includes a Sequence Listing.

(56) References Cited

FOREIGN PATENT DOCUMENTS

WO     WO 00/27340     5/2000
WO     WO 09/127060     10/2009

OTHER PUBLICATIONS

Baker et al., "RNA-Guided RNA modification: functional organization of the archaeal H/ACA RNP," Genes & Dev., published online May 3, 2005, 19:1238-1248.
Sousa, "Use of T7 RNA Polymerase and Its Mutants for Incorporation of Nucleoside Analogs into RNA," Methods in Enzymology, 2000, 317:65-74.
Zimmerman, et al., "Electrolyte- and pH-stabilities of aqueous solid lipid nanoparticle (SLN) dispersions in artificial gastrointestinal media," Eur J Pharmaceutics and Biopharmaceutics, Sep. 2001, 52:203-210.
Hancock, "Reticulocyte Lysate Assay for in Vitro Translation and Posttranslational Modification of Ras Proteins," Methods in Enzymology, 1995, 255:60-65.
Copreni, et al., "Lentivirus-mediated gene transfer to the respiratory epithelium: a promising approach to gene therapy of cystic fibrosis," Gene Therapy, Oct. 2004, 11, Supplement 1:S67-S75.
Pradilla, et al., "Prevention of vasospasm following subarachnoid hemorrhage in rabbits by anti-CD11/CD18 monoclonal antibody therapy," J Neurosurg, Jul. 2004, 101:88-92.
Krieg, et al., "Functional messenger RNAs are produced by SP6 in vitro transcription of cloned cDNAs," Nucleic Acids Research, Sep. 1984, 12(18):7057-7070.
Yu, et al., "Sustained correction of B-cell development and function in a murine model of X-linked agammaglobulinemia (XLA) using retroviral-mediated gene transfer," Blood, republished online May 2004, 104(5):1281-1290.
Guo, et al., "Structure and function of a cap-independent translation element that functions in either the 3' or the 5' untranslated region," RNA, Dec. 2000, 6:1808-1820.
Koski, et al., "Cutting Edge: Innate Immune System Discriminates between RNA Containing Bacterial versus Eukaryotic Structural Features That Prime for High-Level IL-12 Secretion by Dendritic Cells," The Journal of Immunology, Apr. 2004, 172(7):3989-3993.
Desrosiers, et al., "Identification of Methylated Nucleosides in Messenger RNA from Novikoff Hepatoma Cells," Proc. Nat. Acad. Sci. USA, Oct. 1974, 71(10):3971-3975.
Gasche et al., "Sequential Treatment of Anemia in Ulcerative Colitis with Intravenous Iron and Erythropoletin Digestion," May 1999, 60(3):262-267.
Paradi, et al., "Changes in the content of modified nucleotides in wheat rRNA during greening," Biologia Plantarum (Prague), 2003, 47(1):33-38.
Saponara, et al., "The isolation from ribonucleic acid of substituted uridines containing alpha-aminobutyrate moieties derived from methionine," Biochimica et Biophysica Acta, Apr. 27, 1974, 349(1):61-77.
Smith, et al., "RNA modified uridines: VI: Conformations of 3-(3-(S)-amino-3-carboyxpropyl)uridine (acp-3u) from tRNA and 1-methyl-3-(3-(S)-amino-3-carboxypropyl)pseudouridine (m-lacp-3-PSI) from rRNA," Nucleosides and Nucleotides, 1992, 11(10):1683-1694.
Aurup et al., "Translation of 2'-modified mRNA in vitro and in vivo," Nucleic Acids Research, Jan. 1, 1994, 22(23):4963-4968.
Chui, et al., "Synthesis of helix 69 of *Escherichia coli* 23S rRNA containing its natural modified nucleosides, m<3>[psi] and [psi]," Journal of Organic Chemistry, Dec. 13, 2002, 67(25):8847-8854.
Kariko et al., "mRNA Is an Endogenous Ligand for Toll-like Receptor 3," Journal of Biological Biochemistry, American Society for Biochemistry and Molecular Biology Inc. US, Mar. 26, 2004, 279(13):12542-12550.
Bloch, et al., "Sequence-Dependence of the Conformational Changes Induces by the 5 Methylcytosine in Synthetic RNA Oligomers," FEBS Letters, 1987, 219(2):464-468.
Charette, et al., "Pseudouridine in RNA: What, where, how and why," IUBMB Life, 2000, 49(5):341-351.
Gilboa, et al., "Cancer immunotherapy with mRNA-transfected dendritic cells," Immunological Reviews, Jun. 2004, 199(1):251-263.
Ross, et al., "Synthesis and incorporation of 2'-0-methyl-pseudouridine into oligonucleotides," Nucelosides & Nucleotides, Jul. 1, 1997, 16(7/9):1547-1549.
Kariko, et al., "Suppression of RNA recognition by Toll-like receptors: the impact of nucleoside modification and the evolutionary origin of RNA," Immunity, Aug. 23, 2005, 23(2):165-175.
Kariko, et al., "Incorporation of pseudouridine into mRNA yields superior nonimmmunogenic vector with increased translational capacity and biological stability," Molecular Therapy: The Journal of the American Society of Gene Therapy, Nov. 2008, 16(11):1833-1840.
Kahan et al., "The Role of Deoxyribonucleic Acid in Ribonucleic Acid Synthesis," The Journal of Biological Chemistry, Dec. 1962, 437(12):3778-3785.
Goldberg et al., "The Incorporation of 5-Ribosyluracil Triphosphate into RNA in Nuclear Extracts of Mammalian Cells," Biochemical and Biophysical Research Communications, 1961, 6(5):394-398.
Slapikoff et al., "Mechanism of Ribonucleic Acid Polymerase Action. Effect of Nearest Neighbors on Competition between Uridine Triphosphate and Uridine Triphosphate Analogs for Incorporation into Ribonucleic Acid," Biochemistry, Dec. 1967, 6(12):3654-3658.
Wilkie et al., "Regulation of mRNA translation by 5'- and 3'-UTR-binding factors," Trends in Biochemical Sciences, 2003, 28:182-188.
Lian et al., "Trends and Developments in Liposome Drug Delivery Systems," J. Pharmaceutical Science, 2001, 90:667-680.
Shingo et al., "Erythropoietin Regulates the In Vitro and In Vivo Production of Neuronal Progenitors by Mammalian Forebrain Neural Stem Cells," J. Neuroscience, 2001: 9733-9743.
Goldberg et al., "Comparative Utilization of Pseudouridine Triphosphate and Uridine Triphosphate by Ribonucleic Acid Polymerase," The Journal of Biological Chemistry, May 1963, 238(5):1793-1800.
Chen et al., Biochemistry, 1993, 32:10249-10253.
Agris et al., Biochimie, 1995, 77:125-134.

Activation of PKR by mRNAs

A

B

SEQUENCE LISTING

<160> NUMBER OF SEQ ID NOS: 11

<210> SEQ ID NO 1
<211> LENGTH: 1863
<212> TYPE: RNA
<213> ORGANISM: Photinus pyralis

<400> SEQUENCE: 1

```
ggaauucuca acacaacaua uacaaaacaa acgaaucuca agcaaucaag cauucuacuu    60
cuauugcagc aauuuaaauc auuucuuuua aagcaaagca auuuucugaa aauuuucacc   120
auuuacgaac gauagccaug gaagacgcca aaaacauaaa gaaaggcccg gcgccauucu   180
auccucuaga ggauggaacc gcuggagagc aacugcauaa ggcuaugaag agauacgccc   240
ugguuccugg aacaauugcu uuuacagaug cacauaucga ggugaacauc acguacgcgg   300
aauacuucga aauguccguu cgguuggcag aagcuaugaa acgauauggg cugaauacaa   360
aucacagaau cgucguaugc agugaaaacu cucuucaauu cuuuaugccg guguugggcg   420
cguuauuuau cggaguugca guugcgcccg cgaacgacau uuauaaugaa cgugaauugc   480
ucaacaguau gaacauuucg cagccuaccg uaguguuugu uuccaaaaag gguugcaaa    540 aaauuugaa cgugcaaaaa aaauuaccaa uaaccagaa aauuauuauc auggauucua   600
aaacggauua ccagggauuu cagucgaugu acacguucgu cacaucucau cuaccucccg   660
guuuuaauga auacgauuuu guaccagagu ccuuugaucg ugacaaaaca auugcacuga   720
```

| | |
|---|---:|
| uaaugaauuc cucuggaucu acuggguuac cuaagggugu ggcccuuccg cauagaacug | 780 |
| ccugcgucag auucucgcau gccagagauc uauuuuugg caaucaaauc auuccggaua | 840 |
| cugcgauuuu aaguguugu ccauccauc acgguuuugg aauguuuacu acacucggau | 900 |
| auuugauaug uggauuucga gucgucuuaa uguauagauu ugaagaagag cuguuuuuac | 960 |
| gaucccuuca ggauuacaaa auucaaagug cguugcuagu accaacccua uuucauucu | 1020 |
| ucgccaaaag cacucugauu gacaaauacg auuuaucuaa uuuacacgaa auugcuucg | 1080 |
| ggggcgcacc ucuuucgaaa aagucgggg aagcgguugc aaaacgcuuc caucuuccag | 1140 |
| ggauacgaca aggauauggg cucacugaga cuacaucagc uauucugauu cacccgagg | 1200 |
| gggaugauaa accgggcgcg gucgguaaag uuguccauu uuugaagcg aagguugugg | 1260 |
| aucuggauac cggaaaacg cugggcguua ucagagagg cgaauuaugu gucagaggac | 1320 |
| cuaugauuau guccgguuau guaaacaauc cggaagcgac caacgccuug auugacaagg | 1380 |
| auggauggcu acauucugga gacauagcuu acgggacga agacgaacac ucuucauag | 1440 |
| uugaccgcuu gaagucuuua auuaaauaca aaggauauca ggugggcccc gcugaauugg | 1500 |
| aaucgauauu guuacaacac cccaacaucu cgacgcggg cguggcaggu cuucccgacg | 1560 |
| augacgccgg ugaacuuccc gccgccguug uuguuugga gcacggaaag acgaugacgg | 1620 |
| aaaaagagau cguggauuac guggccaguc aaguaacaac cgcgaaaaag uugcgcggag | 1680 |
| gaguugugu uguggacgaa guaccgaaag gucuuaccgg aaaacucgac gcaagaaaaa | 1740 |
| ucagagagau ccucauaaag gccaagaagg gcggaaaguc caaauuguaa aauguaacuc | 1800 |
| uagaggaucc ccaaaaaaa aaaaaaaaa aaaaaaaaa aaaaaaaaa aaaaaaaaa | 1860 |
| aca | 1863 |

<210> SEQ ID NO 2
<211> LENGTH: 1571
<212> TYPE: RNA
<213> ORGANISM: Renilla reniformis

<400> SEQUENCE: 2

| | |
|---|---:|
| ggcuagccac caugacuucg aaaguuuaug auccagaaca aaggaaacgg augauaacug | 60 |
| guccgcagug gugggccaga uguaaacaaa ugaauguucu ugauucauuu auuaauuauu | 120 |
| augauucaga aaaacaugca gaaaaugcug uuauuuuuu acaugguaac gcggccucuu | 180 |
| cuuauuuaug cgacauguu ugccacaua uugagccagu agcgcggugu auuauaccag | 240 |
| accuuauugg uaugggcaaa ucaggcaaau cugguaaugg uucuuauagg uuacuugauc | 300 |
| auuacaaaua ucuuacugca gguuugaac ucuuaauuu accaaagaag aucauuuug | 360 |
| ucggccauga uggggugcu uguuggcau ucauuauag cuaugagcau caagauaaga | 420 |
| ucaaagcaau aguucacgcu gaaaguguag uagaugugau ugaaucaugg gaugaauggc | 480 |
| cugauauuga agaagauauu gcguugauca aacugaaga aggagaaaaa augguuuugg | 540 |
| agaauaacuu cuucguggaa accauguugc caucaaaaau caugagaaag uuagaaccag | 600 |
| aagaauuugc agcauaucuu gaaccauuca aagagaaagg ugaaguucgu cguccaacau | 660 |
| uaucauggcc ucgugaaauc ccguuaguaa aaggugguaa accugacguu uacaaauug | 720 |
| uuaggaauua uaaugcuuau cuacgugcaa gugaugauuu accaaaaug uuuauugaau | 780 |
| cggacccagg auucuuuucc aaugcuauug uugaaggug caagaaguuu ccuaauacug | 840 |
| aauuugucaa aguaaaaggu cuucauuuuu cgcaagaaga ugcaccugau gaaaugggaa | 900 |

| | |
|---|---:|
| aauauaucaa aucguucguu gagcgaguuc ucaaaaauga caaaugucg acggggccc | 960 |
| cuaggaauuu uuuagggaag aucuggccuu ccuacaaggg aaggccaggg aauuuucuuc | 1020 |
| agagcagacc agagccaaca gccccaccag aagagagcuu caggucuggg guagagacaa | 1080 |
| caaccccccc ucagaagcag gagccgauag acaaggaacu guauccuuua acuucccuca | 1140 |
| gaucacucuu uggcaacgac cccucgucac aauaaagaua gggggggcaac uaaagggauc | 1200 |
| ggccgcuucg agcagacaug auaagauaca uugaugaguu uggacaaacc acaacuagaa | 1260 |
| ugcagugaaa aaaaugcuuu auuugugaaa uuugugaugc auugcuuua uuuguaacca | 1320 |
| uuauaagcug caauaaacaa guuaacaaca acauuugcau ucauuuuaug uuucagguuc | 1380 |
| aggggaggu gugggagguu uuuuaaagca aguaaaaccu cuacaaaugu gguaaaaucg | 1440 |
| auaaguuuaa acagauccag guggcacuuu ucggggaaau gugcgcggaa cccauauuug | 1500 |
| uuuauuuuuc uaaauacauu caaauaugua uccgcucaug agacaauaac ccugauaaau | 1560 |
| gcuucaauaa u | 1571 |

<210> SEQ ID NO 3
<211> LENGTH: 726
<212> TYPE: RNA
<213> ORGANISM: Homo sapiens

<400> SEQUENCE: 3

| | |
|---|---:|
| gggaauuugg cccucgaggc caagaauucg gcacgaggca cgcggccagc cagcagacag | 60 |
| aggacucuca uuaaggaagg uguccugugc ccugacccua caagaugcca agagaagaug | 120 |
| cucacuucau cuaugguuac cccaagaagg ggcacggcca cucuuacacc acggcugaag | 180 |
| aggccgcugg gaucggcauc cugacaguga uccuggagu cuuacugcuc aucggcuguu | 240 |
| gguauuguag aagacgaaau ggauacagag ccuugaugga uaaaagucuu caguuggca | 300 |
| cucaaugugc cuuaacaaga agaugcccac aagaaggguu ugaucaucgg gacagcaaag | 360 |
| ugucucuuca agagaaaaac ugugaaccug ugguucccaa ugcuccaccu gcuuaugaga | 420 |
| aacucucugc agaacaguca ccaccaccuu auucaccuua agagccagcg agacaccuga | 480 |
| gacaugcuga aauuauuucu cucacacuuu ugcuugaauu uaauacagac aucuaauguu | 540 |
| cuccuuugga augguguagg aaaaaugcaa gccaucucua auaauaaguc aguguuaaaa | 600 |
| uuuuaguagg uccgcuagca guacuaauca ugugaggaaa ugaugagaaa uauuaaauug | 660 |
| ggaaaacucc aucaauaaau guugcaaugc augauaaaaa aaaaaaaaaa aaaacugcg | 720 |
| gccgca | 726 |

<210> SEQ ID NO 4
<211> LENGTH: 712
<212> TYPE: RNA
<213> ORGANISM: Homo sapiens

<400> SEQUENCE: 4

| | |
|---|---:|
| gggaauaagc uugcggccgc aguuuuuuu uuuuuuuuu uuaucaugca uugcaacauu | 60 |
| uauugaugga guuucccaa uuuaauauuu cucaucauuu ccucacauga uuaguacugc | 120 |
| uagcggaccu acuaaaauuu uaacacugac uuauuauuag agauggcuug cauuuuuccu | 180 |
| acaccauucc aaaggagaac auuagaugu uguauaaauu caagcaaaag gugagagaa | 240 |
| auaauuucag cauguccag gugucucgcu ggcucuuaag gugaauaagg uggugugac | 300 |
| uguucugcag agaguuucuc auaagcaggu ggagcauugg gaaccacagg uucacaguuu | 360 |
| uucucuugaa gagacacuuu gcugucccga ugaucaaacc cuucuugugg gcaucuucuu | 420 |

```
guuaaggcac auugagugcc aacaugaaga cuuuuaucca ucaaggcucu guauccauuu      480
cgucuucuac aauaccaaca gccgaugagc aguaagacuc ccaggaucac ugucaggaug      540
ccgaucccag cggccucuuc agccguggug uaagaguggc cgugccccuu cuugggguaa      600
ccauagauga agugagcauc uucucuuggc aucuuguagg gucagggcac aggacaccuu      660
ccuuaaugag aguccucugu cugcuggcug gccgcgugcc ucgugccgaa uu              712

<210> SEQ ID NO 5
<211> LENGTH: 492
<212> TYPE: RNA
<213> ORGANISM: Homo sapiens

<400> SEQUENCE: 5
gggagaccaa gcuggcuagc agucauccaa cagaaucaug agacagacuu ugccuuguau       60
cuauuuuggg ggggccuuuu gcccuuuggg augcugugug cauccuccac caccaagugc      120
acuguuagcc augaaguugc ugacugcagc caccugaagu ugacucaggu acccgaugau      180 cucccacaa acauaacagu guugaaccuu acccauaauc aacucagaag auuaccagcc       240
gccaacuuca caagguauag ccagcuaacu agcuuggaug uaggauuuaa caccaucuca      300
aaacuggagc cagaauugug ccagaaacuu cccauguuaa aaguuuugaa ccuccagcac      360
aaugagcuau cucaacuuuc ugauaaaacc uuugccuucu gcacgaauuu gacugaacuc      420
caucucaugu ccaacucaau ccagaaaauu aaaaauaauc ccuuugucaa gcagaagaau      480
uuaaucacau ua                                                         492

<210> SEQ ID NO 6
<211> LENGTH: 21
<212> TYPE: RNA
<213> ORGANISM: Artificial Sequence
<220> FEATURE:
<223> OTHER INFORMATION: Chemically synthesized

<400> SEQUENCE: 6
uggauccggc uuugagaucu u                                               21

<210> SEQ ID NO 7
<211> LENGTH: 21
<212> TYPE: RNA
<213> ORGANISM: Artificial Sequence
<220> FEATURE:
<223> OTHER INFORMATION: Chemically synthesized
<220> FEATURE:
<221> NAME/KEY: modified_base
<222> LOCATION: (11)..(11)
<223> OTHER INFORMATION: um

<400> SEQUENCE: 7
uggauccggc uuugagaucu u                                               21

<210> SEQ ID NO 8
<211> LENGTH: 21
<212> TYPE: RNA
<213> ORGANISM: Artificial Sequence
<220> FEATURE:
<223> OTHER INFORMATION: Chemically synthesized
<220> FEATURE:
<221> NAME/KEY: modified_base
<222> LOCATION: (6)..(6)
<223> OTHER INFORMATION: m5c

<400> SEQUENCE: 8
```

```
uggauccggc uuugagaucu u                                          21

<210> SEQ ID NO 9
<211> LENGTH: 21
<212> TYPE: RNA
<213> ORGANISM: Artificial Sequence
<220> FEATURE:
<223> OTHER INFORMATION: Chemically synthesized
<220> FEATURE:
<221> NAME/KEY: modified_base
<222> LOCATION: (12)..(12)
<223> OTHER INFORMATION: p

<400> SEQUENCE: 9
uggauccggc uuugagaucu u                                          21

<210> SEQ ID NO 10
<211> LENGTH: 31
<212> TYPE: RNA
<213> ORGANISM: Artificial Sequence
<220> FEATURE:
<223> OTHER INFORMATION: Chemically synthesized

<400> SEQUENCE: 10
gggagacagg gguguccgcc auuccaggu u                                31

<210> SEQ ID NO 11
<211> LENGTH: 31
<212> TYPE: RNA
<213> ORGANISM: Artificial Sequence
<220> FEATURE:
<223> OTHER INFORMATION: Chemically synthesized

<400> SEQUENCE: 11
gggagacagg cuauaacuca cauaauguau u                               31
```

US 10,232,055 B2

RNA CONTAINING MODIFIED NUCLEOSIDES AND METHODS OF USE THEREOF

CROSS-REFERENCE TO RELATED APPLICATIONS

The present application is a continuation of and claims priority to U.S. patent application Ser. No. 14/456,302, filed Aug. 11, 2014, which is a continuation of and claims priority to U.S. patent application Ser. No. 13/839,023, filed Mar. 15, 2013, which is a continuation of and claims priority to U.S. patent application Ser. No. 13/585,517, filed Aug. 14, 2012, which is a continuation of and claims priority to U.S. patent application Ser. No. 11/990,646, filed Mar. 27, 2009, which is a 35 U.S.C. § 371 national phase application from, and claiming priority to International App. No. PCT/US06/32372, filed Aug. 21, 2006, which claims priority to U.S. Provisional App. Ser. No. 60/710,164, filed Aug. 23, 2005, all of which applications are hereby incorporated by reference in their entireties herein.

STATEMENT REGARDING FEDERALLY SPONSORED RESEARCH OR DEVELOPMENT

This invention was made with government support under grant numbers AI060505, AI50484, and DE14825 awarded by the National Institutes of Health. The Government therefore has certain rights in this invention.

FIELD OF INVENTION

This invention provides RNA, oligoribonucleotide, and polyribonucleotide molecules comprising pseudouridine or a modified nucleoside, gene therapy vectors comprising same, methods of synthesizing same, and methods for gene replacement, gene therapy, gene transcription silencing, and the delivery of therapeutic proteins to tissue in vivo, comprising the molecules. The present invention also provides methods of reducing the immunogenicity of RNA, oligoribonucleotide, and polyribonucleotide molecules.

BACKGROUND OF THE INVENTION

All naturally occurring RNA is synthesized from four basic ribonucleotides ATP, CTP, UTP and GTP, but some of the incorporated nucleosides are modified post-transcriptionally in almost all types of RNA. Nearly one hundred different nucleoside modifications have been identified in RNA (Rozenski, J, Crain, P, and McCloskey, J. (1999). The RNA Modification Database: 1999 update. Nucl Acids Res 27: 196-197). The extent and nature of modifications vary and depend on the RNA type as well as the evolutionary level of the organism from where the RNA is derived. Ribosomal RNA, the major constituent of cellular RNA, contains significantly more nucleoside modifications in mammalian cells than bacteria. Human rRNA, for example, has 10-times more pseudouridine ($\Psi$) and 25-times more 2'-O-methylated nucleosides than bacterial rRNA, while rRNA from mitochondria has very few modifications. Transfer RNA (tRNA) is the most heavily modified subgroup of RNA. In mammalian tRNA, up to 25% of the nucleosides are modified, while prokaryotic tRNA contains significantly fewer modifications. Bacterial messenger RNA (mRNA) contains no nucleoside modifications, while mammalian mRNA contains modified nucleosides such as 5-methylcytidine ($m^5C$), N6-methyladenosine ($m^6A$), inosine and 2'-O-methylated nucleosides, in addition to N7-methylguanosine ($m^7G$), which is part of the 5'-terminal cap. The role of nucleoside modifications on the immuno-stimulatory potential and on the translation efficiency of RNA, however, is not known.

SUMMARY OF THE INVENTION

This invention provides RNA, oligoribonucleotide, and polyribonucleotide molecules comprising pseudouridine or a modified nucleoside, gene therapy vectors comprising same, gene therapy methods and gene transcription silencing methods comprising same, methods of reducing an immunogenicity of same, and methods of synthesizing same.

In one embodiment, the present invention provides a messenger RNA comprising a pseudouridine residue.

In another embodiment, the present invention provides an RNA molecule encoding a protein of interest, said RNA molecule comprising a pseudouridine residue.

In another embodiment, the present invention provides an in vitro-transcribed RNA molecule, comprising a pseudouridine or a modified nucleoside.

In another embodiment, the present invention provides an in vitro-synthesized oligoribonucleotide, comprising a pseudouridine or a modified nucleoside, wherein the modified nucleoside is $m^5C$, $m^5U$, $m^6A$, $s^2U$, $\Psi$, or 2'-O-methyl-U.

In another embodiment, the present invention provides a gene-therapy vector, comprising an in vitro-synthesized polyribonucleotide molecule, wherein the polyribonucleotide molecule comprises a pseudouridine or a modified nucleoside.

In another embodiment, the present invention provides a double-stranded RNA (dsRNA) molecule containing, as part of its sequence, a pseudouridine or a modified nucleoside and further comprising an siRNA or shRNA. In another embodiment, the dsRNA molecule is greater than 50 nucleotides in length. Each possibility represents a separate embodiment of the present invention.

In another embodiment, the present invention provides a method for inducing a mammalian cell to produce a recombinant protein, comprising contacting the mammalian cell with an in vitro-synthesized RNA molecule encoding the recombinant protein, the in vitro-synthesized RNA molecule comprising a pseudouridine or a modified nucleoside, thereby inducing a mammalian cell to produce a recombinant protein.

In another embodiment, the present invention provides a method for treating anemia in a subject, comprising contacting a cell of the subject with an in vitro-synthesized RNA molecule, the in vitro-synthesized RNA molecule encoding erythropoietin, thereby treating anemia in a subject.

In another embodiment, the present invention provides a method for treating a vasospasm in a subject, comprising contacting a cell of the subject with an in vitro-synthesized RNA molecule, the in vitro-synthesized RNA molecule encoding inducible nitric oxide synthase (iNOS), thereby treating a vasospasm in a subject.

In another embodiment, the present invention provides a method for improving a survival rate of a cell in a subject, comprising contacting the cell with an in vitro-synthesized RNA molecule, the in vitro-synthesized RNA molecule encoding a heat shock protein, thereby improving a survival rate of a cell in a subject.

In another embodiment, the present invention provides a method for decreasing an incidence of a restenosis of a blood vessel following a procedure that enlarges the blood vessel, comprising contacting a cell of the blood vessel with an in vitro-synthesized RNA molecule, the in vitro-synthesized RNA molecule encoding a heat shock protein, thereby decreasing an incidence of a restenosis in a subject.

In another embodiment, the present invention provides a method for increasing a hair growth from a hair follicle is a scalp of a subject, comprising contacting a cell of the scalp with an in vitro-synthesized RNA molecule, the in vitro-synthesized RNA molecule encoding a telomerase or an immunosuppressive protein, thereby increasing a hair growth from a hair follicle.

In another embodiment, the present invention provides a method of inducing expression of an enzyme with antioxidant activity in a cell, comprising contacting the cell with an in vitro-synthesized RNA molecule, the in vitro-synthesized RNA molecule encoding the enzyme, thereby inducing expression of an enzyme with antioxidant activity in a cell.

In another embodiment, the present invention provides a method for treating cystic fibrosis in a subject, comprising contacting a cell of the subject with an in vitro-synthesized RNA molecule, the in vitro-synthesized RNA molecule encoding Cystic Fibrosis Transmembrane Conductance Regulator (CFTR), thereby treating cystic fibrosis in a subject.

In another embodiment, the present invention provides a method for treating an X-linked agammaglobulinemia in a subject, comprising contacting a cell of the subject with an in vitro-synthesized RNA molecule, the in vitro-synthesized RNA molecule encoding a Bruton's tyrosine kinase, thereby treating an X-linked agammaglobulinemia.

In another embodiment, the present invention provides a method for treating an adenosine deaminase severe combined immunodeficiency (ADA SCID) in a subject, comprising contacting a cell of the subject with an in vitro-synthesized RNA molecule, the in vitro-synthesized RNA molecule encoding an ADA, thereby treating an ADA SCID.

In another embodiment, the present invention provides a method for producing a recombinant protein, comprising contacting an in vitro translation apparatus with an in vitro-synthesized polyribonucleotide, the in vitro-synthesized polyribonucleotide comprising a pseudouridine or a modified nucleoside, thereby producing a recombinant protein.

In another embodiment, the present invention provides a method of synthesizing an in vitro-transcribed RNA molecule comprising a modified nucleotide with a pseudouridine modified nucleoside, comprising contacting an isolated polymerase with a mixture of unmodified nucleotides and the modified nucleotide.

In another embodiment, the present invention provides an in vitro transcription apparatus, comprising: an unmodified nucleotide, a nucleotide containing a pseudouridine or a modified nucleoside, and a polymerase. In another embodiment, the present invention provides an in vitro transcription kit, comprising: an unmodified nucleotide, a nucleotide containing a pseudouridine or a modified nucleoside, and a polymerase. Each possibility represents a separate embodiment of the present invention.

BRIEF DESCRIPTION OF THE FIGURES

FIG. 2, comprising FIGS. 2A through 2C. TLR-dependent activation by RNA demonstrates that m6A and s2U modification blocks TLR3 signaling, while all modifications block TLR7 and TLR8 signaling, and that less modified bacterial RNA and unmodified in vitro-transcribed RNA activates all three TLR.

FIG. 4, comprising FIGS. 4A and 4B. Activation of DC by RNA demonstrates that all modifications inhibit DC activation. MDDC were treated for 20 h with Lipofectin® alone, Lipofectin®-R-848 (1 μg/ml) or RNA-1571, modified as indicated (5 μg/ml).

FIG. 5, comprising FIGS. 5A through 5C. Capped RNA-1571 containing different amounts (0, 1, 10, 50, 90, 99 and 100% of modified nucleoside, relative to the corresponding unmodified NTP) were transcribed, and it was found that modification of only a few nucleosides resulted in an inhibition of activation of DC.

FIG. 6, comprising FIGS. 6A through 6C. TNF-α expression by oligoribonucleotide-transfected DCs demonstrates that as few as one modified nucleoside reduces DC activation.

FIG. 7, comprising FIGS. 7A and 7B.

FIG. 10, comprising FIGS. 10A and 10B. Increased expression of renilla from pseudouridine-containing mRNA in cultured cells.

FIG. 11, comprising FIGS. 11A through 11C.

FIG. 12, comprising FIGS. 12A through 12D.

DETAILED DESCRIPTION OF THE INVENTION

Figure 1:
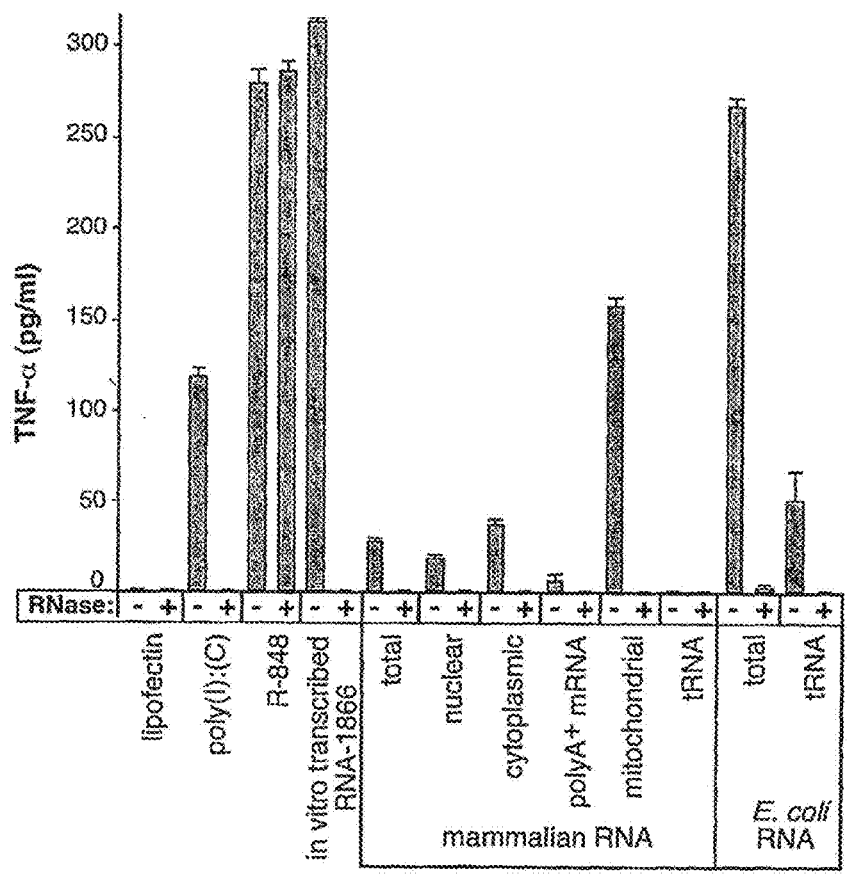
FIG. 1. Production of TNF-α by MDDCs transfected with natural RNA, demonstrating that unmodified in vitro-synthesized RNA and bacterial and mitochondrial RNA is highly immunogenic, while other mammalian RNA is weakly immunogenic. Human MDDCs were incubated with Lipofectin® alone, or complexed with R-848 (1 μg/ml), or RNA (5 μg/ml) from 293 cells (total, nuclear and cytoplasmic RNAs), mouse heart (polyA+mRNA), human platelet mitochondrial RNA, bovine tRNA, bacterial tRNA and total RNA (E. coli) with or without RNase digestion. After 8 h, TNF-α was measured in the supernatants by ELISA. Mean values±SEM are shown. Results are representative of 3 independent experiments.

This invention provides RNA, oligoribonucleotide, and polyribonucleotide molecules comprising pseudouridine or a modified nucleoside, gene therapy vectors comprising same, gene therapy methods and gene transcription silencing methods comprising same, methods of reducing an immunogenicity of same, and methods of synthesizing same.

In one embodiment, the present invention provides a messenger RNA comprising a pseudouridine residue. In another embodiment, the messenger RNA encodes a protein of interest. Each possibility represents a separate embodiment of the present invention.

In another embodiment, the present invention provides an RNA molecule encoding a protein of interest, said RNA molecule comprising a pseudouridine residue.

In another embodiment, the present invention provides in vitro-transcribed RNA molecule, comprising a pseudouridine.

In another embodiment, the present invention provides an in vitro-transcribed RNA molecule, comprising a modified nucleoside.

As provided herein, the present invention provides methods for synthesizing in vitro-transcribed RNA molecules, comprising pseudouridine and/or modified nucleosides.

In another embodiment, the present invention provides a messenger RNA molecule comprising a pseudouridine residue In another embodiment, an in vitro-transcribed RNA molecule of methods and compositions of the present invention is synthesized by T7 phage RNA polymerase. In another embodiment, the molecule is synthesized by SP6 phage RNA polymerase. In another embodiment, the molecule is synthesized by T3 phage RNA polymerase. In another embodiment, the molecule is synthesized by a polymerase selected from the above polymerases.

In another embodiment, the in vitro-transcribed RNA molecule is an oligoribonucleotide. In another embodiment, the in vitro-transcribed RNA molecule is a polyribonucleotide. Each possibility represents a separate embodiment of the present invention.

In another embodiment, the present invention provides an in vitro-synthesized oligoribonucleotide, comprising a pseudouridine or a modified nucleoside, wherein the modified nucleoside is $m^5C$, $m^5U$, $m^6A$, $s^2U$, Ψ, or 2'-O-methyl-U.

In another embodiment, the present invention provides an in vitro-synthesized polyribonucleotide, comprising a pseudouridine or a modified nucleoside, wherein the modified nucleoside is $m^5C$, $m^5U$, $m^6A$, $s^2U$, Ψ, or 2'-O-methyl-U.

In another embodiment, the in vitro-synthesized oligoribonucleotide or polyribonucleotide is a short hairpin (sh) RNA. In another embodiment, the in vitro-synthesized oligoribonucleotide is a small interfering RNA (siRNA). In another embodiment, the in vitro-synthesized oligoribonucleotide is any other type of oligoribonucleotide known in the art. Each possibility represents a separate embodiment of the present invention.

In another embodiment, an RNA, oligoribonucleotide, or polyribonucleotide molecule of methods and compositions of the present invention further comprises an open reading frame that encodes a functional protein. In another embodiment, the RNA molecule or oligoribonucleotide molecule functions without encoding a functional protein (e.g. in transcriptional silencing), as an RNzyme, etc. Each possibility represents a separate embodiment of the present invention.

In another embodiment, the RNA, oligoribonucleotide, or polyribonucleotide molecule further comprises a poly-A tail. In another embodiment, the RNA, oligoribonucleotide, or polyribonucleotide molecule does not comprise a poly-A tail. Each possibility represents a separate embodiment of the present invention.

In another embodiment, the RNA, oligoribonucleotide, or polyribonucleotide molecule further comprises an m7GpppG cap. In another embodiment, the RNA, oligoribonucleotide, or polyribonucleotide molecule does not comprise an m7GpppG cap. Each possibility represents a separate embodiment of the present invention.

In another embodiment, the RNA, oligoribonucleotide, or polyribonucleotide molecule further comprises a cap-independent translational enhancer. In another embodiment, the RNA, oligoribonucleotide, or polyribonucleotide molecule does not comprise a cap-independent translational enhancer. In another embodiment, the cap-independent translational enhancer is a tobacco etch virus (TEV) cap-independent translational enhancer. In another embodiment, the cap-independent translational enhancer is any other cap-independent translational enhancer known in the art. Each possibility represents a separate embodiment of the present invention.

In another embodiment, the present invention provides a gene-therapy vector, comprising an in vitro-synthesized polyribonucleotide molecule, wherein the polyribonucleotide molecule comprises a pseudouridine or a modified nucleoside.

In another embodiment, an RNA, oligoribonucleotide, or polyribonucleotide molecule of methods and compositions of the present invention comprises a pseudouridine. In another embodiment, the RNA molecule or oligoribonucleotide molecule comprises a modified nucleoside. In another embodiment, the RNA molecule or oligoribonucleotide molecule is an in vitro-synthesized RNA molecule or oligoribonucleotide. Each possibility represents a separate embodiment of the present invention.

"Pseudouridine" refers, in another embodiment, to $m^1acp^3Ψ$ (1-methyl-3-(3-amino-3-carboxypropyl) pseudouridine. In another embodiment, the term refers to $m^1Ψ$ (1-methylpseudouridine). In another embodiment, the term refers to Ψm (2'-O-methylpseudouridine. In another embodiment, the term refers to $m^5D$ (5-methyldihydrouridine). In another embodiment, the term refers to $m^3Ψ$ (3-methylpseudouridine). In another embodiment, the term refers to a pseudouridine moiety that is not further modified. In another embodiment, the term refers to a monophosphate, diphosphate, or triphosphate of any of the above pseudouridines. In another embodiment, the term refers to any other pseudouridine known in the art. Each possibility represents a separate embodiment of the present invention.

In another embodiment, an RNA, oligoribonucleotide, or polyribonucleotide molecule of methods and compositions of the present invention is a therapeutic oligoribonucleotide.

In another embodiment, the present invention provides a method for delivering a recombinant protein to a subject, the method comprising the step of contacting the subject with an RNA, oligoribonucleotide, polyribonucleotide molecule, or a gene-therapy vector of the present invention, thereby delivering a recombinant protein to a subject.

In another embodiment, the present invention provides a double-stranded RNA (dsRNA) molecule comprising a pseudouridine or a modified nucleoside and further comprising an siRNA or short hairpin RNA (shRNA). In another embodiment, the dsRNA molecule is greater than 50 nucleotides in length. Each possibility represents a separate embodiment of the present invention.

In another embodiment, the pseudouridine or a modified nucleoside is within the siRNA sequence. In another embodiment, the pseudouridine or a modified nucleoside is outside the siRNA sequence. In another embodiment, 1 or more pseudouridine and/or a modified nucleoside residues are present both within and outside the siRNA sequence. Each possibility represents a separate embodiment of the present invention.

In another embodiment, the siRNA or shRNA is contained internally in the dsRNA molecule. In another embodiment, the siRNA or shRNA is contained on one end of the dsRNA molecule. In another embodiment, one or more siRNA or shRNA is contained on one end of the dsRNA molecule, while another one or more is contained internally. Each possibility represents a separate embodiment of the present invention.

In another embodiment, the length of an RNA, oligoribonucleotide, or polyribonucleotide molecule (e.g. a single-stranded RNA (ssRNA) or dsRNA molecule) of methods and compositions of the present invention is greater than 30 nucleotides in length. In another embodiment, the RNA molecule or oligoribonucleotide is greater than 35 nucleotides in length. In another embodiment, the length is at least 40 nucleotides. In another embodiment, the length is at least 45 nucleotides. In another embodiment, the length is at least 55 nucleotides. In another embodiment, the length is at least 60 nucleotides. In another embodiment, the length is at least 60 nucleotides. In another embodiment, the length is at least 80 nucleotides. In another embodiment, the length is at least 90 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides. In another embodiment, the length is at least 1100 nucleotides. In another embodiment, the length is at least 1200 nucleotides. In another embodiment, the length is at least 1300 nucleotides. In another embodiment, the length is at least 1400 nucleotides. In another embodiment, the length is at least 1500 nucleotides. In another embodiment, the length is at least 1600 nucleotides. In another embodiment, the length is at least 1800 nucleotides. In another embodiment, the length is at least 2000 nucleotides. In another embodiment, the length is at least 2500 nucleotides. In another embodiment, the length is at least 3000 nucleotides. In another embodiment, the length is at least 4000 nucleotides. In another embodiment, the length is at least 5000 nucleotides. Each possibility represents a separate embodiment of the present invention.

In another embodiment, a dsRNA molecule of methods and compositions of the present invention is manufactured by in vitro-transcription.

In another embodiment, the step of in vitro-transcription utilizes T7 phage RNA polymerase. In another embodiment, the in vitro-transcription utilizes SP6 phage RNA polymerase. In another embodiment, the in vitro-transcription utilizes T3 phage RNA polymerase. In another embodiment, the in vitro-transcription utilizes an RNA polymerase selected from the above polymerases. In another embodiment, the in vitro-transcription utilizes any other RNA polymerase known in the art. Each possibility represents a separate embodiment of the present invention.

In another embodiment, the dsRNA molecule is capable of being processed by a cellular enzyme to yield the siRNA or shRNA. In another embodiment, the cellular enzyme is an endonuclease. In another embodiment, the cellular enzyme is Dicer. Dicer is an RNase III-family nuclease that initiates RNA interference (RNAi) and related phenomena by generation of the small RNAs that determine the specificity of these gene silencing pathways (Bernstein E, Caudy A A et al, Role for a bidentate ribonuclease in the initiation step of RNA interference. Nature 2001; 409(6818): 363-6). In another embodiment, the cellular enzyme is any other cellular enzyme known in the art that is capable of cleaving a dsRNA molecule. Each possibility represents a separate embodiment of the present invention.

In another embodiment, the dsRNA molecule contains two siRNA or shRNA. In another embodiment, the dsRNA molecule contains three siRNA or shRNA. dsRNA molecule contains more than three siRNA or shRNA. In another embodiment, the siRNA and/or shRNA are liberated from the dsRNA molecule by a cellular enzyme. Each possibility represents a separate embodiment of the present invention.

In another embodiment, the present invention provides a method for administering an siRNA or shRNA to a cell, comprising administering a dsRNA molecule of the present invention, wherein the cell processes the dsRNA molecule to yield the siRNA or shRNA, thereby administering a siRNA or shRNA to a cell.

In another embodiment, the nucleoside that is modified in an RNA, oligoribonucleotide, or polyribonucleotide molecule of methods and compositions of the present invention is uridine (U). In another embodiment, the modified nucleoside is cytidine (C). In another embodiment, the modified nucleoside is adenine (A). In another embodiment the modified nucleoside is guanine (G). Each possibility represents a separate embodiment of the present invention.

In another embodiment, the modified nucleoside of methods and compositions of the present invention is $m^5C$ (5-methylcytidine). In another embodiment, the modified nucleoside is $m^5U$ (5-methyluridine). In another embodiment, the modified nucleoside is $m^6A$ (N$^6$-methyladenosine). In another embodiment, the modified nucleoside is $s^2U$ (2-thiouridine). In another embodiment, the modified nucleoside is Ψ (pseudouridine). In another embodiment, the modified nucleoside is Um (2'-O-methyluridine).

In other embodiments, the modified nucleoside is $m^1A$ (1-methyladenosine); $m^2A$ (2-methyladenosine); Am (2'-O-methyladenosine); $ms^2m^6A$ (2-methylthio-$N^6$-methyladenosine); $i^6A$ ($N^6$-isopentenyladenosine); $ms^2m^6A$ (2-methylthio-$N^6$isopentenyladenosine); $io^6A$ ($N^6$-(cis-hydroxyisopentenyl)adenosine); $ms^2io^6A$ (2-methylthio-$N^6$-(cis-hydroxyisopentenyl) adenosine); $g^6A$ ($N^6$-glycinylcarbamoyladenosine); $t^6A$ ($N^6$-threonylcarbamoyladenosine); $ms^2t^6A$ (2-methylthio-$N^6$-threonylcarbamoyladenosine); $m^6t^6A$ ($N^6$-methyl-$N^6$-threonylcarbamoyladenosine); $hn^6A$($N^6$-hydroxynorvalylcarbamoyladenosine); $ms^2hn^6A$ (2-methylthio-$N^6$-hydroxynorvalylcarbamoyladenosine); Ar(p) (2'-O-ribosyladenosine (phosphate)); I (inosine); $m^1I$ (1-methylinosine); $m^1Im$ (1,2'-O-dimethylinosine); $m^3C$ (3-methylcytidine); Cm (2'-O-methylcytidine); $s^2C$ (2-thiocytidine); $ac^4C$ ($N^4$-acetylcytidine); $f^5C$ (5-formylcytidine); $m^5Cm$ (5,2'-O-dimethylcytidine); $ac^4Cm$ ($N^4$-acetyl-2'-O-methylcytidine); $k^2C$ (lysidine); $m^1G$ (1-methylguanosine); $m^2G$ ($N^2$-methylguanosine); $m^7G$ (7-methylguanosine); Gm (2'-O-methylguanosine); $m^2_2G$ ($N^2,N^2$-dimethylguanosine); $m^2Gm$ ($N^2,2'$-O-dimethylguanosine); $m^2_2Gm$ ($N^2,N^2,2'$-O-trimethylguanosine); Gr(p) (2'-O-ribosylguanosine (phosphate)); yW (wybutosine); $o_2yW$ (peroxywybutosine); OHyW (hydroxywybutosine); OHyW* (undermodified hydroxywybutosine); imG (wyosine); mimG (methylwyosine); Q (queuosine); oQ (epoxyqueuosine); galQ (galactosyl-queuosine); manQ (mannosyl-queuosine); $preQ_0$ (7-cyano-7-deazaguanosine); $preQ_1$ (7-aminomethyl-7-deazaguanosine); $G^+$ (archaeosine); D (dihydrouridine); $m^5Um$ (5,2'-O-dimethyluridine); $s^4U$ (4-thiouridine); $m^5s^2U$ (5-methyl-2-thiouridine); $s^2Um$ (2-thio-2'-O-methyluridine); $acp^3U$ (3-(3-amino-3-carboxypropyl)uridine); $ho^5U$ (5-hydroxyuridine); $mo^5U$ (5-methoxyuridine); $cmo^5U$ (uridine 5-oxyacetic acid); $mcmo^5U$ (uridine 5-oxyacetic acid methyl ester); $chm^5U$ (5-(carboxyhydroxymethyl)uridine)); $mchm^5U$ (5-(carboxyhydroxymethyl)uridine methyl ester); $mcm^5U$ (5-methoxycarbonylmethyluridine); $mcm^5Um$ (5-methoxycarbonylmethyl-2'-O-methyluridine); $mcm^5s2U$ (5-methoxycarbonylmethyl-2-thiouridine); $nm5s^2U$ (5-aminomethyl-2-thiouridine); $mnm^5U$ (5-methylaminomethyluridine); $mnm^5s^2U$ (5-methylaminomethyl-2-thiouridine); $mnm^5se^2U$ (5-methylaminomethyl-2-selenouridine); $ncm^5U$ (5-carbamoylmethyluridine); $ncm^5Um$ (5-carbamoylmethyl-2'-O-methyluridine); $cmnm^5U$ (5-carboxymethylaminomethyluridine); $cmnm^5Um$ (5-carboxymethylaminomethyl-2'-O-methyluridine); $cmnm^5s^2U$ (5-carboxymethylaminomethyl-2-thiouridine); $m^6_2A$ ($N^6,N^6$-dimethyladenosine); Im (2'-O-methylinosine); $m^4C$ ($N^4$-methylcytidine); $m^4Cm$ ($N^4,2'$-O-dimethylcytidine); $hm^5C$ (5-hydroxymethylcytidine); $m^3U$ (3-methyluridine); $cm^5U$ (5-carboxymethyluridine); $m^6Am$ ($N^6,2'$-O-dimethyladenosine); $m^6_2Am$ ($N^6,N^6,O-2'$-trimethyladenosine); $m^{2,7}G$ ($N^2,7$-dimethylguanosine); $m^{2,2,7}G$ ($N^2,N^2,7$-trimethylguanosine); $m^3Um$ (3,2'-O-dimethyluridine); $m^5D$ (5-methyldihydrouridine); $f^5Cm$ (5-formyl-2'-O-methylcytidine); $m^1Gm$ (1,2'-O-dimethylguanosine); $m^1Am$ (1,2'-O-dimethyladenosine); $τm^5U$ (5-taurinomethyluridine); $τm^5s^2U$ (5-taurinomethyl-2-thiouridine)); imG-14 (4-demethylwyosine); imG2 (isowyosine); or $ac^6A$ ($N^6$-acetyladenosine). Each possibility represents a separate embodiment of the present invention.

In another embodiment, an RNA, oligoribonucleotide, or polyribonucleotide molecule of methods and compositions of the present invention comprises a combination of 2 or more of the above modifications. In another embodiment, the RNA molecule or oligoribonucleotide molecule comprises a combination of 3 or more of the above modifications. In another embodiment, the RNA molecule or oligoribonucleotide molecule comprises a combination of more than 3 of the above modifications. Each possibility represents a separate embodiment of the present invention.

In another embodiment, between 0.1% and 100% of the residues in the RNA, oligoribonucleotide, or polyribonucleotide molecule of methods and compositions of the present invention are modified (e.g. either by the presence of pseudouridine or a modified nucleoside base). In another embodiment, 0.1% of the residues are modified. In another embodiment, 0.2%. In another embodiment, the fraction is 0.3%. In another embodiment, the fraction is 0.4%. In another embodiment, the fraction is 0.5%. In another embodiment, the fraction is 0.6%. In another embodiment, the fraction is 0.8%. In another embodiment, the fraction is 1%. In another embodiment, the fraction is 1.5%. In another embodiment, the fraction is 2%. In another embodiment, the fraction is 2.5%. In another embodiment, the fraction is 3%. In another embodiment, the fraction is 4%. In another embodiment, the fraction is 5%. In another embodiment, the fraction is 6%. In another embodiment, the fraction is 8%. In another embodiment, the fraction is 10%. In another embodiment, the fraction is 12%. In another embodiment, the fraction is 14%. In another embodiment, the fraction is 16%. In another embodiment, the fraction is 18%. In another embodiment, the fraction is 20%. In another embodiment, the fraction is 25%. In another embodiment, the fraction is 30%. In another embodiment, the fraction is 35%. In another embodiment, the fraction is 40%. In another embodiment, the fraction is 45%. In another embodiment, the fraction is 50%. In another embodiment, the fraction is 60%. In another embodiment, the fraction is 70%. In another embodiment, the fraction is 80%. In another embodiment, the fraction is 90%. In another embodiment, the fraction is 100%.

In another embodiment, the fraction is less than 5%. In another embodiment, the fraction is less than 3%. In another embodiment, the fraction is less than 1%. In another embodiment, the fraction is less than 2%. In another embodiment, the fraction is less than 4%. In another embodiment, the fraction is less than 6%. In another embodiment, the fraction is less than 8%. In another embodiment, the fraction is less than 10%. In another embodiment, the fraction is less than 12%. In another embodiment, the fraction is less than 15%. In another embodiment, the fraction is less than 20%. In another embodiment, the fraction is less than 30%. In another embodiment, the fraction is less than 40%. In another embodiment, the fraction is less than 50%. In another embodiment, the fraction is less than 60%. In another embodiment, the fraction is less than 70%.

In another embodiment, 0.1% of the residues of a given nucleotide (uridine, cytidine, guanosine, or adenine) are modified. In another embodiment, the fraction of the nucleotide is 0.2%. In another embodiment, the fraction is 0.3%. In another embodiment, the fraction is 0.4%. In another embodiment, the fraction is 0.5%. In another embodiment, the fraction is 0.6%. In another embodiment, the fraction is 0.8%. In another embodiment, the fraction is 1%. In another embodiment, the fraction is 1.5%. In another embodiment, the fraction is 2%. In another embodiment, the fraction is 2.5%. In another embodiment, the fraction is 3%. In another embodiment, the fraction is 4%. In another embodiment, the fraction is 5%. In another embodiment, the fraction is 6%. In another embodiment, the fraction is 8%. In another embodiment, the fraction is 10%. In another embodiment, the fraction is 12%. In another embodiment, the fraction is 14%. In another embodiment, the fraction is 16%. In another embodiment, the fraction is 18%. In another embodiment, the fraction is 20%. In another embodiment, the fraction is 25%. In another embodiment, the fraction is 30%. In another embodiment, the fraction is 35%. In another embodiment, the fraction is 40%. In another embodiment, the fraction is 45%. In another embodiment, the fraction is 50%. In another embodiment, the fraction is 60%. In another embodiment, the fraction is 70%. In another embodiment, the fraction is 80%. In another embodiment, the fraction is 90%. In another embodiment, the fraction is 100%.

In another embodiment, the fraction of the given nucleotide is less than 8%. In another embodiment, the fraction is less than 10%. In another embodiment, the fraction is less than 5%. In another embodiment, the fraction is less than 3%. In another embodiment, the fraction is less than 1%. In another embodiment, the fraction is less than 2%. In another embodiment, the fraction is less than 4%. In another embodiment, the fraction is less than 6%. In another embodiment, the fraction is less than 12%. In another embodiment, the fraction is less than 15%. In another embodiment, the fraction is less than 20%. In another embodiment, the fraction is less than 30%. In another embodiment, the fraction is less than 40%. In another embodiment, the fraction is less than 50%. In another embodiment, the fraction is less than 60%. In another embodiment, the fraction is less than 70%.

In another embodiment, the terms "ribonucleotide," "oligoribonucleotide," and "polyribonucleotide" refers to a string of at least 2 base-sugar-phosphate combinations. The term includes, in another embodiment, compounds comprising nucleotides in which the sugar moiety is ribose. In another embodiment, the term includes both RNA and RNA derivates in which the backbone is modified. "Nucleotides" refers, in another embodiment, to the monomeric units of nucleic acid polymers. RNA may be, in an other embodiment, in the form of a tRNA (transfer RNA), snRNA (small nuclear RNA), rRNA (ribosomal RNA), mRNA (messenger RNA), anti-sense RNA, small inhibitory RNA (siRNA), micro RNA (miRNA) and ribozymes. The use of siRNA and miRNA has been described (Caudy A A et al, Genes & Devel 16: 2491-96 and references cited therein). In addition, these forms of RNA may be single, double, triple, or quadruple stranded. The term also includes, in another embodiment, artificial nucleic acids that may contain other types of backbones but the same bases. In another embodiment, the artificial nucleic acid is a PNA (peptide nucleic acid). PNA contain peptide backbones and nucleotide bases and are able to bind, in another embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothioate nucleic acids and PNA are known to those skilled in the art, and are described in, for example, Neilsen P E, Curr Opin Struct Biol 9:353-57; and Raz N K et al Biochem Biophys Res Commun. 297:1075-84. The production and use of nucleic acids is known to those skilled in art and is described, for example, in Molecular Cloning, (2001), Sambrook and Russell, eds. and Methods in Enzymology: Methods for molecular cloning in eukaryotic cells (2003) Purchio and G. C. Fareed. Each nucleic acid derivative represents a separate embodiment of the present invention In another embodiment, the term "oligoribonucleotide" refers to a string comprising fewer than 25 nucleotides (nt). In another embodiment, "oligoribonucleotide" refers to a string of fewer than 24 nucleotides. In another embodiment, "oligoribonucleotide" refers to a string of fewer than 23 nucleotides. In another embodiment, "oligoribonucleotide" refers to a string of fewer than 22 nucleotides. In another embodiment, "oligoribonucleotide" refers to a string of fewer than 21 nucleotides. In another embodiment, "oligoribonucleotide" refers to a string of fewer than 20 nucleotides. In another embodiment, "oligoribonucleotide" refers to a string of fewer than 19 nucleotides. In another embodiment, "oligoribonucleotide" refers to a string of fewer than 18 nucleotides. In another embodiment, "oligoribonucleotide" refers to a string of fewer than 17 nucleotides. In another embodiment, "oligoribonucleotide" refers to a string of fewer than 16 nucleotides. Each possibility represents a separate embodiment of the present invention.

In another embodiment, the term "polyribonucleotide" refers to a string comprising more than 25 nucleotides (nt). In another embodiment, "polyribonucleotide" refers to a string of more than 26 nucleotides. In another embodiment, "polyribonucleotide" refers to a string of more than 28 nucleotides. In another embodiment, "the term" refers to a string of more than 30 nucleotides. In another embodiment, "the term" refers to a string of more than 32 nucleotides. In another embodiment, "the term" refers to a string of more than 35 nucleotides. In another embodiment, "the term" refers to a string of more than 40 nucleotides. In another embodiment, "the term" refers to a string of more than 50 nucleotides. In another embodiment, "the term" refers to a string of more than 60 nucleotides. In another embodiment, "the term" refers to a string of more than 80 nucleotides. In another embodiment, "the term" refers to a string of more than 100 nucleotides. In another embodiment, "the term" refers to a string of more than 120 nucleotides. In another embodiment, "the term" refers to a string of more than 150 nucleotides. In another embodiment, "the term" refers to a string of more than 200 nucleotides. In another embodiment, "the term" refers to a string of more than 300 nucleotides. In another embodiment, "the term" refers to a string of more than 400 nucleotides. In another embodiment, "the term" refers to a string of more than 500 nucleotides. In another embodiment, "the term" refers to a string of more than 600 nucleotides. In another embodiment, "the term" refers to a string of more than 800 nucleotides. In another embodiment, "the term" refers to a string of more than 1000 nucleotides. In another embodiment, "the term" refers to a string of more than 1200 nucleotides. In another embodiment, "the term" refers to a string of more than 1400 nucleotides. In another embodiment, "the term" refers to a string of more than 1600 nucleotides. In another embodiment, "the term" refers to a string of more than 1800 nucleotides. In another embodiment, "the term" refers to a string of more than 2000 nucleotides. Each possibility represents a separate embodiment of the present invention.

In another embodiment, the present invention provides a method for inducing a mammalian cell to produce a protein of interest, comprising contacting the mammalian cell with an in vitro-synthesized RNA molecule encoding the recombinant protein, the in vitro-synthesized RNA molecule comprising a pseudouridine or a modified nucleoside, thereby inducing a mammalian cell to produce a protein of interest. In another embodiment, the protein of interest is a recombinant protein. Each possibility represents a separate embodiment of the present invention.

"Encoding" refers, in another embodiment, to an RNA molecule that contains a gene that encodes the protein of interest. In another embodiment, the RNA molecule comprises an open reading frame that encodes the protein of interest. In another embodiment, 1 or more other proteins is also encoded. In another embodiment, the protein of interest is the only protein encoded. Each possibility represents a separate embodiment of the present invention.

In another embodiment, the present invention provides a method of inducing a mammalian cell to produce a recombinant protein, comprising contacting the mammalian cell with an in vitro-transcribed RNA molecule encoding the recombinant protein, the in vitro-transcribed RNA molecule further comprising a pseudouridine or a modified nucleoside, thereby inducing a mammalian cell to produce a recombinant protein.

In another embodiment, an RNA, oligoribonucleotide, or polyribonucleotide molecule of methods and compositions of the present invention is translated in the cell more efficiently than an unmodified RNA molecule with the same sequence. In another embodiment, the RNA, oligoribonucleotide, or polyribonucleotide molecule exhibits enhanced ability to be translated by a target cell. In another embodiment, translation is enhanced by a factor of 2-fold relative to its unmodified counterpart. In another embodiment, translation is enhanced by a 3-fold factor. In another embodiment, translation is enhanced by a 5-fold factor. In another embodiment, translation is enhanced by a 7-fold factor. In another embodiment, translation is enhanced by a 10-fold factor. In another embodiment, translation is enhanced by a 15-fold factor. In another embodiment, translation is enhanced by a 20-fold factor. In another embodiment, translation is enhanced by a 50-fold factor. In another embodiment, translation is enhanced by a 100-fold factor. In another embodiment, translation is enhanced by a 200-fold factor. In another embodiment, translation is enhanced by a 500-fold factor. In another embodiment, translation is enhanced by a 1000-fold factor. In another embodiment, translation is enhanced by a 2000-fold factor. In another embodiment, the factor is 10-1000-fold. In another embodiment, the factor is 10-100-fold. In another embodiment, the factor is 10-200-fold. In another embodiment, the factor is 10-300-fold. In another embodiment, the factor is 10-500-fold. In another embodiment, the factor is 20-1000-fold. In another embodiment, the factor is 30-1000-fold. In another embodiment, the factor is 50-1000-fold. In another embodiment, the factor is 100-1000-fold. In another embodiment, the factor is 200-1000-fold. In another embodiment, translation is enhanced by any other significant amount or range of amounts. Each possibility represents a separate embodiment of the present invention.

Methods of determining translation efficiency are well known in the art, and include, e.g. measuring the activity of an encoded reporter protein (e.g luciferase or *renilla* [Examples herein] or green fluorescent protein [Wall A A, Phillips A M et al, Effective translation of the second cistron in two *Drosophila* dicistronic transcripts is determined by the absence of in-frame AUG codons in the first cistron. J Biol Chem 2005; 280(30): 27670-8]), or measuring radioactive label incorporated into the translated protein (Ngosuwan J, Wang N M et al, Roles of cytosolic Hsp70 and Hsp40 molecular chaperones in post-translational translocation of presecretory proteins into the endoplasmic reticulum. J Biol Chem 2003; 278(9): 7034-42). Each method represents a separate embodiment of the present invention.

Figure 12A:
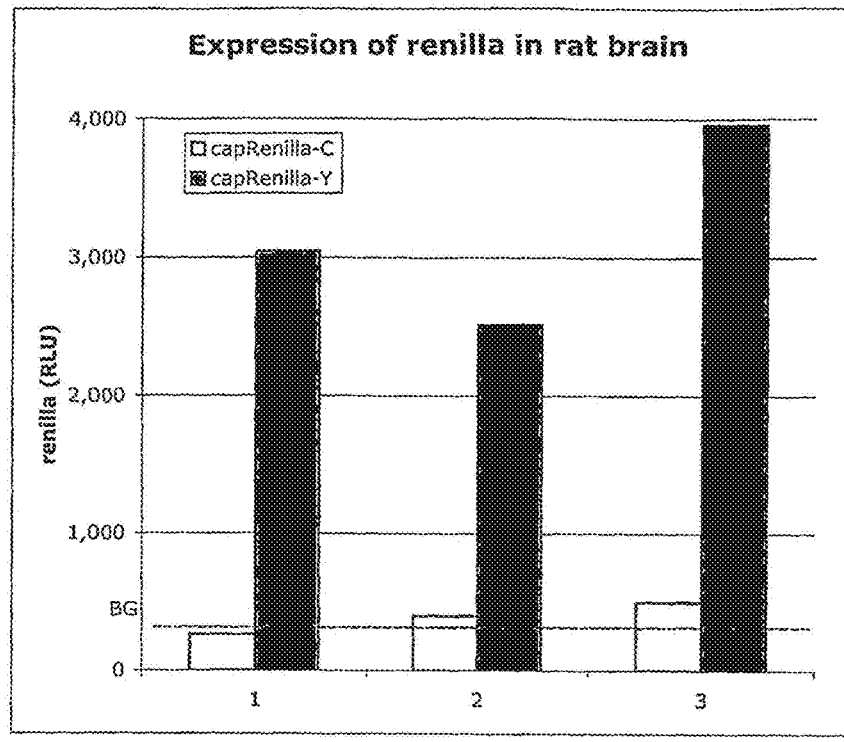
FIG. 12A. Expression of renilla following intracerebral injection of modified or unmodified encoding mRNA. Rat brain cortex was injected at 8 sites/animals. One hemisphere was injected with capped, renilla-encoding RNA with pseudouridine modification (capRenilla-Y), while the corresponding hemisphere with capped RNA with no nucleoside modification (capRenilla-C). Data from 2 animals (6 injection sites) are shown. BG; lower level of detection of the assay.
Figure 12B:
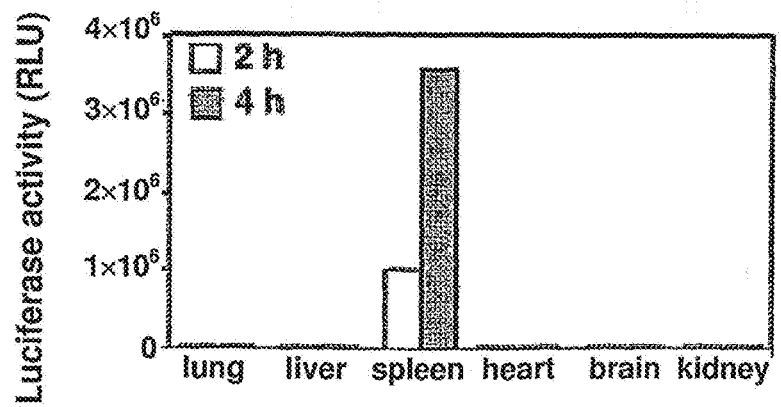
FIG. 12B. Intravenous ψmRNA is expressed in spleen. Lipofectin-complexed ψmRNA (0.3 μg capTEVlucAn/mouse) was administered by tail vein injection. Animals were sacrificed at 2 and 4 h post-injection and luciferase activities measured in aliquots (1/10th) of organs homogenized in lysis buffer. Values represent luciferase activities in the whole organs. Expression of renilla following i.v. injection of mRNA into mouse tail vein. Data from two independently performed experiments are depicted in the left and right panels. Spleens were harvested and homogenized, and renilla activity was measured in aliquots of the lysates.

In expression studies provided herein, translation was measured from RNA complexed to Lipofectin® (Gibco BRL, Gaithersburg, Md., USA) and injected into the tail vein of mice. In the spleen lysates, pseudouridine-modified RNA was translated significantly more efficiently than unmodified RNA (FIG. 12B). Under the conditions utilized herein, efficiency of transfection-based methods of the present invention correlates with the ability of the transfection reagent to penetrate into tissues, providing an explanation for why the effect was most pronounced in spleen cells. Splenic blood flow is an open system, with blood contents directly contacting red and white pulp elements including lymphoid cells.

In another experiment, in vitro phosphorylation assays were performed using recombinant human PKR and its substrate, eIF2α in the presence of capped, *renilla*-encoding mRNA (0.5 and 0.05 ng/μl). mRNA containing pseudouridine (Ψ) did not activate PKR, as detected by lack of both self-phosphorylation of PKR and phosphorylation of eIF2α, while RNA without nucleoside modification and mRNA with m5C modification activated PKR. Phosphorylated eIF2α is known to block initiation of mRNA translation, therefore lack of phosphorylation enables, in another embodiment, enhanced translation of the mRNA containing pseudouridine (Ψ).

In another embodiment, the enhanced translation is in a cell (relative to translation in the same cell of an unmodified RNA molecule with the same sequence; Examples 10-11). In another embodiment, the enhanced translation is in vitro (e.g. in an in vitro translation mix or a reticulocyte lysate; Examples 10-11. In another embodiment, the enhanced translation is in vivo (Example 13). In each case, the enhanced translation is relative to an unmodified RNA molecule with the same sequence, under the same conditions. Each possibility represents a separate embodiment of the present invention.

In another embodiment, the RNA, oligoribonucleotide, or polyribonucleotide molecule of methods and compositions of the present invention is significantly less immunogenic than an unmodified in vitro-synthesized RNA molecule with the same sequence. In another embodiment, the modified RNA molecule is 2-fold less immunogenic than its unmodified counterpart. In another embodiment, immunogenicity is reduced by a 3-fold factor. In another embodiment, immunogenicity is reduced by a 5-fold factor. In another embodiment, immunogenicity is reduced by a 7-fold factor. In another embodiment, immunogenicity is reduced by a 10-fold factor. In another embodiment, immunogenicity is reduced by a 15-fold factor. In another embodiment, immunogenicity is reduced by a 20-fold factor. In another embodiment, immunogenicity is reduced by a 50-fold factor. In another embodiment, immunogenicity is reduced by a 100-fold factor. In another embodiment, immunogenicity is reduced by a 200-fold factor. In another embodiment, immunogenicity is reduced by a 500-fold factor. In another embodiment, immunogenicity is reduced by a 1000-fold factor. In another embodiment, immunogenicity is reduced by a 2000-fold factor. In another embodiment, immunogenicity is reduced by another fold difference.

In another embodiment, "significantly less immunogenic" refers to a detectable decrease in immunogenicity. In another embodiment, the term refers to a fold decrease in immunogenicity (e.g. 1 of the fold decreases enumerated above). In another embodiment, the term refers to a decrease such that an effective amount of the RNA, oligoribonucleotide, or polyribonucleotide molecule can be administered without triggering a detectable immune response. In another embodiment, the term refers to a decrease such that the RNA, oligoribonucleotide, or polyribonucleotide molecule can be repeatedly administered without eliciting an immune response sufficient to detectably reduce expression of the recombinant protein. In another embodiment, the decrease is such that the RNA, oligoribonucleotide, or polyribonucleotide molecule can be repeatedly administered without eliciting an immune response sufficient to eliminate detectable expression of the recombinant protein.

"Effective amount" of the RNA, oligoribonucleotide, or polyribonucleotide molecule refers, in another embodiment, to an amount sufficient to exert a therapeutic effect. In another embodiment, the term refers to an amount sufficient to elicit expression of a detectable amount of the recombinant protein. Each possibility represents a separate embodiment of the present invention.

Reduced immunogenicity of RNA, oligoribonucleotide, and polyribonucleotide molecules of the present invention is demonstrated herein (Examples 1-8).

Methods of determining immunogenicity are well known in the art, and include, e.g. measuring secretion of cytokines (e.g. IL-12, IFN-α, TNF-α, RANTES, MIP-1α or β, IL-6, IFN-β, or IL-8. Examples herein), measuring expression of DC activation markers (e.g. CD83, HLA-DR, CD80 and CD86; Examples herein), or measuring ability to act as an adjuvant for an adaptive immune response. Each method represents a separate embodiment of the present invention.

In another embodiment, the relative immunogenicity of the modified nucleotide and its unmodified counterpart are determined by determining the quantity of the modified nucleotide required to elicit one of the above responses to the same degree as a given quantity of the unmodified nucleotide. For example, if twice as much modified nucleotide is required to elicit the same response, than the modified nucleotide is two-fold less immunogenic than the unmodified nucleotide.

In another embodiment, the relative immunogenicity of the modified nucleotide and its unmodified counterpart are determined by determining the quantity of cytokine (e.g. IL-12, IFN-α, TNF-α, RANTES, MIP-1α or 3, IL-6, IFN-β, or IL-8) secreted in response to administration of the modified nucleotide, relative to the same quantity of the unmodified nucleotide. For example, if one-half as much cytokine is secreted, than the modified nucleotide is two-fold less immunogenic than the unmodified nucleotide. In another embodiment, background levels of stimulation are subtracted before calculating the immunogenicity in the above methods. Each possibility represents a separate embodiment of the present invention.

In another embodiment, a method of present invention further comprises mixing the RNA, oligoribonucleotide, or polyribonucleotide molecule with a transfection reagent prior to the step of contacting. In another embodiment, a method of present invention further comprises administering the RNA, oligoribonucleotide, or polyribonucleotide molecule together with the transfection reagent. In another embodiment, the transfection reagent is a cationic lipid reagent (Example 3).

In another embodiment, the transfection reagent is a lipid-based transfection reagent. In another embodiment, the transfection reagent is a protein-based transfection reagent. In another embodiment, the transfection reagent is a polyethyleneimine based transfection reagent. In another embodiment, the transfection reagent is calcium phosphate. In another embodiment, the transfection reagent is Lipofectin® or Lipofectamine®. In another embodiment, the transfection reagent is any other transfection reagent known in the art.

In another embodiment, the transfection reagent forms a liposome. Liposomes, in another embodiment, increase intracellular stability, increase uptake efficiency and improve biological activity. In another embodiment, liposomes are hollow spherical vesicles composed of lipids arranged in a similar fashion as those lipids which make up the cell membrane. They have, in another embodiment, an internal aqueous space for entrapping water soluble compounds and range in size from 0.05 to several microns in diameter. In another embodiment, liposomes can deliver RNA to cells in a biologically active form.

Each type of transfection reagent represents a separate embodiment of the present invention.

In another embodiment, the target cell of methods of the present invention is an antigen-presenting cell. In another embodiment, the cell is an animal cell. In another embodiment, the cell is a dendritic cell (Example 11). In another embodiment, the cell is a neural cell. In another embodiment, the cell is a brain cell (Example 13). In another embodiment, the cell is a spleen cell. In another embodiment, the cell is a lymphoid cell. In another embodiment, the cell is a lung cell (Example 13). In another embodiment, the cell is a skin cell. In another embodiment, the cell is a keratinocyte. In another embodiment, the cell is an endothelial cell. In another embodiment, the cell is an astrocyte, a microglial cell, or a neuron (Example 13). In another embodiment, the cell is an alveolar cell (Example 13). In another embodiment, the cell is a surface alveolar cell (Example 13). In another embodiment, the cell is an alveolar macrophage. In another embodiment, the cell is an alveolar pneumocyte. In another embodiment, the cell is a vascular endothelial cell. In another embodiment, the cell is a mesenchymal cell. In another embodiment, the cell is an epithelial cell. In another embodiment, the cell is a hematopoietic cell. In another embodiment, the cell is colonic epithelium cell. In another embodiment, the cell is a lung epithelium cell. In another embodiment, the cell is a bone marrow cell.

In other embodiments, the target cell is a Claudius' cell, Hensen cell, Merkel cell, Müller cell, Paneth cell, Purkinje cell, Schwann cell, Sertoli cell, acidophil cell, acinar cell, adipoblast, adipocyte, brown or white alpha cell, amacrine cell, beta cell, capsular cell, cementocyte, chief cell, chondroblast, chondrocyte, chromaffin cell, chromophobic cell, corticotroph, delta cell, Langerhans cell, follicular dendritic cell, enterochromaffin cell, ependymocyte, epithelial cell, basal cell, squamous cell, endothelial cell, transitional cell, erythroblast, erythrocyte, fibroblast, fibrocyte, follicular cell, germ cell, gamete, ovum, spermatozoon, oocyte, primary oocyte, secondary oocyte, spermatid, spermatocyte, primary spermatocyte, secondary spermatocyte, germinal epithelium, giant cell, glial cell, astroblast, astrocyte, oligodendroblast, oligodendrocyte, glioblast, goblet cell, gonadotroph, granulosa cell, haemocytoblast, hair cell, hepatoblast, hepatocyte, hyalocyte, interstitial cell, juxtaglomerular cell, keratinocyte, keratocyte, lemmal cell, leukocyte, granulocyte, basophil, eosinophil, neutrophil, lymphoblast, B-lymphoblast, T-lymphoblast, lymphocyte, B-lymphocyte, T-lymphocyte, helper induced T-lymphocyte, Th1 T-lymphocyte, Th2 T-lymphocyte, natural killer cell, thymocyte, macrophage, Kupffer cell, alveolar macrophage, foam cell, histiocyte, luteal cell, lymphocytic stem cell, lymphoid cell, lymphoid stem cell, macroglial cell, mammotroph, mast cell, medulloblast, megakaryoblast, megakaryocyte, melanoblast, melanocyte, mesangial cell, mesothelial cell, metamyelocyte, monoblast, monocyte, mucous neck cell, muscle cell, cardiac muscle cell, skeletal muscle cell, smooth muscle cell, myelocyte, myeloid cell, myeloid stem cell, myoblast, myoepithelial cell, myofibrobast, neuroblast, neuroepithelial cell, neuron, odontoblast, osteoblast, osteoclast, osteocyte, oxyntic cell, parafollicular cell, paralutteal cell, peptic cell, pericyte, peripheral blood mononuclear cell, phaeochromocyte, phalangeal cell, pinealocyte, pituicyte, plasma cell, platelet, podocyte, proerythroblast, promonocyte, promyeloblast, promyclocyte, pronormoblast, reticulocyte, retinal pigment epithelial cell, retinoblast, small cell, somatotroph, stem cell, sustentacular cell, teloglial cell, or zymogenic cell. Each possibility represents a separate embodiment of the present invention.

A variety of disorders may be treated by employing methods of the present invention including, inter alia, monogenic disorders, infectious diseases, acquired disorders, cancer, and the like. Exemplary monogenic disorders include ADA deficiency, cystic fibrosis, familial-hypercholesterolemia, hemophilia, chronic ganulomatous disease, Duchenne muscular dystrophy, Fanconi anemia, sickle-cell anemia, Gaucher's disease, Hunter syndrome, X-linked SCID, and the like. In another embodiment, the disorder treated involves one of the proteins listed below. Each possibility represents a separate embodiment of the present invention.

In another embodiment, the recombinant protein encoded by an RNA, oligoribonucleotide, or polyribonucleotide molecule of methods and compositions of the present invention is ecto-nucleoside triphosphate diphosphohydrolase.

In another embodiment, the recombinant protein is erythropoietin (EPO).

In other embodiments, the encoded recombinant protein is ABCA4; ABCD3; ACADM; AGL; AGT; ALDH4A1; ALPL; AMPD1; APOA2; AVSD1; BRCD2; C1QA; C1QB; C1QG; C8A; C8B; CACNA1S; CCV; CD3Z; CDC2L1; CHML; CHS1; CIAS1; CLCNKB; CMD1A; CMH2: CMM; COL11A1; COL8A2; COL9A2; CPT2; CRB1; CSE; CSF3R; CTPA; CTSK; DBT; DIO1; DISC1; DPYD; EKV; ENO1; ENO1P; EPB41; EPHX1; F13B; F5; FCGR2A; FCGR2B; FCGR3A; FCHL; FH; FMO3; FMO4; FUCA1; FY; GALE; GBA; GFND. GJA8; GJB3; GLC3B; HF1; HMGCL; HPC1; HRD; HRPT2; HSD3B2; HSPG2; KCNQ4; KCS; KIF1B; LAMB3. LAMC2; LGMD1B; LMNA; LOR; MCKD1; MCL1; MPZ; MTHFR; MTR; MUTYH; MYOC; NB; NCF2; NEM1; NPHS2; NPPA; NRAS; NTRK1; OPTA2; PBX1; PCHC; PGD; PHA2A; PHGDH; PKLR; PKP1; PLA2G2A PLOD; PPOX; PPT1; PRCC; PRG4; PSEN2; PTOS1; REN; RFX5; RHD; RMD1; RPE65; SCCD; SERPINC1; SJS1; SLC19A2; SLC2A1; SPG23; SPTA1; TAL1; TNFSF6; TNNT2; TPM3; TSHB; UMPK; UOX; UROD; USH2A; VMGLOM; VWS; WS2B; ABCB11; ABCG5; ABCG8; ACADL; ACP1; AGXT; AHHR; ALMS1; ALPP; ALS2; APOB; BDE; BDMR; BJS; BMPR2; CHRNA1; CMCWTD; CNGA3; COL3A1; COL4A3; COL4A4; COL6A3; CPS1; CRYGA; CRYGEP1; CYP1B1; CYP27A1; DBI; DES; DYSF; EDAR; EFEMP1; EIF2AK3; ERCC3; FSHR; GINGF; GLC1B; GPD2; GYPC; HADHA; HADHB; HOXD13; HPE2; IGKC; IHH; IRS1; ITGA6; KHK; KYNU; LCT; LHCGR; LSFC; MSH2; MSH6 NEB; NMTC; NPHP1; PAFAH1P1; PAX3; PAX8; PMS1; PNKD; PPH1; PROC; REG1A; SAG; SFTPB; SLC11A1; SLC3A1; SOS1; SPG4; SRD5A2; TCL4 TGFA; TMD; TPO; UGT1A@; UV24; WSS; XDH; ZAP70; ZFHX1B; ACAA1; AGS1; AGTR1; AHSG; AMT; ARMET; BBS3; BCHE; BCPM; BTD; CASR; CCR2; CCR5; CDL1; CMT2B; COL7A1; CP; CPO; CRV; CTNNB; DEM; ETM1; FANCD2; FIH; FOXL2; GBE1; GLB1; GLC1C; GNAI2; GNAT1; GP9; GPX1; HGD; HRG; ITIH1; KNG; LPP; LRS1; MCCC1; MDS1; MHS4; MITF; MLH1; MYL3; MYMY; OPA1; P2RY12; PBXP1; PCCB; POU1F1; PPARG; PROS1; PTHR1; RCA1; RHO; SCA7; SCLC1; SCN5A; SI; SLC25A20; SLC2A2; TF; TGFBR2; THPO; THRB; TKT; TM4SF1; TRH; UMPS; UQCRC1; USH3A; VHL; WS2A; XPC; ZNF35; ADH1B; ADH1C; AFP; AGA; AIH2; ALB; ASMD; BFHD; CNGA1; CRBM; DCK; DSPP; DTDP2; ELONG; ENAM; ETFDH; EVC; F11; FABP2; FGA; FGB; FGFR3; FGG; FSHMD1A; GC; GNPTA; GNRHR; GYPA; HCA; HCL2; HD; HTN3; HVBS6; IDUA; IF; JPD; KIT; KLKB1; LQT4; MANBA; MLLT2; MSX1; MTP; NR3C2; PBT; PDE6B; PEE1; PITX2; PKD2; QDPR; SGCB; SLC25A4; SNCA; SOD3; STATH; TAPVR1; TYS; WBS2; WFS1; WHCR; ADAMTS2; ADRB2; AMCN; AP3B1; APC; ARSB; B4GALT7; BHR1; C6; C7; CCAL2; CKN1; CMDJ; CRHBP; CSF1R; DHFR; DIAPH1; DTR; EOS; EPD: ERVR; F12; FBN2; GDNF; GHR; GLRA1; GM2A; HEXB; HSD17B4; ITGA2; KFS; LGMD1A; LOX; LTC4S; MAN2A1; MCC; MCCC2; MSH3; MSX2; NR3C1; PCSK1; PDE6A; PFB1; RASA1; SCZD1; SDHA; SGCD; SLC22A5; SLC26A2; SLC6A3; SM1; SMA@; SMN1; SMN2; SPINK5; TCOF1; TELAB1; TGFB1; ALDH5A1; ARG1; AS; ASSP2; BCKDHB; BF; C2; C4A; CDKN1A; COL10A1; COL11A2; CYP21A2; DYX2; EJM1; ELOVL4; EPM2A; ESR1; EYA4; F13A1; FANCE; GCLC; GJA1; GLYS1; GMPR; GSE; HCR; HFE; HLA-A; HLA-DPB1; HLA-DRA; HPFH; ICS1; IDDM1; IFNGR1; IGAD1; IGF2R; ISCW; LAMA2; LAP; LCA5; LPA; MCDR1; MOCS1; MUT; MYB; NEU1; NKS1; NYS2; OA3; ODDD; OFC1; PARK2; PBCA; PBCRA1; PDB1; PEX3; PEX6; PEX7; PKHD1; PLA2G7; PLG; POLH; PPAC; PSORS1; PUJO; RCD1; RDS; RHAG; RP14; RUNX2; RWS; SCA1; SCZD3; SIASD; SOD2; ST8; TAP1; TAP2; TFAP2B; TNDM; TNF: TPBG; TPMT; TULP1; WISP3; AASS; ABCB1; ABCB4; ACHE; AQP1; ASL; ASNS; AUTS1; BPGM; BRAF; C7orf2; CACNA2D1; CCM1; CD36; CFTR; CHORDOMA; CLCN1; CMH6; CMT2D; COL1A2; CRS; CYMD; DFNA5; DLD; DYT11; EEC1; ELN; ETV1; FKBP6; GCK; GHRHR; GHS; GLI3; GPDS1; GUSB; HLXB9; HOXA13; HPFH2; HRX; IAB; IMMP2L; KCNH2; LAMB1; LEP; MET; NCF1; NM; OGDH; OPN1SW; PEX1; PGAM2; PMS2; PON1; PPP1R3A; PRSS1; PTC; PTPN12; RP10; RP9; SERPINE1; SGCE; SHFM1; SHH; SLC26A3; SLC26A4; SLOS; SMAD1; TBXAS1; TWIST; ZWS1; ACHM3; ADRB3; ANK1; CA1; CA2; CCAL1; CLN8; CMT4A; CNGB3; COH1; CPP; CRH; CYP11B1; CYP11B2; DECR1; DPYS; DURS1; EBS1; ECA1; EG1; EXT1; EYA1; FGFR1; GNRH1; GSR; GULOP; HR; KCNQ3; KFM; KWE; LGCR; LPL; MCPH1; MOS; MYC; NAT1; NAT2; NBS1; PLAT; PLEC1; PRKDC; PXMP3; RP1; SCZD6; SFTPC; SGM1; SPG5A; STAR; TG; TRPS1; TTPA; VMD1; WRN: ABCA1; ABL1; ABO; ADAMTS13; AK1; ALAD; ALDH1A1; ALDOB; AMBP; AMCD1; ASS; BDMF; BSCL; C5; CDKN2A; CHAC; CLA; CMD1B; COL5A1; CRAT; DBH; DNAI1; DYS; DYT1; ENG; FANCC; FBP1; FCMD; FRDA; GALT; GLDC; GNE; GSM1; GSN; HSD17B3; HSN1; IBM2; INVS; JBTS1; LALL; LCCS1; LCCS; LGMD2H; LMX1B; MLLT3; MROS; MSSE; NOTCH1; ORM1; PAPPA; PIP5K1B; PTCH; PTGS1; RLN1; RLN2; RMRP; ROR2; RPD1; SARDH; SPTLC1; STOM; TDFA; TEK; TMC1; TRIM32; TSC1; TYRP1; XPA; CACNB2; COL17A1; CUBN; CXCL12; CYP17; CYP2C19; CYP2C9; EGR2; EMX2; ERCC6; FGFR2; HK1; HPS1; IL2RA; LGI1; LIPA; MAT1A; MBL2; MKI67; MXI1; NODAL; OAT; OATL3; PAX2; PCBD; PEO1; PHYH; PNLIP; PSAP; PTEN; RBP4; RDPA; RET;

SFTPA1; SFTPD; SHFM3; SIAL; THC2; TLX1; TNFRSF6; UFS; UROS; AA; ABCC8; ACAT1; ALX4; AMPD3; ANC; APOA1; APOA4; APOC3; ATM; BSCL2; BWS; CALCA; CAT; CCND1; CD3E; CD3G; CD59; CDKN1C; CLN2; CNTF; CPTIA; CTSC; DDB1; DDB2; DHCR7; DLAT; DRD4; ECB2; ED4; EVR1; EXT2; F2; FSHB; FTH1; G6PT1; G6PT2; GIF; HBB; HBBP1; HBD; HBE1; HBG1; HBG2; HMBS; HND; HOMG2; HRAS; HVBS1; IDDM2; IGER; INS; JBS; KCNJ11; KCNJ1; KCNQ1; LDHA; LRP5; MEN1; MLL; MYBPC3; MYO7A; NNO1; OPPG; OPTB1; PAX6; PC; PDX1; PGL2; PGR; PORC; PTH; PTS; PVRL1; PYGM; RAG1; RAG2; ROM1; RRAS2; SAA1; SCA5; SCZD2; SDHD; SERPING1; SMPD1; TCIRG1; TCL2; TECTA; TH; TREH; TSG101; TYR; USH1C; VMD2; VRN1; WT1; WT2; ZNF145; A2M; AAAS; ACADS; ACLS; ACVRL1; ALDH2; AMHR2; AOM; AQP2; ATD; ATP2A2; BDC; C1R; CD4; CDK4; CNA1; COL2A1; CYP27B1; DRPLA; ENUR2; FEOM1; FGF23; FPF; GNB3; GNS; HAL; HBP1; HMGA2; HMN2; HPD; IGF1; KCNA1; KERA; KRAS2; KRT1; KRT2A; KRT3; KRT4; KRT5; KRT6A; KRT6B; KRTHB6; LDHB; LYZ; MGCT; MPE; MVK; MYL2; OAP; PAH; PPKB; PRB3; PTPN11; PXR1; RLS; RSN; SAS; SAX1; SCA2; SCNN1A; SMAL; SPPM; SPSMA; TBX3; TBX5; TCF1; TPI1; TSC3; ULR; VDR; VWF; ATP7B; BRCA2; BRCD1; CLN5; CPB2; ED2; EDNRB; ENUR1; ERCC5; F10; F7; GJB2; GJB6; IPF1; MBS1; MCOR; NYS4; PCCA; RB1; RHOK; SCZD7; SGCG; SLCIOA2; SLC25AI5; STARP1; ZNF198; ACHM1; ARVD1; BCH; CTAA1; DAD1; DFNB5; EML1; GALC; GCH1; IBGC1; IGH@; IGHC group; IGHG1; IGHM; IGHR; IV; LTBP2; MCOP; MJD; MNG1; MPD1; MPS3C; MYH6; MYH7; NP; NPC2; PABPN1; PSEN1; PYGL; RPGRIP1; SERPINA1; SERPINA3; SERPINA6; SLC7A7; SPG3A; SPTB; TCL1A; TGM1; TITF1; TMIP; TRA@; TSHR; USH1A; VP; ACCPN; AHO2; ANCR; B2M; BBS4; BLM; CAPN3; CDAN1; CDAN3; CLN6; CMH3; CYP19; CYP1A1; CYP1A2; DYX1; EPB42; ETFA; EYCL3; FAH; FBN1; FES; HCVS; HEXA; IVD; LCS1; LIPC; MYOSA; OCA2; OTSC1; PWCR; RLBP1; SLC12A1; SPG6; TPM1; UBE3A; WMS; ABCC6; ALDOA; APRT; ATP2A1; BBS2; CARDI5; CATM; CDH1; CETP; CHST6; CLN3; CREBBP; CTH; CTM; CYBA; CYLD; DHS; DNASE1; DPEP1; ERCC4; FANCA; GALNS; GAN; HAGH; HBA1; HBA2; HBHR; HBQ1; HBZ; HBZP; HP; HSD11B2; IL4R; LIPB; MC1R; MEFV; MHC2TA; MLYCD; MMVP1; PHKB; PHKG2; PKD1; PKDTS; PMM2; PXE; SALL1; SCA4; SCNN1B; SCNN1G; SLC12A3; TAT; TSC2; VD1; WT3; ABR; ACACA; ACADVL; ACE; ALDH3A2; APOH; ASPA; AXIN2; BCL5; BHD; BLMH; BRCA1; CACD; CCA1; CCZS; CHRNB1; CHRNE; CMT1A; COL1A1; CORD5; CTNS; EPX; ERBB2; G6PC; GAA; GALK; GCGR; GFAP; GH1; GH2; GPIBA; GPSC; GUCY2D; ITGA2B; ITGB3; ITGB4; KRT10; KRT12; KRT13 KRT14; KRT14L1; KRT14L2; KRT14L3; KRT16; KRT16L1; KRT16L2; KRT17; KRT9; MAPT; MDB; MDCR; MG1; MHS2; MKS1; MPO; MYO15A; NAGLU; NAPB; NF1; NME1; P4HB; PAFAH1B1; PECAM1; PEX12; PHB; PMP22; PRKAR1A; PRKCA; PRKWNK4; PRP8; PRPF8; PTLAH; RARA; RCV1; RMSA1; RP17; RSS; SCN4A; SERPINF2; SGCA; SGSH; SHBG; SLC2A4; SLC4A1; SLC6A4; SMCR; SOST; SOX9; SSTR2; SYM1; SYNS1; TCF2; THRA; TIMP2; TOC; TOP2A; TP53; TRIM37; VBCH; ATP8B1; BCL2; CNSN; CORD1; CYB5; DCC; F5F8D; FECH; FEO; LAMA3; LCFS2; MADH4; MAFD1; MC2R; MCL; MYP2; NPC1; SPPK; TGFBRE; TGIF; TTR; AD2; AMH; APOC2; APOE; ATHS; BAX; BCKDHA; BCL3; BFIC; C3; CACNA1A; CCO; CEACAM5; COMP; CRX; DBA; DDU; DFNA4; DLL3; DM1; DMWD; EllS; ELA2; EPOR; ERCC2; ETFB; EXT3; EYCL1; FTL; FUT1; FUT2; FUT6; GAMT; GCDH; GP1; GUSM; HB1; HCL1; HHC2; HHC3; ICAM3; INSR; JAK3; KLK3; LDLR; LHB; LIG1; LOH19CR1; LYL1; MAN2B1; MCOLN1; MDRV; MLLT1; NOTCH3; NPHS1; OFC3; OPA3; PEPD; PRPF31; PRTN3; PRX; PSG1; PVR; RYR1; SLC5A5; SLC7A9; STK11; TBXA2R; TGFB1; TNNI3; TYROBP; ADA; AHCY; AVP; CDAN2; CDPD1; CHED1; CHED2; CHRNA4; CST3; EDN3; EEGV1; FTLL1; GDF5; GNAS; GSS; HNF4A; JAG1; KCNQ2; MKKS; NBIA1; PCK1; PI3; PPCD; PPGB; PRNP; THBD; TOP1; AIRE; APP; CBS; COL6A1; COL6A2; CSTB; DCR; DSCR1; FPDMM; HLCS; HPE1; ITGB2; KCNE1; KNO; PRSS7; RUNX1; SOD1; TAM; ADSL; ARSA; BCR; CECR; CHEK2; COMT; CRYBB2; CSF2RB; CTHM; CYP2D6; CYP2D7P1; DGCR; DIA1; EWSR1; GGT1; MGCR; MN1; NAGA; NF2; OGS2; PDGFB; PPARA; PRODH; SCO2; SCZD4; SERPIND1; SLC5A1; SOX10; TCN2; TIMP3; TST; VCF; ABCD1; ACTL1; ADFN; AGMX2; AHDS; AIC; AIED; AIH3; ALAS2; AMCD; AMELX; ANOP1; AR; ARAF1; ARSC2; ARSE; ARTS; ARX; ASAT; ASSP5; ATP7A; ATRX; AVPR2; BFLS; BGN; BTK; BZX; C1HR; CACNAIF; CALB3; CBBM; CCT; CDR1; CFNS; CGF1; CHM; CHR39C; CIDX; CLA2; CLCN5; CLS; CMTX2; CMTX3; CND; COD1; COD2; COL4A5; COL4A6; CPX; CVD1; CYBB; DCX; DFN2; DFN4; DFN6; DHOF; DIAPH2; DKC1; DMD; DSS; DYT3; EBM; EBP; ED1; ELK1; EMD; EVR2; F8; F9; FCP1; FDPSL5; FGD1; FGS1; FMR1; FMR2; G6PD; GABRA3; GATA1; GDI1; GDXY; GJB1; GK; GLA; GPC3; GRPR; GTD; GUST; HMS1; HPRT1; HPT; HTC2; HTR2C; HYR; IDS; IHG1; IL2RG; INDX; IP1; IP2; JMS; KAL1; KFSD; LICAM; LAMP2; MAA; MAFD2; MAOA; MAOB; MCF2; MCS; MEAX; MECP2; MF4; MGC1; MIC5; MID1; MLLT7; MLS; MRSD; MRX14; MRX1; MRX20; MRX2; MRX3; MRX40; MRXA; MSD; MTM1; MYCL2; MYP1; NDP; NHS; NPHL1; NR0B1; NSX; NYS1; NYX; OA1; OASD; OCRL; ODT1; OFD1; OPA2; OPD1; OPEM; OPN1LW; OPN1MW; OTC; P3; PDHA1; PDR; PFC; PFKFB1; PGK1; PGK1P1; PGS; PHEX; PHKA1; PHKA2; PHP; PIGA; PLP1; POF1; POLA; POU3F4; PPMX; PRD; PRPS1; PRPS2; PRS; RCCP2; RENBP; RENS1; RP2; RP6; RPGR; RPS4X; RPS6KA3; RS1; S11; SDYS; SEDL; SERPINA7; SH2D1A; SHFM2; SLC25A5; SMAX2; SRPX; SRS; STS; SYN1; SYP; TAF1; TAZ; TBX22; TDD; TFE3; THAS; THC; TIMM8A; TIMP1; TKCR; TNFSF5; UBE1; UBE2A; WAS; WSN; WTS; WWS; XIC; XIST; XK; XM; XS; ZFX; ZIC3; ZNF261; ZNF41; ZNF6; AMELY; ASSP6; AZF1; AZF2; DAZ; GCY; RPS4Y; SMCY; SRY; ZFY; ABAT; AEZ; AFA; AFD1; ASAH1; ASD1; ASMT; CCAT; CECR9; CEPA; CLA3; CLN4; CSF2RA; CTS1; DF; DIH1; DWS; DYT2; DYT4; EBR3; ECT; EEFIA1L14; EYCL2; FANCB; GCSH; GCSL; GIP; GTS; HHG; HM1; HOAC; HOKPP2; HRPT1; HSD3B3; HTC1; HVIS; ICHQ; ICR1; ICR5; IL3RA; KAL2; KMS; KRT18; KSS; LCAT; LHON; LIMM MANBB; MCPH2; MEB; MELAS; MIC2; MPFD; MS; MSS; MTATP6; MTCO1; MTCO3; MTCYB; MTND1; MTND2; MTND4; MTND5; MTND6; MTRNR1; MTRNR2; MTTE; MTTG; MTT1; MTTK; MTTL1; MTTL2; MTTN; MTTP; MTTS1; NAMSD; OCD1; OPD2; PCK2; PCLD; PCOS1; PFKM; PKD3; PRCA1; PRO1; PROP1; RBS; RFXAP; RP; SHOX; SLC25A6; SPG5B; STO; SUOX; THM; or TTD. Each recombinant protein represents a separate embodiment of the present invention.

In another embodiment, the present invention provides a method for treating anemia in a subject, comprising contacting a cell of the subject with an in vitro-synthesized RNA molecule, the in vitro-synthesized RNA molecule encoding erythropoietin, thereby treating anemia in a subject. In another embodiment, the in vitro-synthesized RNA molecule further comprises a pseudouridine or a modified nucleoside. Each possibility represents a separate embodiment of the present invention. In another embodiment, the cell is a subcutaneous tissue cell. In another embodiment, the cell is a lung cell. In another embodiment, the cell is a fibroblast. In another embodiment, the cell is a lymphocyte. In another embodiment, the cell is a smooth muscle cell. In another embodiment, the cell is any other type of cell known in the art. Each possibility represents a separate embodiment of the present invention.

In another embodiment, the present invention provides a method for treating a vasospasm in a subject, comprising contacting a cell of the subject with an in vitro-synthesized RNA molecule, the in vitro-synthesized RNA molecule encoding inducible nitric oxide synthase (iNOS), thereby treating a vasospasm in a subject.

In another embodiment, the present invention provides a method for improving a survival rate of a cell in a subject, comprising contacting the cell with an in vitro-synthesized RNA molecule, the in vitro-synthesized RNA molecule encoding a heat shock protein, thereby improving a survival rate of a cell in a subject.

In another embodiment, the cell whose survival rate is improved is an ischemic cell. In another embodiment, the cell is not ischemic. In another embodiment, the cell has been exposed to an ischemic environment. In another embodiment, the cell has been exposed to an environmental stress. Each possibility represents a separate embodiment of the present invention.

In another embodiment, the present invention provides a method for decreasing an incidence of a restenosis of a blood vessel following a procedure that enlarges the blood vessel, comprising contacting a cell of the blood vessel with an in vitro-synthesized RNA molecule, the in vitro-synthesized RNA molecule encoding a heat shock protein, thereby decreasing an incidence of a restenosis in a subject.

In another embodiment, the procedure is an angioplasty. In another embodiment, the procedure is any other procedure known in the art that enlarges the blood vessel. Each possibility represents a separate embodiment of the present invention.

In another embodiment, the present invention provides a method for increasing a hair growth from a hair follicle is a scalp of a subject, comprising contacting a cell of the scalp with an in vitro-synthesized RNA molecule, the in vitro-synthesized RNA molecule encoding a telomerase or an immunosuppressive protein, thereby increasing a hair growth from a hair follicle.

In another embodiment, the immunosuppressive protein is α-melanocyte-stimulating hormone (α-MSH). In another embodiment, the immunosuppressive protein is transforming growth factor-β1 (TGF-β1). In another embodiment, the immunosuppressive protein is insulin-like growth factor-I (IGF-I). In another embodiment, the immunosuppressive protein is any other immunosuppressive protein known in the art. Each possibility represents a separate embodiment of the present invention.

In another embodiment, the present invention provides a method of inducing expression of an enzyme with antioxidant activity in a cell, comprising contacting the cell with an in vitro-synthesized RNA molecule, the in vitro-synthesized RNA molecule encoding the enzyme, thereby inducing expression of an enzyme with antioxidant activity in a cell.

In another embodiment, the enzyme is catalase. In another embodiment, the enzyme is glutathione peroxidase. In another embodiment, the enzyme is phospholipid hydroperoxide glutathione peroxidase. In another embodiment, the enzyme is superoxide dismutase-1. In another embodiment, the enzyme is superoxide dismutase-2. In another embodiment, the enzyme is any other enzyme with antioxidant activity that is known in the art. Each possibility represents a separate embodiment of the present invention.

In another embodiment, the present invention provides a method for treating cystic fibrosis in a subject, comprising contacting a cell of the subject with an in vitro-synthesized RNA molecule, the in vitro-synthesized RNA molecule encoding Cystic Fibrosis Transmembrane Conductance Regulator (CFTR), thereby treating cystic fibrosis in a subject.

In another embodiment, the present invention provides a method for treating an X-linked agammaglobulinemia in a subject, comprising contacting a cell of the subject with an in vitro-synthesized RNA molecule, the in vitro-synthesized RNA molecule encoding a Bruton's tyrosine kinase, thereby treating an X-linked agammaglobulinemia.

In another embodiment, the present invention provides a method for treating an adenosine deaminase severe combined immunodeficiency (ADA SCID) in a subject, comprising contacting a cell of the subject with an in vitro-synthesized RNA molecule, the in vitro-synthesized RNA molecule encoding an ADA, thereby treating an ADA SCID.

In another embodiment, the present invention provides a method for reducing immune responsiveness of the skin and improve skin pathology, comprising contacting a cell of the subject with an in vitro-synthesized RNA molecule, the in vitro-synthesized RNA molecule encoding an ecto-nucleoside triphosphate diphosphohydrolase, thereby reducing immune responsiveness of the skin and improve skin pathology.

In another embodiment, an RNA molecule or ribonucleotide molecule of the present invention is encapsulated in a nanoparticle. Methods for nanoparticle packaging are well known in the art, and are described, for example, in Bose S, et al (Role of Nucleolin in Human Parainfluenza Virus Type 3 Infection of Human Lung Epithelial Cells. J. Virol. 78:8146. 2004); Dong Y et al. Poly(d,l-lactide-co-glycolide)/montmorillonite nanoparticles for oral delivery of anticancer drugs. Biomaterials 26:6068. 2005); Lobenberg R. et al (Improved body distribution of 14C-labelled AZT bound to nanoparticles in rats determined by radioluminography. J Drug Target 5:171. 1998); Sakuma S R et al (Mucoadhesion of polystyrene nanoparticles having surface hydrophilic polymeric chains in the gastrointestinal tract. Int J Pharm 177:161. 1999); Virovic L et al. Novel delivery methods for treatment of viral hepatitis: an update. Expert Opin Drug Deliv 2:707. 2005); and Zimmermann E et al, Electrolyte- and pH-stabilities of aqueous solid lipid nanoparticle (SLN) dispersions in artificial gastrointestinal media. Eur J Pharm Biopharm 52:203. 2001). Each method represents a separate embodiment of the present invention.

Various embodiments of dosage ranges of compounds of the present invention can be used in methods of the present invention. In one embodiment, the dosage is in the range of 1-10 μg/day. In another embodiment, the dosage is 2-10 μg/day. In another embodiment, the dosage is 3-10 μg/day. In another embodiment, the dosage is 5-10 μg/day. In another embodiment, the dosage is 2-20 μg/day. In another embodiment, the dosage is 3-20 μg/day. In another embodiment, the dosage is 5-20 μg/day. In another embodiment, the dosage is 10-20 μg/day. In another embodiment, the dosage is 3-40 μg/day. In another embodiment, the dosage is 5-40 μg/day. In another embodiment, the dosage is 10-40 μg/day. In another embodiment, the dosage is 20-40 μg/day. In another embodiment, the dosage is 5-50 μg/day. In another embodiment, the dosage is 10-50 μg/day. In another embodiment, the dosage is 20-50 μg/day. In one embodiment, the dosage is 1-100 μg/day. In another embodiment, the dosage is 2-100 μg/day. In another embodiment, the dosage is 3-100 μg/day. In another embodiment, the dosage is 5-100 μg/day. In another embodiment the dosage is 10-100 μg/day. In another embodiment the dosage is 20-100 μg/day. In another embodiment the dosage is 40-100 μg/day. In another embodiment the dosage is 60-100 μg/day.

In another embodiment, the dosage is 0.1 μg/day. In another embodiment, the dosage is 0.2 μg/day. In another embodiment, the dosage is 0.3 μg/day. In another embodiment, the dosage is 0.5 μg/day. In another embodiment, the dosage is 1 μg/day. In another embodiment, the dosage is 2 mg/day. In another embodiment, the dosage is 3 μg/day. In another embodiment, the dosage is 5 μg/day. In another embodiment, the dosage is 10 μg/day. In another embodiment, the dosage is 15 μg/day. In another embodiment, the dosage is 20 μg/day. In another embodiment, the dosage is 30 μg/day. In another embodiment, the dosage is 40 μg/day. In another embodiment, the dosage is 60 μg/day. In another embodiment, the dosage is 80 μg/day. In another embodiment, the dosage is 100 μg/day.

In another embodiment, the dosage is 10 μg/dose. In another embodiment, the dosage is 20 μg/dose. In another embodiment, the dosage is 30 μg/dose. In another embodiment, the dosage is 40 μg/dose. In another embodiment, the dosage is 60 μg/dose. In another embodiment, the dosage is 80 μg/dose. In another embodiment, the dosage is 100 μg/dose. In another embodiment, the dosage is 150 μg/dose. In another embodiment, the dosage is 200 μg/dose. In another embodiment, the dosage is 300 μg/dose. In another embodiment, the dosage is 400 μg/dose. In another embodiment, the dosage is 600 μg/dose. In another embodiment, the dosage is 800 μg/dose. In another embodiment, the dosage is 1000 μg/dose. In another embodiment, the dosage is 1.5 mg/dose. In another embodiment, the dosage is 2 mg/dose. In another embodiment, the dosage is 3 mg/dose. In another embodiment, the dosage is 5 mg/dose. In another embodiment, the dosage is 10 mg/dose. In another embodiment, the dosage is 15 mg/dose. In another embodiment, the dosage is 20 mg/dose. In another embodiment, the dosage is 30 mg/dose. In another embodiment, the dosage is 50 mg/dose. In another embodiment, the dosage is 80 mg/dose. In another embodiment, the dosage is 100 mg/dose.

In another embodiment, the dosage is 10-20 μg/dose. In another embodiment, the dosage is 20-30 μg/dose. In another embodiment, the dosage is 20-40 μg/dose. In another embodiment, the dosage is 30-60 μg/dose. In another embodiment, the dosage is 40-80 μg/dose. In another embodiment, the dosage is 50-100 μg/dose. In another embodiment, the dosage is 50-150 μg/dose. In another embodiment, the dosage is 100-200 μg/dose. In another embodiment, the dosage is 200-300 μg/dose. In another embodiment, the dosage is 300-400 μg/dose. In another embodiment, the dosage is 400-600 μg/dose. In another embodiment, the dosage is 500-800 μg/dose. In another embodiment, the dosage is 800-1000 μg/dose. In another embodiment, the dosage is 1000-1500 μg/dose. In another embodiment, the dosage is 1500-2000 μg/dose. In another embodiment, the dosage is 2-3 mg/dose. In another embodiment, the dosage is 2-5 mg/dose. In another embodiment, the dosage is 2-10 mg/dose. In another embodiment, the dosage is 2-20 mg/dose. In another embodiment, the dosage is 2-30 mg/dose. In another embodiment, the dosage is 2-50 mg/dose. In another embodiment, the dosage is 2-80 mg/dose. In another embodiment, the dosage is 2-100 mg/dose. In another embodiment, the dosage is 3-10 mg/dose. In another embodiment, the dosage is 3-20 mg/dose. In another embodiment, the dosage is 3-30 mg/dose. In another embodiment, the dosage is 3-50 mg/dose. In another embodiment, the dosage is 3-80 mg/dose. In another embodiment, the dosage is 3-100 mg/dose. In another embodiment, the dosage is 5-10 mg/dose. In another embodiment, the dosage is 5-20 mg/dose. In another embodiment, the dosage is 5-30 mg/dose. In another embodiment, the dosage is 5-50 mg/dose. In another embodiment, the dosage is 5-80 mg/dose. In another embodiment, the dosage is 5-100 mg/dose. In another embodiment, the dosage is 10-20 mg/dose. In another embodiment, the dosage is 10-30 mg/dose. In another embodiment, the dosage is 10-50 mg/dose. In another embodiment, the dosage is 10-80 mg/dose. In another embodiment, the dosage is 10-100 mg/dose.

In another embodiment, the dosage is a daily dose. In another embodiment, the dosage is a weekly dose. In another embodiment, the dosage is a monthly dose. In another embodiment, the dosage is an annual dose. In another embodiment, the dose is one is a series of a defined number of doses. In another embodiment, the dose is a one-time dose. As described below, in another embodiment, an advantage of RNA, oligoribonucleotide, or polyribonucleotide molecules of the present invention is their greater potency, enabling the use of smaller doses.

In another embodiment, the present invention provides a method for producing a recombinant protein, comprising contacting an in vitro translation apparatus with an in vitro-synthesized oligoribonucleotide, the in vitro-synthesized oligoribonucleotide comprising a pseudouridine or a modified nucleoside, thereby producing a recombinant protein.

In another embodiment, the present invention provides a method for producing a recombinant protein, comprising contacting an in vitro translation apparatus with an in vitro-transcribed RNA molecule of the present invention, the in vitro-transcribed RNA molecule comprising a pseudouridine or a modified nucleoside, thereby producing a recombinant protein.

In another embodiment, the present invention provides an in vitro transcription apparatus, comprising: an unmodified nucleotide, a nucleotide containing a pseudouridine or a modified nucleoside, and a polymerase. In another embodiment, the present invention provides an in vitro transcription kit, comprising: an unmodified nucleotide, a nucleotide containing a pseudouridine or a modified nucleoside, and a polymerase. Each possibility represents a separate embodiment of the present invention.

In another embodiment, the in vitro translation apparatus comprises a reticulocyte lysate. In another embodiment, the reticulocyte lysate is a rabbit reticulocyte lysate.

In another embodiment, the present invention provides a method of reducing an immunogenicity of an oligoribonucleotide molecule or RNA molecule, the method comprising the step of replacing a nucleotide of the oligoribonucleotide molecule or RNA molecule with a modified nucleotide that contains a modified nucleoside or a pseudouridine, thereby reducing an immunogenicity of an oligoribonucleotide molecule or RNA molecule.

In another embodiment, the present invention provides a method of reducing an immunogenicity of a gene-therapy vector comprising a polyribonucleotide molecule or RNA molecule, the method comprising the step of replacing a nucleotide of the polyribonucleotide molecule or RNA molecule with a modified nucleotide that contains a modified nucleoside or a pseudouridine, thereby reducing an immunogenicity of a gene-therapy vector.

In another embodiment, the present invention provides a method of enhancing in vitro translation from an oligoribonucleotide molecule or RNA molecule, the method comprising the step of replacing a nucleotide of the oligoribonucleotide molecule or RNA molecule with a modified nucleotide that contains a modified nucleoside or a pseudouridine, thereby enhancing in vitro translation from an oligoribonucleotide molecule or RNA molecule.

In another embodiment, the present invention provides a method of enhancing in vivo translation from a gene-therapy vector comprising a polyribonucleotide molecule or RNA molecule, the method comprising the step of replacing a nucleotide of the polyribonucleotide molecule or RNA molecule with a modified nucleotide that contains a modified nucleoside or a pseudouridine, thereby enhancing in vivo translation from a gene-therapy vector.

In another embodiment, the present invention provides a method of increasing efficiency of delivery of a recombinant protein by a gene therapy vector comprising a polyribonucleotide molecule or RNA molecule, the method comprising the step of replacing a nucleotide of the polyribonucleotide molecule or RNA molecule with a modified nucleotide that contains a modified nucleoside or a pseudouridine, thereby increasing efficiency of delivery of a recombinant protein by a gene therapy vector.

In another embodiment, the present invention provides a method of increasing in vivo stability of gene therapy vector comprising a polyribonucleotide molecule or RNA molecule, the method comprising the step of replacing a nucleotide of the polyribonucleotide molecule or RNA molecule with a modified nucleotide that contains a modified nucleoside or a pseudouridine, thereby increasing in vivo stability of gene therapy vector.

In another embodiment, the present invention provides a method of synthesizing an in vitro-transcribed RNA molecule comprising a pseudouridine nucleoside, comprising contacting an isolated polymerase with a mixture of unmodified nucleotides and the modified nucleotide (Examples 2 and 7).

In another embodiment, in vitro transcription methods of the present invention utilize an extract from an animal cell. In another embodiment, the extract is from a reticulocyte or cell with similar efficiency of in vitro transcription. In another embodiment, the extract is from any other type of cell known in the art. Each possibility represents a separate embodiment of the present invention.

Any of the RNA molecules or oligoribonucleotide molecules of the present invention may be used, in another embodiment, in any of the methods of the present invention.

In another embodiment, the present invention provides a method of enhancing an immune response to an antigen, comprising administering the antigen in combination with mitochondrial (mt) RNA (Examples 1 and 5).

In another embodiment, the present invention provides a method of reducing the ability of an RNA molecule to stimulate a dendritic cell (DC), comprising modifying a nucleoside of the RNA molecule by a method of the present invention (Examples).

In another embodiment, the DC is a DC1 cell. In another embodiment, the DC is a DC2 cell. In another embodiment, the DC is a subtype of a DC1 cell or DC2 cell. Each possibility represents a separate embodiment of the present invention.

In another embodiment, the present invention provides a method of reducing the ability of an RNA molecule to stimulate signaling by TLR3, comprising modifying a nucleoside of the RNA molecule by a method of the present invention. In another embodiment, the present invention provides a method of reducing the ability of an RNA molecule to stimulate signaling by TLR7, comprising modifying a nucleoside of the RNA molecule by a method of the present invention. In another embodiment, the present invention provides a method of reducing the ability of an RNA molecule to stimulate signaling by TLR8, comprising modifying a nucleoside of the RNA molecule by a method of the present invention. Each possibility represents a separate embodiment of the present invention.

In another embodiment, all the inter-nucleotide linkages in the RNA, oligoribonucleotide, or polyribonucleotide molecule are phosphodiester. In another embodiment, the inter-nucleotide linkages are predominantly phosphodiester. In another embodiment, most of the inter-nucleotide linkages are phosphorothioate. In another embodiment, most the inter-nucleotide linkages are phosphodiester. Each possibility represents a separate embodiment of the present invention.

In another embodiment, the percentage of the inter-nucleotide linkages that are phosphodiester is above 50%. In another embodiment, the percentage is above 10%. In another embodiment, the percentage is above 15%. In another embodiment, the percentage is above 20%. In another embodiment, the percentage is above 25%. In another embodiment, the percentage is above 30%. In another embodiment, the percentage is above 35%. In another embodiment, the percentage is above 40%. In another embodiment, the percentage is above 45%. In another embodiment, the percentage is above 55%. In another embodiment, the percentage is above 60%. In another embodiment, the percentage is above 65%. In another embodiment, the percentage is above 70%. In another embodiment, the percentage is above 75%. In another embodiment, the percentage is above 80%. In another embodiment, the percentage is above 85%. In another embodiment, the percentage is above 90%. In another embodiment, the percentage is above 95%.

In another embodiment, a method of the present invention comprises increasing the number, percentage, or frequency of modified nucleosides in the RNA molecule to decrease immunogenicity or increase efficiency of translation. As provided herein, the number of modified residues in an RNA, oligoribonucleotide, or polyribonucleotide molecule determines, in another embodiment, the magnitude of the effects observed in the present invention.

In another embodiment, the present invention provides a method for introducing a recombinant protein into a cell of a subject, comprising contacting the subject with an in vitro-transcribed RNA molecule encoding the recombinant protein, the in vitro-transcribed RNA molecule further comprising a modified nucleoside, thereby introducing a recombinant protein into a cell of a subject.

In another embodiment, the present invention provides a method for decreasing TNF-α production in response to a gene therapy vector in a subject, comprising the step of engineering the vector to contain a pseudouridine or a modified nucleoside base, thereby decreasing TNF-α production in response to a gene therapy vector in a subject.

In another embodiment, the present invention provides a method for decreasing IL-12 production in response to a gene therapy vector in a subject, comprising the step of engineering the vector to contain a pseudouridine or a modified nucleoside base, thereby decreasing IL-12 production in response to a gene therapy vector in a subject.

In another embodiment, the present invention provides a method of reducing an immunogenicity of a gene therapy vector, comprising introducing a modified nucleoside into said gene therapy vector, thereby reducing an immunogenicity of a gene therapy vector.

As provided herein, findings of the present invention show that primary DC have an additional RNA signaling entity that recognizes m5C- and m6A-modified RNA and whose signaling is inhibited by modification of U residues.

In another embodiment, an advantage of an RNA, oligoribonucleotide, and polyribonucleotide molecules of the present invention is that RNA does not incorporate to the genome (as opposed to DNA-based vectors). In another embodiment, an advantage is that translation of RNA, and therefore appearance of the encoded product, is instant. In another embodiment, an advantage is that the amount of protein generated from the mRNA can be regulated by delivering more or less RNA. In another embodiment, an advantage is that repeated delivery of unmodified RNA could induce autoimmune reactions.

In another embodiment, an advantage is lack of immunogenicity, enabling repeated delivery without generation of inflammatory cytokines.

In another embodiment, stability of RNA is increased by circularization, decreasing degradation by exonucleases.

In another embodiment, the present invention provides a method of treating a subject with a disease that comprises an immune response against a self-RNA molecule, comprising administering to the subject an antagonist of a TLR-3 molecule, thereby treating a subject with a disease that comprises an immune response against a self-RNA molecule.

In another embodiment, the present invention provides a method of treating a subject with a disease that comprises an immune response against a self-RNA molecule, comprising administering to the subject an antagonist of a TLR-7 molecule, thereby treating a subject with a disease that comprises an immune response against a self-RNA molecule.

In another embodiment, the present invention provides a method of treating a subject with a disease that comprises an immune response against a self-RNA molecule, comprising administering to the subject an antagonist of a TLR-8 molecule, thereby treating a subject with a disease that comprises an immune response against a self-RNA molecule.

In another embodiment, the disease that comprises an immune response against a self-RNA molecule is an autoimmune disease. In another embodiment, the disease is systemic lupus erythematosus (SLE). In another embodiment, the disease is another disease known in the art that comprises an immune response against a self-RNA molecule. Each possibility represents a separate embodiment of the present invention.

In another embodiment, the present invention provides a kit comprising a reagent utilized in performing a method of the present invention. In another embodiment, the present invention provides a kit comprising a composition, tool, or instrument of the present invention.

In another embodiment, the present invention provides a kit for measuring or studying signaling by a TLR3, TLR7 and TLR8 receptor, as exemplified in Example 4.

In another embodiment, a treatment protocol of the present invention is therapeutic. In another embodiment, the protocol is prophylactic. Each possibility represents a separate embodiment of the present invention.

In one embodiment, the phrase "contacting a cell" or "contacting a population" refers to a method of exposure, which can be direct or indirect. In one method such contact comprises direct injection of the cell through any means well known in the art, such as microinjection. In another embodiment, supply to the cell is indirect, such as via provision in a culture medium that surrounds the cell, or administration to a subject, or via any route known in the art. In another embodiment, the term "contacting" means that the molecule of the present invention is introduced into a subject receiving treatment, and the molecule is allowed to come in contact with the cell in vivo. Each possibility represents a separate embodiment of the present invention.

Methods for quantification of reticulocyte frequency and for measuring EPO biological activity are well known in the art, and are described, for Example, in Ramos, A S et al (Biological evaluation of recombinant human erythropoietin in pharmaceutical products. Braz J Med Biol Res 36:1561). Each method represents a separate embodiment of the present invention.

Compositions of the present invention can be, in another embodiment, administered to a subject by any method known to a person skilled in the art, such as parenterally, paracancerally, transmucosally, transdermally, intramuscularly, intravenously, intra-dermally, subcutaneously, intra-peritonealy, intra-ventricularly, intra-cranially, intra-vaginally or intra-tumorally.

In another embodiment of methods and compositions of the present invention, the compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound and the inert carrier or diluent, a hard gelating capsule.

In other embodiments, the pharmaceutical compositions are administered by intravenous, intra-arterial, or intramuscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In another embodiment, the pharmaceutical compositions are administered topically to body surfaces and are thus formulated in a form suitable for topical administration. Suitable topical formulations include gels, ointments, creams, lotions, drops and the like. For topical administration, the compositions or their physiologically tolerated derivatives are prepared and applied as solutions, suspensions, or emulsions in a physiologically acceptable diluent with or without a pharmaceutical carrier.

In another embodiment, the composition is administered as a suppository, for example a rectal suppository or a urethral suppository. In another embodiment, the pharmaceutical composition is administered by subcutaneous implantation of a pellet. In another embodiment, the pellet provides for controlled release of agent over a period of time.

In another embodiment, the active compound is delivered in a vesicle, e.g. a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

As used herein "pharmaceutically acceptable carriers or diluents" are well known to those skilled in the art. The carrier or diluent may be may be, in various embodiments, a solid carrier or diluent for solid formulations, a liquid carrier or diluent for liquid formulations, or mixtures thereof.

In another embodiment, solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In other embodiments, pharmaceutically acceptable carriers for liquid formulations may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In another embodiment, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmellose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hydroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants. Each of the above excipients represents a separate embodiment of the present invention.

In another embodiment, the pharmaceutical compositions provided herein are controlled-release compositions, i.e. compositions in which the compound is released over a period of time after administration. Controlled- or sustained-release compositions include formulation in lipophilic depots (e.g. fatty acids, waxes, oils). In another embodiment, the composition is an immediate-release composition, i.e. a composition in which the entire compound is released immediately after administration.

In another embodiment, molecules of the present invention are modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications also increase, in another embodiment, the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

An active component is, in another embodiment, formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Each of the above additives, excipients, formulations and methods of administration represents a separate embodiment of the present invention.

EXPERIMENTAL DETAILS SECTION

Example 1: Naturally Occurring RNA Molecules Exhibit Differential Abilities to Activate Dendritic Cells Materials and Experimental Methods Plasmids and Reagents Plasmids pT7T3D-MART-1 and pUNO-hTLR3 were obtained from the ATCC (Manassas, Va.) and InvivoGen (San Diego, Calif.), respectively. pTEVluc was obtained from Dr Daniel Gallie (UC Riverside), contains pT7-TEV (the leader sequence of the tobacco etch viral genomic RNA)-luciferase-A50, and is described in Gallie, D R et al, 1995. The tobacco etch viral 5' leader and poly(A) tail are functionally synergistic regulators of translation. Gene 165: 233) pSVren was generated from p2luc (Grentzmann G, Ingram J A, et al, A dual-luciferase reporter system for studying recoding signals. RNA 1998; 4(4): 479-86) by removal of the firefly luciferase coding sequence with BamHI and NotI digestions, end-filling, and religation.

Human TLR3-specific siRNA, pTLR3-sh was constructed by inserting synthetic ODN encoding shRNA with 20-nt-long homology to human TLR3 (nt 703-722, accession: NM_003265) into plasmid pSilencer 4.1-CMV-neo (Ambion, Austin, Tex.). pCMV-hTLR3 was obtained by first cloning hTLR3-specific PCR product (nt 80-2887; Accession NM_003265) into pCRII-TOPO (Invitrogen, Carlsbad, Calif.), then released with Nhe 1-Hind III cutting and subcloning to the corresponding sites of pcDNA3.1 (Invitrogen). LPS (E. coli 055:B5) was obtained from Sigma Chemical Co, St. Louis, Mo. CpG ODN-2006 and R-848 were obtained from InvivoGen.

Cells and Cell Culture

Human embryonic kidney 293 cells (ATCC) were propagated in DMEM supplemented with glutamine (Invitrogen) and 10% FCS (Hyclone, Ogden, Utah) (complete medium). In all cases herein, "293 cells" refers to human embryonic kidney (HEK) 293 cells. 293-hTLR3 cell line was generated by transforming 293 cells with pUNO-hTLR3. Cell lines 293-hTLR7, 293-hTLR8 and 293-hTLR9 (InvivoGen) were grown in complete medium supplemented with blasticidin (10 µg/ml) (Invivogen). Cell lines 293-ELAM-luc and TLR7-293 (M. Lamphier, Eisai Research Institute, Andover Mass.), and TLR3-293 cells were cultured as described (Kariko et al, 2004, mRNA is an endogenous ligand for Toll-like receptor 3. J Biol Chem 279: 12542-12550). Cell lines 293, 293-hTLR7 and 293-hTLR8 were stably transfected with pTLR3-sh and selected with G-418 (400 µg/ml) (Invitrogen). Neo-resistant colonies were screened and only those that did not express TLR3, determined as lack of IL-8 secretion in response to poly(I):(C), were used in further studies. Leukopheresis samples were obtained from HIV-uninfected volunteers through an IRB-approved protocol.

Murine DC Generation

Murine DC were generated by collecting bone marrow cells from the tibia and femurs of 6-8-week-old C57BL/6 mice and lysing the red blood cells. Cells were seeded in 6-well plates at $10^6$ cells/well in 2 ml DMEM+10% FCS and 20 ng/ml muGM-CSF (R & D Systems). On day 3, 2 ml of fresh medium with muGM-CSF was added. On day 6, 2 ml medium/well was collected, and cells were pelleted and resuspended in fresh medium with muGM-CSF. On day 7 of the culture, the muDC were harvested, washed.

Natural RNA

Mitochondria were isolated from platelets obtained from the University of Pennsylvania Blood Bank using a fractionation lyses procedure (Mitochondria isolation kit; Pierce, Rockford, Ill.). RNA was isolated from the purified mitochondria, cytoplasmic and nuclear fractions of 293 cells, un-fractioned 293 cells, rat liver, mouse cell line TUBO, and DHSalpha strain of E. coli by Master Blaster® (BioRad, Hercules, Calif.). Bovine tRNA, wheat tRNA, yeast tRNA, E. coli tRNA, poly(A)+mRNA from mouse heart and poly(I):(C) were purchased from Sigma, total RNA from human spleen and E. coli RNA were purchased from Ambion. Oligoribonucleotide-5'-monophosphates were synthesized chemically (Dharmacon, Lafayette, Colo.).

Aliquots of RNA samples were incubated in the presence of Benzonase nuclease (1 U per 5 µl of RNA at 1 microgram per microliter (µg/µl) for 1 h) (Novagen, Madison, Wis.). Aliquots of RNA-730 were digested with alkaline phosphatase (New England Biolabs). RNA samples were analyzed by denaturing agarose or polyacrylamide gel electrophoresis for quality assurance. Assays for LPS in RNA preparations using the Limulus Amebocyte Lysate gel clot assay were negative with a sensitivity of 3 picograms per milliliter (pg/ml) (University of Pennsylvania, Core Facility).

HPLC Analysis

Nucleoside monophosphates were separated and visualized via HPLC. To release free nucleoside 3'-monophosphates, 5 µg aliquots of RNA were digested with 0.1 U RNase T2 (Invitrogen) in 10 µl of 50 mM NaOAc and 2 mM EDTA buffer (pH 4.5) overnight, then the samples were injected into an Agilent 1100 HPLC using a Waters Symmetry C18 column (Waters, Milford, Mass.). At a flow rate of 1 mL/min, a gradient from 100% buffer A (30 mM $KH_2PO_4$ and 10 mM tetraethylammonium phosphate [PicA reagent, Waters], pH 6.0) to 30% buffer B (acetonitrile) was run over 60 minutes. Nucleotides were detected using a photodiode array at 254 nm. Identities were verified by retention times and spectra.

Dendritic Cell Assays

Dendritic cells in 96-well plates (approximately $1.1 \times 10^5$ cells/well) were treated with R-848, Lipofectin®, or Lipofectin®-RNA for 1 h, then the medium was changed. At the end of 8 h (unless otherwise indicated), cells were harvested for either RNA isolation or flow cytometry, while the collected culture medium was subjected to cytokine ELISA. The levels of IL-12 (p70) (BD Biosciences Pharmingen, San Diego, Calif.), IFN-α, TNF-α, and IL-8 (Biosource International, Camarillo, Calif.) were measured in supernatants by sandwich ELISA. Cultures were performed in triplicate or quadruplicate and measured in duplicate.

Northern Blot Analysis

RNA was isolated from MDDCs after an 8 h incubation following treatment as described above. Where noted, cells were treated with 2.5 µg/ml cycloheximide (Sigma) 30 min prior to the stimulation and throughout the entire length of incubation. RNA samples were processed and analyzed on Northern blots as described (Kariko et al, 2004, ibid) using human TNF-α and GAPDH probes derived from plasmids (pE4 and pHcGAP, respectively) obtained from ATCC.

Results

To determine the immuno-stimulatory potential of different cellular RNA subtypes, RNA was isolated from different subcellular compartments—i.e. cytoplasm, nucleus and mitochondria. These RNA fractions, as well as total RNA, tRNA and polyA-tail-selected mRNA, all from mammalian sources, were complexed to Lipofectin® and added to MDDC. While mammalian total, nuclear and cytoplasmic RNA all stimulated MDDC, as evidenced by detectable TNF-α secretion, the TNF-α levels were much lower than those induced by in vitro-synthesized mRNA (FIG. 1). Moreover, mammalian tRNA did not induce any detectable level of TNF-α, while mitochondrial (mt) RNA induced much more TNF-α than the other mammalian RNA subtypes. Bacterial total RNA was also a potent activator of MDDC; by contrast, bacterial tRNA induced only a low level of TNF-α, tRNA from other sources (yeast, wheat germ, bovine) were non-stimulatory. Similar results were observed when RNA from other mammalian sources was tested. When RNA samples were digested with Benzonase, which cleaves ssRNA and dsRNA, RNA signaling was abolished in MDDC, verifying that TNF-α secretion was due to the RNA in the preparations. The activation potentials of the RNA types tested exhibited an inverse correlation with the extent of nucleoside modification. Similar results were obtained in the experiments described in this Example for both types of cytokine-generated DC.

These findings demonstrate that the immunogenicity of RNA is affected by the extent of nucleoside modification, with a greater degree of modification tending to decrease immunogenicity.

Example 2: In Vitro Synthesis of RNA Molecules with Modified Nucleosides

Materials and Experimental Methods

In Vitro-Transcribed RNA

Using in vitro transcription assays (MessageMachine and MegaScript kits; Ambion) the following long RNAs were generated by T7 RNA polymerase (RNAP) as described (Kariko et al, 1998, Phosphate-enhanced transfection of cationic lipid-complexed mRNA and plasmid DNA. Biochim Biophys Acta 1369, 320-334) (Note: the names of templates are indicated in parenthesis; the number in the name of the RNA specifies the length): RNA-1866 (Nde I-linearized pTEVluc) encodes firefly luciferase and a 50 nt-long polyA-tail. RNA-1571 (Ssp I-linearized pSVren) encodes *Renilla* luciferase. RNA-730 (Hind III-linearized pT7T3D-MART-1) encodes the human melanoma antigen MART-1. RNA-713 (EcoR I-linearized pT7T3D-MART-1) corresponds to antisense sequence of MART-1, RNA-497 (Bgl II-linearized pCMV-hTLR3) encodes a partial 5' fragment of hTLR3. Sequences of the RNA molecules are as follows:

```
RNA-1866:
                                                         (SEQ ID No: 1)
ggaauucucaacacaacauauacaaaacaaacgaaucucaagcaaucaagcauucuacuucuauugcagcaauu uaaaucauuucuuuuaaagcaaaagcaauuuucugaaaauuuucaccauuuacgaacgauagccauggaagac gccaaaaacauaaagaaaggcccggcgccauucuauccucuagaggauggaaccgcuggagagcaacugcauaa ggcuaugaagagauacgcccugguuccuggaacaauugcuuuuacagaugcacauaucgaggugaacaucacg uacgcggaauacuucgaaauguccguucgguuggcagaagcuaugaaacgauaugggcugaauacaaaucaca gaaucgucguaugcagugaaaacucucuucaauucuuuaugccggugguugggcgcguuauuuaucggaguug caguugcgcccgcgaacgacauuuauaaugaacgugaauugcucaacaguaugaacauuucgcagccuaccgu aguguuuguuuccaaaaaggggguugcaaaaaauuuugaacgugcaaaaaaauuaccaauaauccagaaaauu auuaucauggauucuaaaacggauuaccagggauuucagucgauguacacguucgucacaucucaucuaccuc ccgguuuuaaugaauacgauuuugaccagaguccuuugaucgugacaaaacaauugcacugauaaugaauuc cucuggaucuacuggguuaccuaaggguguggcccuuccgcauagaacugccugcgucagauucucgcaugc cagagauccuauuuuuggcaaucaaaucauuccggauacugcgauuuuaaguguguuguuccauuccaucacgg uuuuggaauguuuacuacacucggauauuugauauguggauuucgagucgucuuaauguauagauuugaaga agagcuguuuuuacgaucccuucaggauuacaaaauucaaagugcguugcuaguaccaacccuauuuucauuc uucgccaaaagcacucugauugacaaauacgauuuaucuaauuuacacgaaauugcuucgggggcgcaccuc uuucgaaagaagucggggaagcgguugcaaaacgcuuccaucuuccagggauacgacaaggauaugggcucac ugagacuacaucagcuauucugauuacacccgaggggggaugauaaaccgggcgcggucgguaaaguuguucca uuuuuugaagcgaagguugugggaucuggauaccgggaaaacgcuggggcguuaaucagagaggcgaauuaugu gucagaggaccuaugauuauguccgguuauguaaacaauccggaagcgaccaacgccuugauugacaaggaug gauggcuacauucuggagacauagcuuacugggacgaagacgaacacuucuucauaguugaccgcuugaaguc uuuaauuaaauacaaaggauaucagguggcccccgcugaauuggaaucgauauuguuacaacacccccaacauc uucgacgcgggcguggcaggucuucccgacgaugacgccggugaacuucccgccgccguuguuguuuuggag cacggaaagacgaugacggaaaaagagaucguggauuguggccagucaaguaacaaccgcgaaaaaguugc
```

-continued gcggaggaguugoguuuguggacgaaguaccgaaaggucuuaccggaaaacucgacgcaagaaaaaucagaga
gauccucauaaaggccaagaagggcggaaaguccaaauuguaaaauguaacucuagaggaucccaaaaaaaaa
aaaaaaaaaaaaaaaaaaaaaaaaaaaaaaaaaaaaaaaaaca.

RNA-1571:
(SEQ ID No: 2)
ggcaugccaccaugacuucgaaaguuuaugauccagaacaaaggaaacggaugauaacugguccgcagugguг
ggccagauguaaacaaaugaaguucuugauucauuuauuaauuauuaugauucagaaaaacaugcagaaaau
gcuguuauuuuuuuacaugguaacgcggccucuucuuauuuauggcgacauguuugugccacauauugagcca
guagcgcgguguauauaccagaccuuauugguauggggcaaaucaggcaaaucgguaauggguucuuauagg
uuacuugaucauuacaaauaucuuacugcaugguuugaacuucuuaauuuaccaaagaagaucauuuuuguc
ggccaugauuggggugcuuguuugcauuucauuauagcuaugagcaucaagauaagaucaaagcaauaguu
cacgcugaaaguguaguagaugugauugaaucauggggaugaauggccugauauugaagaagauauugcguug
aucaaaucugaagaaggagaaaaaauggguuuggagaauaacuucuucgugaaaccauguugccaucaaaaa
ucaugagaaaguuagaaccagaagaauuugcagcauaucuugaaccauucaaagagaaaggugaaguucgucg
uccaacauuaucauggccucgugaaaucccguuaguaaaagguguaaaccugacguuguacaaauuguuagg
aauuauaaugcuuaucuacgugcaaguaugauuauuaccaaaaauguuuauugaaucggacccaggauucuuu
uccaaugcuauuguugaaggugccaagaaguuuccuaauacugaauuugucaaaguaaaaggucuucauuuu
ucgcaagaagaugcaccugaugaaaugggaaaauauaucaaaucguucguugagcgaguucucaaaaaugaac
aaaugucgacgggggccccuaggaauuuuuuagggaagaucuggccuuccuacaaggaaggccagggaauu
uucuucagagcagaccagagccaacagccccaccagaagagagcuucaggucuggggugagagacaacaacuccc
ccucagaagcaggagccgauagacaaggaacuguauccuuuaacuucccucagaucacucuuuggcaacgaccc
cucgucacaauaaagauagggggggcaacuaaagggaucggccgcuucgagcagacaugauaagauacauugau
gaguuggacaaaccacaacuagaaugcagugaaaaaaaugcuuuauuugugaaauuugugaugcuauugcu
uuauuuguaaccauuauaagcugcaauaaacaaguuaacaacaacaauugcauucauuuuauguuucagguuc
aggggagguguggaagguuuuuuaaagcaaguaaaaccucuacaaaugugguaaaaucgauaaguuuaaac
agauccagguggcacuuuucggggaaaugugcgcggaaccccuauuuguuuauuuuucuaaauacauucaaa
uauguauccgcucaugagacaauaacccugauaaaugcuucaauaau.

RNA-730:
(SEQ ID No: 3)
gggaauuuggcccucgaggccaagaauucggcacgaggcacgcggccagccagcagacagaggacucucauua
aggaaggugguccugugcccugacccuacaagaugccaagagaagaugcucacuucaucuauggguuaccccaag
aaggggcacggccacucuuacaccacggcugaagaggccgcuggggaucggcauccugacagugauccuggagag
ucuuacugcucaucggcuguuuguauuguagaagacgaaauggauacagagccuugauggauaaaagucuuc
auguuggcacucaaugugccuuaacaagaagaugcccacaagaagggguuugaucaucgggacagcaaaguguc
ucuucaagagaaaaacugugaaccugugguucccaaugcuccaccugcuuaugaaacacucucugcagaacag
ucaccaccaccuuauucaccuuaagagccagcgagacaccugagacaugcugaaauuauuucucucacacuuuu
gcuugaauuaaauacagacaucuaauguucuccuuuggaauggguaggaaaaaugcaagccaucucuaauaa
uaagucaguguuaaaauuuuaguaggcccgcuagcaguacuaaucaugugaggaaaugaugagaaauauuaaa
uugggaaaacuccaucaauaaauguugcaaugcaugauaaaaaaaaaaaaaaaaaaaaaacugcggccgca.

RNA-713
(SEQ ID No: 4)
gggaauaagcuugcggccgcaguuuuuuuuuuuuuuuuuuuaucaugcauugcaacau
uuauugauggaguuuucccaauuuaauauuuucucaucauuuccucacaugauuaguacugcuagcggaccua
cuaaaauuuuaacacugacuuauuauuagagaaauggcuugcauuuuuccuacaccauuccaaaggagaacauua

```
gaugucuguauaaauucaagcaaaagugugagagaaauaauuucagcaugucucaggugucucgcuggcucu uaaggugaauaagguggugguugacuguucugcagagaguuucucauaagcagguggagcauugggaaccaca gguucacaguuuuucucuugaagagacacuuugcuguccccgaugaucaaacccuucuugugggcaucuucuu guuaaggcacauugagugccaacaugaagacuuuuauccaucaaggcucuguauccauuucgucuucuacaau accaacagccgaugagcaguaagacucccaggaucacugucaggaugccgaucccagcggccucuucagccgu gguguaagaguggccgugcccuucuuggggguaaccauagaugaagugagcaucuucucuuggcaucuugua gggucagggcacaggacaccuuccuuaaugagaguccucugucugcuggcuggccgcgugccucgugccgaa uu.

RNA-479:

(SEQ ID No: 5)
gggagacccaagcuggcuagcagucauccaacagaaucaugagacagacuuugccuuguaucuacuuuugggg gggccuuugcccuuugggaugcugugugcauccuccaccaccaagugcacuguuagccaugaaguugcuga cugcagccaccugaaguugacucagguacccgaugaucuacccacaaacauaacaguguugaaccuuacccaua aucaacucagaagauuaccagccgccaacuucacaagguauagccagcuaacuagcuuggauguaggauuuaa caccaucucaaaacuggagccagaauugugccagaaacuucccauguuaaaaguuuugaaccuccagcacaaug agcuacucaacuuucugauaaaaccuuugccuucugcacgaauuugacugaacuccaucucauguccaacuc aauccagaaaauuaaaaauaaucccuuugucaagcagaagaauuuaaucacauua.
```

To obtain modified RNA, the transcription reaction was assembled with the replacement of one (or two) of the basic NTPs with the corresponding triphosphate-derivative(s) of the modified nucleotide 5-methylcytidine, 5-methyluridine, 2-thiouridine, $N^6$-methyladenosine or pseudouridine (Tri-Link, San Diego, Calif.). In each transcription reaction, all 4 nucleotides or their derivatives were present at 7.5 millimolar (mM) concentration. In selected experiments, as indicated, 6 mM m7GpppG cap analog (New England BioLabs, Beverly, Mass.) was also included to obtain capped RNA. ORN5 and ORN6 were generated using DNA oligodeoxynucleotide templates and T7 RNAP (Silencer® siRNA construction kit, Ambion).

Results

Figures 2A, 2B, 2C:
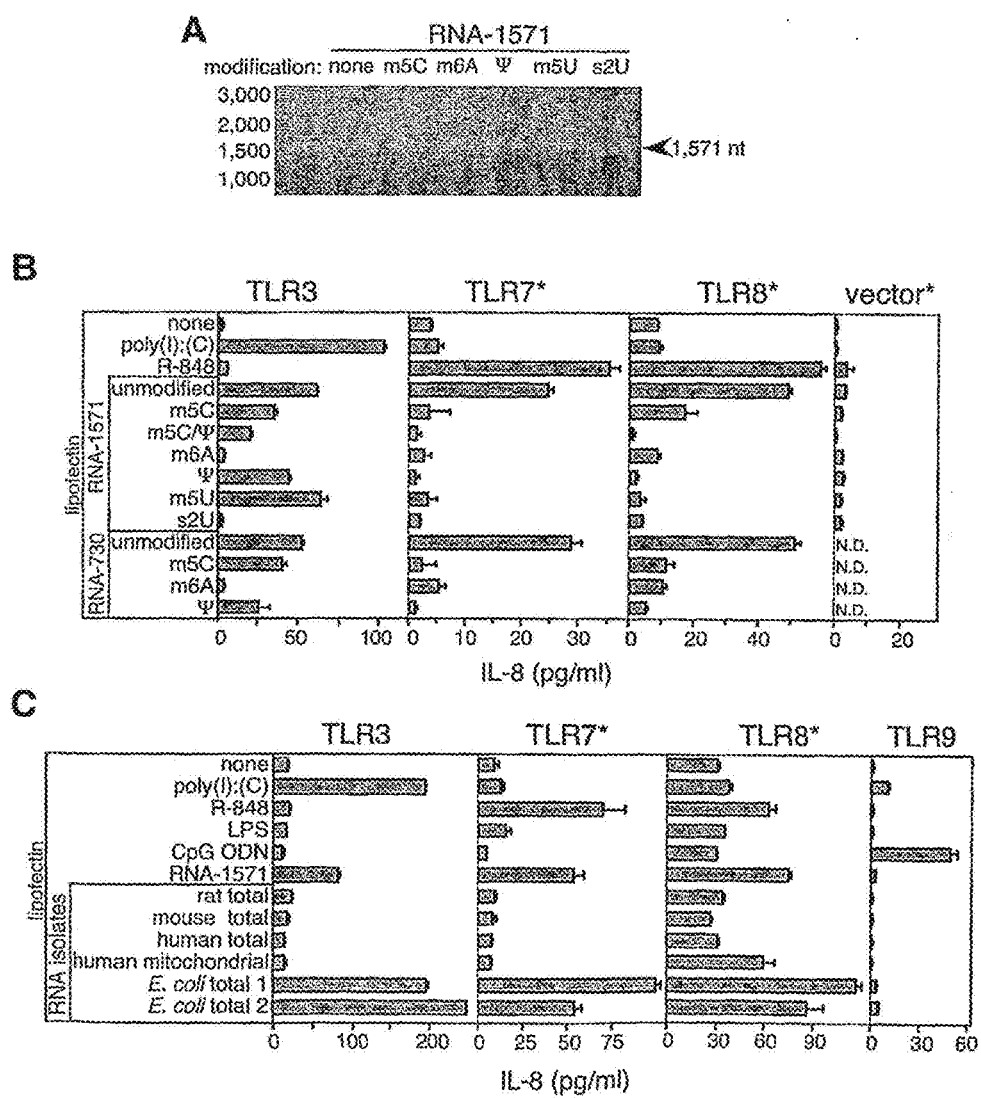
(FIG. 2A) Aliquots (1 μg) of in vitro-transcribed RNA-1571 without (none) or with $m^5C$, $m^6A$, Ψ, $m^5U$ or $s^2U$ nucleoside modifications were analyzed on denaturing agarose gel followed by ethidium bromide-staining and UV-illumination.
(FIG. 2B) 293 cells expressing human TLR3, TLR7, TLR8 and control vectors were treated with Lipofectin® alone, Lipofectin®-R-848 (1 μg/ml) or RNA (5 μg/ml). Modified nucleosides present in RNA-730 and RNA-1571 are noted. 293-ELAM-luc cells were use as control cells.
(FIG. 2C) CpG ODN-2006 (5 μg/ml), LPS (1.0 μg/ml) and RNA isolates were obtained from rat liver, mouse cell line (TUBO) and human spleen (total), human platelet mitochondrial RNA, or from two different E. coli sources. 293-hTLR9 cells served as control. After 8 h, IL-8 was measured in the supernatants by ELISA. Mean values±SEM are shown. Cell lines containing hTLR3-targeted siRNA are indicated with asterisk. The results are representative of four independent experiments.

To further test the effect of nucleoside modifications on immunogenicity, an in vitro system was developed for producing RNA molecules with pseudouridine or modified nucleosides. In vitro transcription reactions were performed in which 1 or 2 of the 4 nucleotide triphosphates (NTP) were substituted with a corresponding nucleoside-modified NTP. Several sets of RNA with different primary sequences ranging in length between 0.7-1.9 kb, and containing either none, 1 or 2 types of modified nucleosides were transcribed. Modified RNAs were indistinguishable from their non-modified counterparts in their mobility in denaturing gel electrophoresis, showing that they were intact and otherwise unmodified (FIG. 2A). This procedure worked efficiently with any of T7, SP6, and T3 phage polymerases, and therefore is generalizable to a wide variety of RNA polymerases.

These findings provide a novel in vitro system for production of RNA molecules with modified nucleosides.

Example 3: In Vitro-Transcribed RNA Stimulates Human TLR3, and Nucleoside Modifications Reduce the Immunogenicity of RNA Materials and Experimental Methods Parental 293, 293-hTLR7 and 293-hTLR8 cells, all expressing TLR3-specific siRNA, and 293-hTLR9, TLR3-293 were seeded into 96-well plates ($5\times10^4$ cells/well) and cultured without antibiotics. On the subsequent day, the cells were exposed to R-848 or RNA complexed to Lipofectin® (Invitrogen) as described (Kariko et al, 1998, ibid). RNA was removed after one hour (h), and cells were further incubated in complete medium for 7 h. Supernatants were collected for IL-8 measurement.

Results

To determine whether modification of nucleosides influences the RNA-mediated activation of TLRs, human embryonic kidney 293 cells were stably transformed to express human TLR3. The cell lines were treated with Lipofectin®-complexed RNA, and TLR activation was monitored as indicated by interleukin (IL)-8 release. Several different RNA molecules were tested. Unmodified, in vitro-transcribed RNA elicited a high level of IL-8 secretion. RNA containing m6A or s2U nucleoside modifications, but contrast, did not induce detectable IL-8 secretion (FIG. 2B). The other nucleoside modifications tested (i.e. m5C, m5U, Ψ, and m5C/V) had a smaller suppressive effect on TLR3 stimulation (FIG. 2B). Ψ refers to pseudouridine.

Thus, nucleoside modifications such as $m^6A$ $s^2U$, $m^5C$, $m^5U$, T, reduce the immunogenicity of RNA as mediated by TLR3 signaling.

Example 4: In Vitro-Transcribed RNA Stimulates Human TLR7 and TLR8, and Nucleoside Modifications Reduce the Immunogenicity of RNA To test the possibility that 293 express endogenous TLR3 that interfere with assessing effects of RNA on specific TLR receptors, expression of endogenous TLR3 was eliminated from the 293-TLR8 cell line by stably transfecting the cells with a plasmid expressing TLR3-specific short hairpin (sh) RNA (also known as siRNA). This cell line was used for further study, since it did not respond to poly(I):(C), LPS, and CpG-containing oligodeoxynucleotides (ODNs), indicating the absence of TLR3, TLR4 and TLR9, but did respond to R-848, the cognate ligand of human TLR8 (FIG. 2B). When the 293-hTLR8 cells expressing TLR3-targeted shRNA (293-hTLR8 shRNA-TLR3 cells) were transfected with in vitro-transcribed RNA, they secreted large amounts of IL-8. By contrast, RNA containing most of the nucleoside modifications ($m^5C$, $m^5U$, Ψ, and $m^5C$/Ψ, $s^2U$) eliminated stimulation (no more IL-8 production than the negative control, i.e. empty vector). m6A modification had a variable effect, in some cases eliminating and in other cases reducing IL-8 release (FIG. 2B).

The results of this Example and the previous Example show that (a) RNA with natural phosphodiester inter-nucleotide linkages (e.g. in vitro-transcribed RNA) stimulates human TLR3, TLR7 and TLR8; and (b) nucleoside modifications such as m6A, m5C, m5U, s2U and Ψ, alone and in combination, reduce the immunogenicity of RNA as mediated by TLR3, TLR7 and TLR8 signaling. In addition, these results provide a novel system for studying signaling by specific TLR receptors.

Example 5: Nucleoside Modifications Reduce the Immunogenicity of RNA as Mediated by TLR7 and TLR8 Signaling The next set of experiments tested the ability of RNA isolated from natural sources to stimulate TLR3, TLR7 and TLR8. RNA from different mammalian species were transfected into the TLR3, TLR7 and TLR8-expressing 293 cell lines described in the previous Example. None of the mammalian RNA samples induced IL-8 secretion above the level of the negative control. By contrast, bacterial total RNA obtained from two different *E. coli* sources induced robust IL-8 secretion in cells transfected with TLR3, TLR7 and TLR8, but not TLR9 (FIG. 2C). Neither LPS nor unmethylated DNA (CpG ODN) (the potential contaminants in bacterial RNA isolates) activated the tested TLR3, TLR7 or TLR8. Mitochondrial RNA isolated from human platelets stimulated human TLR8, but not TLR3 or TLR7.

These results demonstrate that unmodified in vitro-transcribed and bacterial RNA are activators of TLR3, TLR7 and TLR8, and mitochondrial RNA stimulates TLR8. In addition, these results confirm the finding that nucleoside modification of RNA decreases its ability to stimulate TLR3, TLR7 and TLR8.

Example 6: Nucleoside Modifications Reduce the Capacity of RNA to Induce Cytokine Secretion and Activation Marker Expression by DC Materials and Experimental Methods DC Stimulation Assays After 20 h of incubation with RNA, DCs were stained with CD83-phycoerythrin mAb (Research Diagnostics Inc, Flanders, N.J.), HLA-DR-Cy5PE, and CD80 or CD86-fluorescein isothiocyanate mAb and analyzed on a FACScalibur® flow cytometer using CellQuest® software (BD Biosciences). Cell culture supernatants were harvested at the end of a 20 h incubation and subjected to cytokine ELISA. The levels of IL-12 (p70) (BD Biosciences Pharmingen, San Diego, Calif.), IFN-α, and TNF-α (Biosource International, Camarillo, Calif.) were measured in supernatants by ELISA. Cultures were performed in triplicate or quadruplicate, and each sample was measured in duplicate.

Results

Figures 3A, 3B, 3C, 3D:
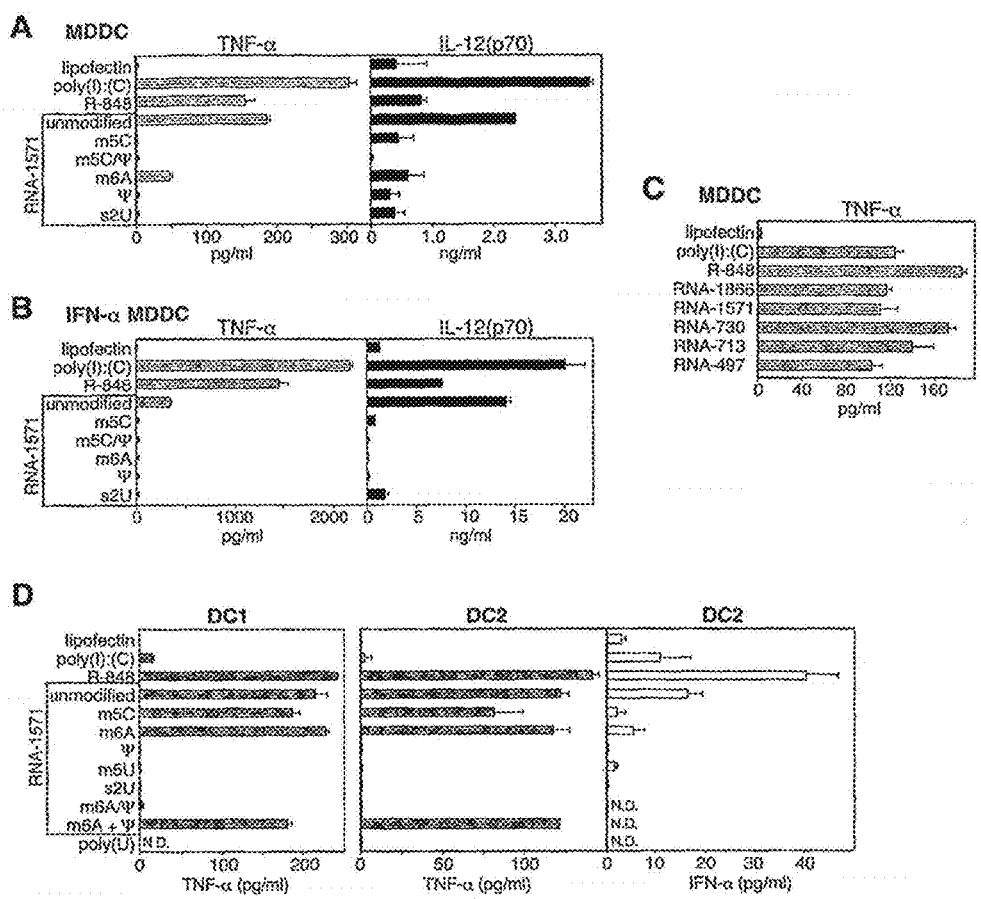
FIG. 3, comprising FIGS. 3A through 3E. Cytokine production by RNA-transfected DC demonstrates that all modifications block activation of cytokine generated DC, while only uridine modifications block blood-derived DC activation. MDDC generated with GM-CSF/IL-4 (FIG. 3A, FIG. 3C) or GM-CSF/IFN-α MDDCs (FIG. 3B), and primary DC1 and DC2 (FIG. 3D) were treated for 8 to 16 h with Lipofectin® alone, Lipofectin®-R-848 (1 μg/ml) or RNA (5 μg/ml). Modified nucleosides present in RNA-1571 are noted. TNF-α, IL-12(p70) and IFN-α were measured in the supernatant by ELISA. Mean values±SEM are shown. The results are representative of 10 (FIG. 3A and FIG. 3C), 4 (FIG. 3B), and 6 (FIG. 3D) independent experiments.
FIG. 3E. Activation of DC by RNA. MDDC were treated for 20 h with Lipofectin® alone or complexed with 1 μg/ml poly (I):(C) or R-848 as positive controls (top panel) or Lipofectin® complexed with the indicated RNA (5 μg/ml; bottom panel). Modified nucleosides present in RNA-1886 are noted. TNF-α was measured in the supernatants by ELISA. Expression of CD83, CD80, and HLA-DR was determined by flow cytometry.
Figure 3E:
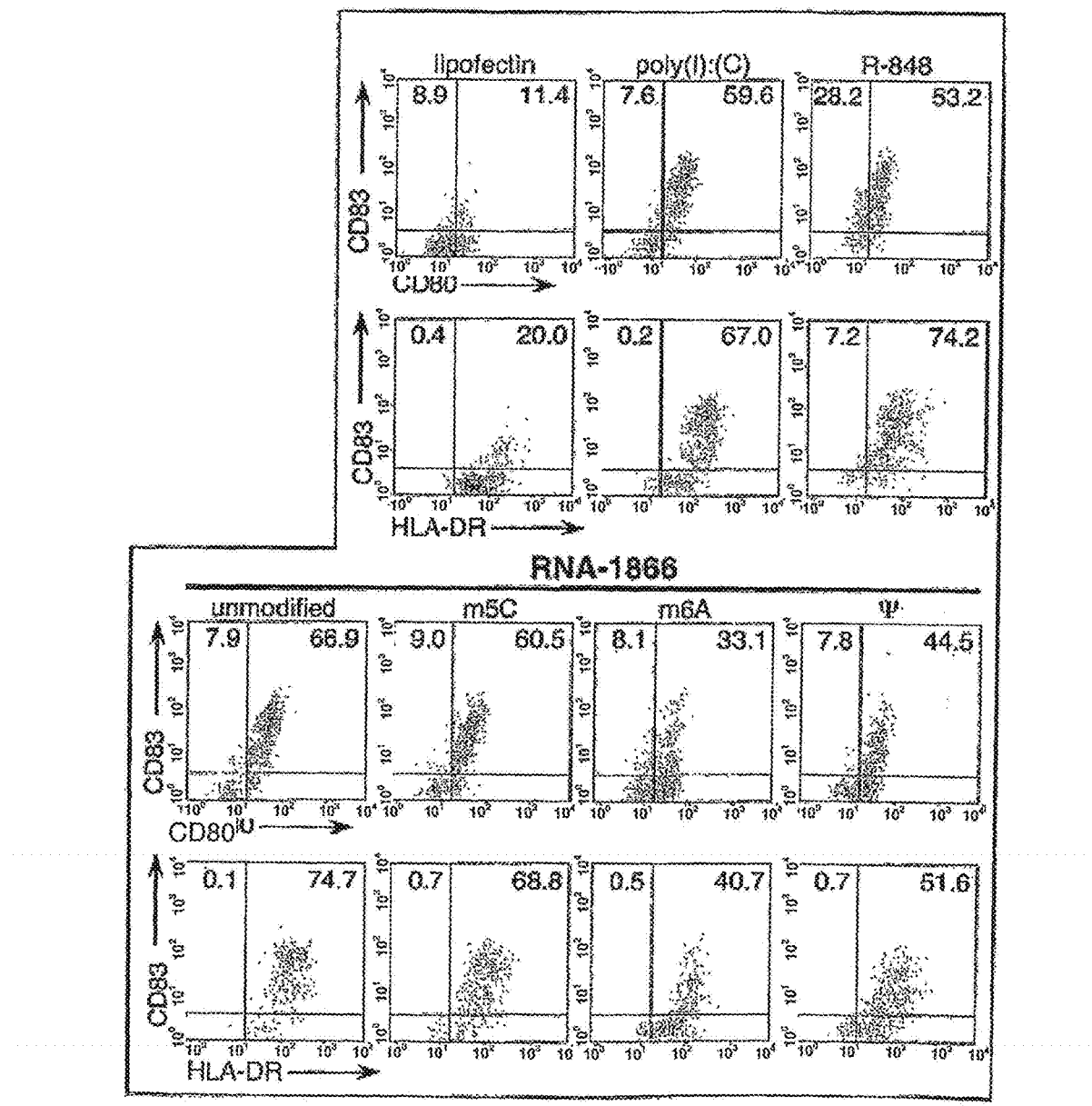

The next experiments tested the ability of RNA containing modified or unmodified nucleosides to stimulate cytokine-generated MDDC. Nucleoside modifications reproducibly diminished the ability of RNA to induce TNF-α and IL-12 secretion by both GM-CSF/IL-4-generated MDDC and (GM-CSF)/IFN-α-generated MDDC, in most cases to levels no greater than the negative control (FIGS. 3A and B). Results were similar when other sets of RNA with the same base modifications but different primary sequences and lengths were tested, or when the RNA was further modified by adding a 5' cap structure and/or 3'-end polyA-tail or by removing the 5' triphosphate moiety. RNAs of different length and sequence induced varying amounts of TNF-α from DC, typically less than a two-fold difference (FIG. 3C).

Next, the assay was performed on primary DC1 and DC2. Primary monocytoid (DC1, BDCA1$^+$) and plasmacytoid (DC2, BDCA4$^+$) DC were purified from peripheral blood. Both cell types produced TNF-α when exposed to R-848, but only DC1 responded to poly(I):(C), at a very low level, indicating an absence of TLR3 activity in DC2. Transfection of in vitro transcripts induced TNF-α secretion in both DC1 and DC2, while m5U, Ψ or s2U-modified transcripts were not stimulatory (FIG. 3D). In contrast to the cytokine-generated DC, m5C and m6A modification of RNA did not decrease its stimulatory capacity in the primary DC1 and DC2. Transcripts with m6A/Ψ double modification were non-stimulatory, while a mixture of RNA molecules with single type of modification (m6A+Ψ) was a potent cytokine inducer. Thus, uridine modification exerted a dominant suppressive effect on an RNA molecule in cis in primary DC. These results were consistent among all donors tested.

These findings show that in vitro-transcribed RNA stimulates cytokine production by DC. In addition, since DC2 do not express TLR3 or TLR8, and m5C and m6A modification of RNA decreased its stimulatory capacity of TLR7, these findings show that primary DC have an additional RNA signaling entity that recognizes m5C- and m6A-modified RNA and whose signaling is inhibited by modification of U residues.

Figures 4A, 4B:
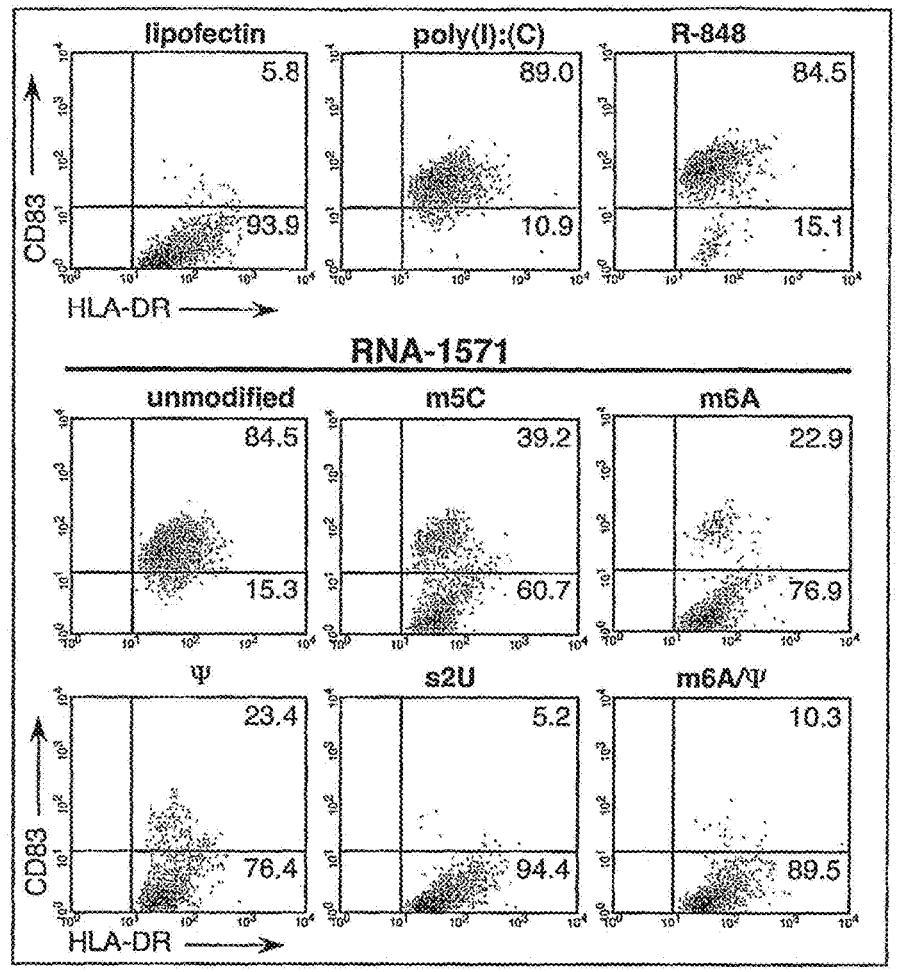
(FIG. 4A) CD83 and HLA-DR staining.
(FIG. 4B) TNF-α levels in the supernatants and mean fluorescence of CD80 and CD86 in response to incubation with RNA. The volume of medium was increased 30-fold for flow cytometry, as indicated by the asterisk. Data are representative of four independent experiments.

As additional immunogenicity indicators, cell surface expression of CD80, CD83, CD86 and MHC class II molecules, and secretion of TNF-α were measured by FACS analysis of MDDC treated with RNA-1571 and its modified versions. Modification of RNA with pseudouridine and modified nucleosides (m5C, m6A, s2U and m6APP) decreased these markers (FIG. 4), confirming the previous findings.

In summary, RNA's capacity to induce DCs to mature and secrete cytokines depends on the subtype of DC as well as on the characteristics of nucleoside modification present in the RNA. An increasing amount of modification decreases the immunogenicity of RNA.

Example 7: Suppression of RNA-Mediated Immune Stimulation is Proportional to the Number of Modified Nucleosides Present in RNA Materials and Experimental Methods Human DC For cytokine-generated DC, monocytes were purified from PBMC by discontinuous Percoll gradient centrifugation. The low density fraction (monocyte enriched) was depleted of B, T, and NK cells using magnetic beads (Dynal, Lake Success, N.Y.) specific for CD2, CD16, CD19, and CD56, yielding highly purified monocytes as determined by flow cytometry using anti-CD14 (>95%) or anti-CD11c (>98%) mAb.

To generate immature DC, purified monocytes were cultured in AIM V serum-free medium (Life Technologies), supplemented with GM-CSF (50 ng/ml)+IL-4 (100 ng/ml) (R & D Systems, Minneapolis, Minn.) in AIM V medium (Invitrogen) for the generation of monocyte-derived DC (MDDC) as described (Weissman, D et al, 2000. J Immunol 165: 4710-4717). DC were also generated by treatment with GM-CSF (50 ng/ml)+IFN-α (1,000 U/ml) (R & D Systems) to obtain IFN-α MDDC (Santini et al., 2000. Type I interferon as a powerful adjuvant for monocyte-derived dendritic cell development and activity in vitro and in Hu-PBL-SCID mice. J Exp Med 191: 1777-178).

Primary myeloid and plasmacytoid DCs (DC and DC2) were obtained from peripheral blood using BDCA-1 and BDCA-4 cell isolation kits (Miltenyi Biotec Auburn, Calif.), respectively.

Results

Figures 5A, 5B, 5C:
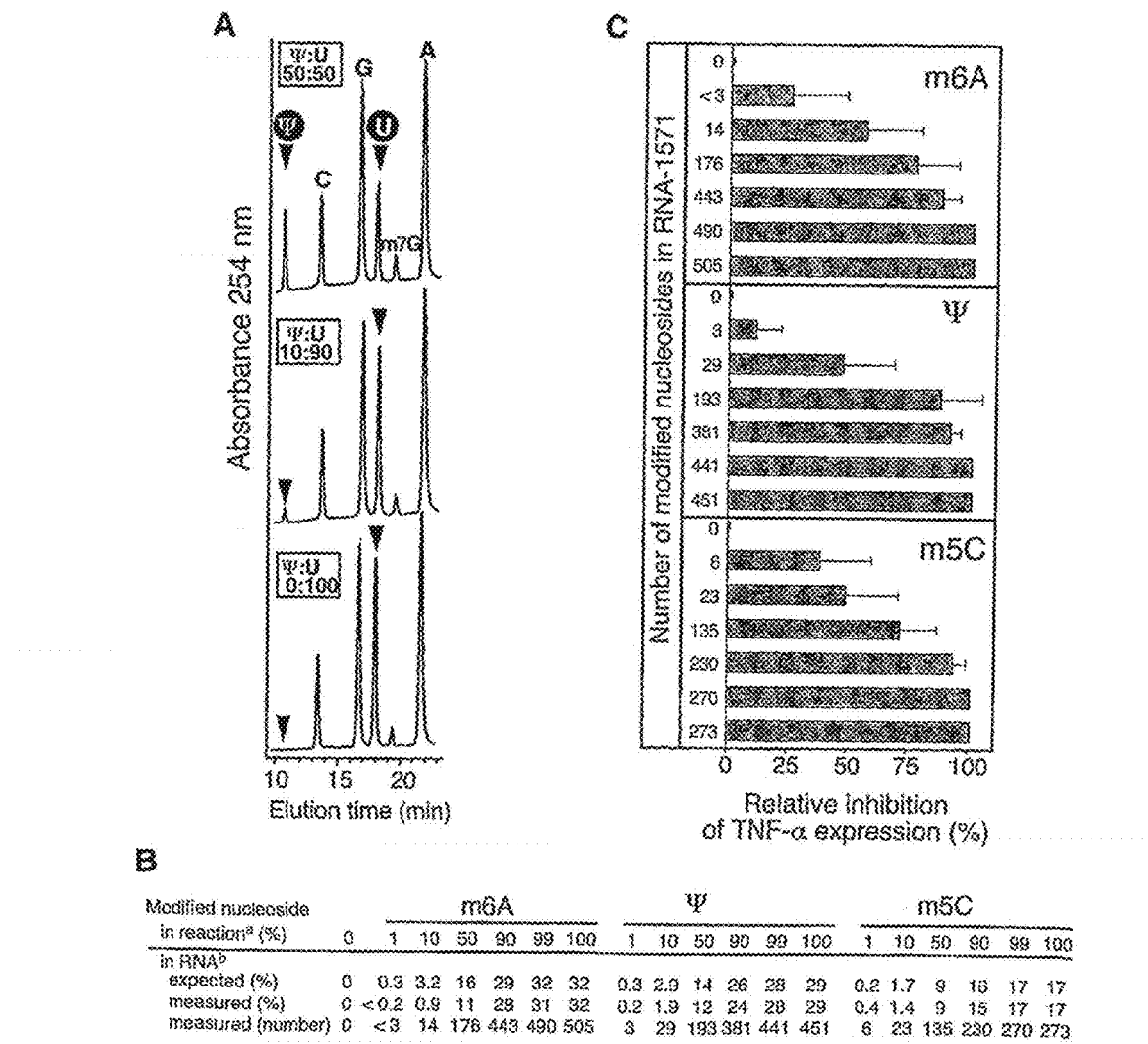
(FIG. 5A). All transcripts were digested to monophosphates and analyzed by reversed-phase HPLC to determine the relative amount of modified nucleoside incorporation. Representative absorbance profiles obtained at the indicated (Ψ:U) ratios are shown. Elution times are noted for 3'-monophosphates of pseudouridine (Ψ), cytidine (C), guanosine (G), uridine (U), 7-methylguanosine ("m7G") and adenosine ("A").
(FIG. 5B) Modified nucleoside content of RNA-1571. The expected percentage of $m^6A$, Ψ or $m^5C$ in RNA-1571 was calculated based on the relative amount of modified NTP in the transcription reaction and the nucleoside composition of RNA-1571 (A: 505, U: 451, C: 273, G: 342). Values for measured modified nucleoside content were determined based on quantitation of the HPLC chromatograms. Notes: A: values (%) for m6ATP, ΨTP and $m^5CTP$ relative to ATP UTP and CTP, respectively. B: values for $m^6A$, Ψ and $m^5C$ monophosphates relative to all NMPs.
(FIG. 5C) MDDC were transfected with Lipofectin®-complexed capped RNA-1571 (5 μg/ml) containing the indicated amount of m6A, Ψ or $m^5C$. After 8 h, TNF-α was measured in the supernatants. Data expressed as relative inhibition of TNF-α. Mean values±SEM obtained in 3 independent experiments are shown.

Most of the nucleoside-modified RNA utilized thus far contained one type of modification occurring in approximately 25% of the total nucleotides in the RNA (e.g. all the uridine bases). To define the minimal frequency of particular modified nucleosides that is sufficient to reduce immunogenicity under the conditions utilized herein, RNA molecules with limited numbers of modified nucleosides were generated. In the first set of experiments, RNA was transcribed in vitro in the presence of varying ratios of m6A, Ψ or m5C to their corresponding unmodified NTPs. The amount of incorporation of modified nucleoside phosphates into RNA was expected to be proportional to the ratio contained in the transcription reaction, since RNA yields obtained with T7 RNAP showed the enzyme utilizes NTPs of m6A, Ψ or m5C almost as efficiently as the basic NTPs. To confirm this expectation, RNA transcribed in the presence of UTP:Ψ in a 50:50 ratio was digested and found to contain UMP and Ψ in a nearly 50:50 ratio (FIG. 5A).

RNA molecules with increasing modified nucleoside content were transfected into MDDC, and TNF-α secretion was assessed. Each modification (m6A, Ψ and m5C) inhibited TNF-α secretion proportionally to the fraction of modified bases. Even the smallest amounts of modified bases tested (0.2-0.4%, corresponding to 3-6 modified nucleosides per 1571 nt molecule), was sufficient to measurably inhibit cytokine secretion (FIG. 5B). RNA with of 1.7-3.2% modified nucleoside levels (14-29 modifications per molecule) exhibited a 50% reduction in induction of TNF-α expression. In TLR-expressing 293 cells, a higher percentage (2.5%) of modified nucleoside content was required to inhibit RNA-mediated signaling events.

Thus, pseudouridine and modified nucleosides reduce the immunogenicity of RNA molecules, even when present as a small fraction of the residues.

Figures 6A, 6B, 6C:
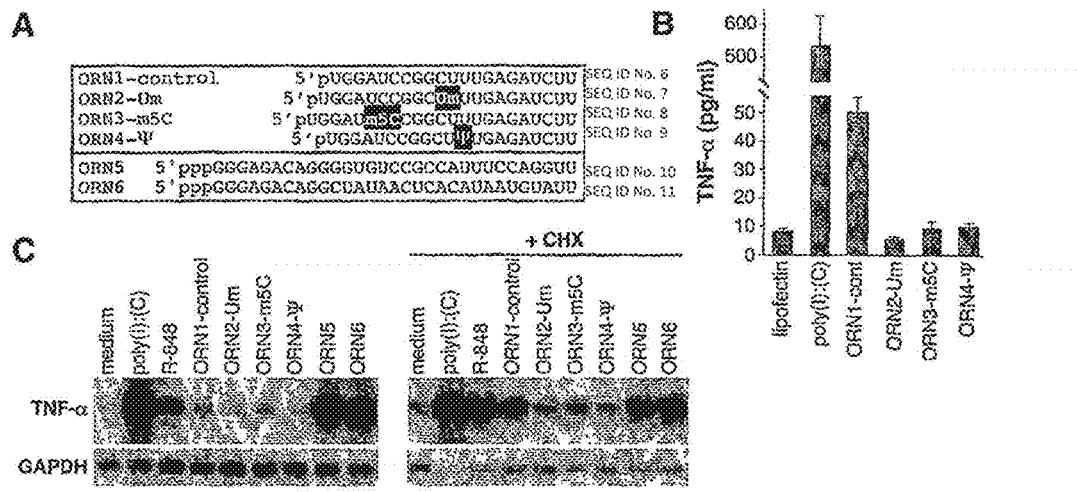
(FIG. 6A) Sequences of oligoribonucleotides (ORN) synthesized chemically (ORN1-4) or transcribed in vitro (ORN5-6) are shown. Positions of modified nucleosides Um (2'-O-methyluridine), $m^5C$ and P are highlighted. Human MDDC were transfected with Lipofectin® alone (medium), R-848 (1 μg/ml) or Lipofectin® complexed with RNA (5 μg/ml). Where noted, cells were treated with 2.5 μg/ml cycloheximide (CHX).
(FIG. 6B). After 8 h incubation, TNF-α was measured in the supernatant.
(FIG. 6C) RNA from the cells was analyzed by Northern blot. Representative mean values±SEM of 3 independent experiments are shown.

In additional experiments, 21-mer oligoribonucleotides (ORN) with phosphodiester inter-nucleotide linkages were synthesized wherein modified nucleosides (m5C, Ψ or 2'-O-methyl-U [Um]) were substituted in a particular position (FIG. 6A). While the unmodified ORN induced TNF-α secretion, this effect was abolished by the presence of a single nucleoside modification (FIG. 6B). Similar results were obtained with TLR-7 and TLR-8-transformed 293 cells expressing TLR3-targeted siRNA.

The above results were confirmed by measuring TNF-α mRNA levels in MDDC by Northern blot assay, using both the above 21-mer ORN (ORN1) and 31-mer in vitro-synthesized transcripts (ORN5 and ORN6). To amplify the signal, cycloheximide, which blocks degradation of selected mRNAs, was added to some samples, as indicated in the Figure. The unmodified ODN increased TNF-α mRNA levels, while ORNs containing a single modified nucleoside were significantly less stimulatory; ORN2-Um exhibited the greatest decrease TNF-α production (FIG. 6C).

Similar results were observed in mouse macrophage-like RAW cells and in human DC.

In summary, each of the modifications tested (m6A, m5C, m5U, s2U, Ψ and 2'-O-methyl) suppressed RNA-mediated immune stimulation, even when present as a small fraction of the residues. Further suppression was observed when the proportion of modified nucleosides was increased.

Example 8: Pseudouridine-Modification of RNA Reduces its Immunogenicity In Vivo

Figure 7A:
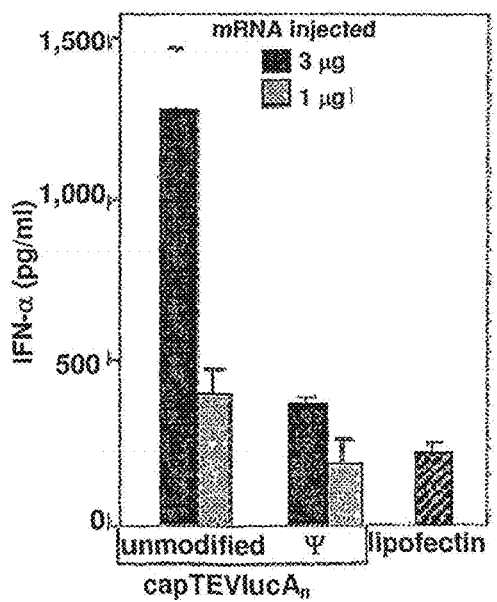
(FIG. 7A) ψmRNA does not stimulate pro-inflammatory cytokine production in vivo. Serum samples (6 h after injection) were analyzed by ELISA and revealed that 3 μg of unmodified mRNA induced a higher level of IFN-α than did 3 μg of ψ-modified mRNA (P<0.001). Levels of IFN-α induced by 3 μg of ψ-modified mRNA were similar to those obtained when animals were injected with uncomplexed lipofectin. Values are expressed as the mean±s.e.m. (n=3 or 5 animals/group).
Figure 7B:
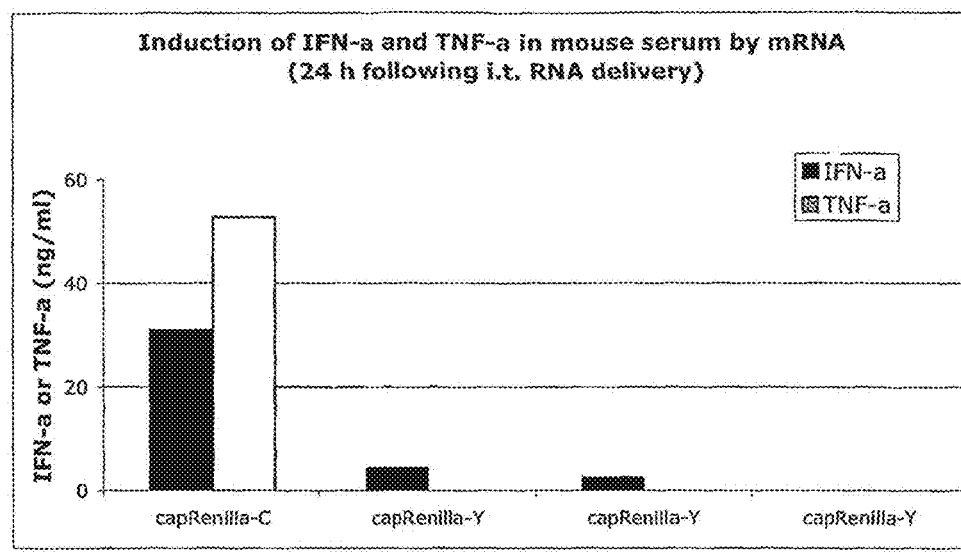
(FIG. 7B) Similar results were observed with TNF-α.

To determine the effect of pseudouridine modification on immunogenicity of RNA in vivo, 0.25 μg RNA) was complexed to Lipofectin® and injected intratracheally into mice, mice were bled 24 h later, and circulating levels of TNF-α and IFN-α were assayed from serum samples. Capped, pseudouridine-modified mRNA induced significantly less TNF-α and IFN-α mRNA than was elicited by unmodified mRNA (FIG. 7A-B).

These results provide further evidence that pseudouridine-modified mRNA is significantly less immunogenic in vivo than unmodified RNA.

Example 9: Pseudouridine-Containing RNA Exhibits Decreased Ability to Activate PRK Materials and Experimental Methods PKR Phosphorylation Assays Aliquots of active PKR agarose (Upstate) were incubated in the presence of magnesium/ATP cocktail (Upstate), kinase buffer and [gamma$^{32}$P] ATP mix and RNA molecules for 30 min at 30° C. Unmodified RNA and RNA with nucleoside modification (m5C, pseudouridine, m6A, m5U) and dsRNA were tested. Human recombinant eIF2α (BioSource) was added, and samples were further incubated for 5 min, 30° C. Reactions were stopped by adding NuPage LDS sample buffer with reducing reagent (Invitrogen), denatured for 10 min, 70° C., and analyzed on 10% PAGE. Gels were dried and exposed to film. Heparin (1 U/μl), a PKR activator, was used as positive control.

Results

Figure 8:
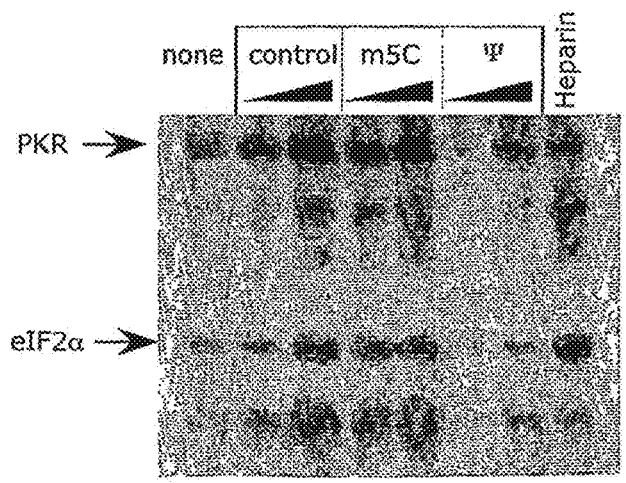
FIG. 8. mRNA containing pseudouridine (Ψ) does not activate PKR. Ψ: pseudouridine. Control: unmodified RNA. m5C: mRNA with $m^5C$ modification.

To determine whether pseudouridine-containing mRNA activates dsRNA-dependent protein kinase (PKR), in vitro phosphorylation assays were performed using recombinant human PKR and its substrate, eIF2α (eukaryotic initiation factor 2 alpha) in the presence of capped, renilla-encoding mRNA (0.5 and 0.05 ng/μl). mRNA containing pseudouridine (Ψ) did not activate PKR, as detected by lack of both self-phosphorylation of PKR and phosphorylation of eIF2α, while RNA without nucleoside modification and mRNA with m⁵C modification activated PKR (FIG. 8). Thus, pseudouridine modification decreases RNA immunogenicity.

Example 10: Enhanced Translation of Proteins from Pseudouridine and m⁵C-Containing RNA In Vitro Materials and Experimental Methods In Vitro Translation of mRNA in Rabbit Reticulocyte Lysate In vitro-translation was performed in rabbit reticulocyte lysate (Promega, Madison Wis.). A 9-μl aliquot of the lysate was supplemented with 1 μl (1 μg) mRNA and incubated for 60 min at 30° C. One μl aliquot was removed for analysis using firefly and *renilla* assay systems (Promega, Madison Wis.), and a LUMAT LB 950 luminometer (Berthold/EG&G Wallac, Gaithersburg, Md.) with a 10 sec measuring time.

Results

Figure 9:
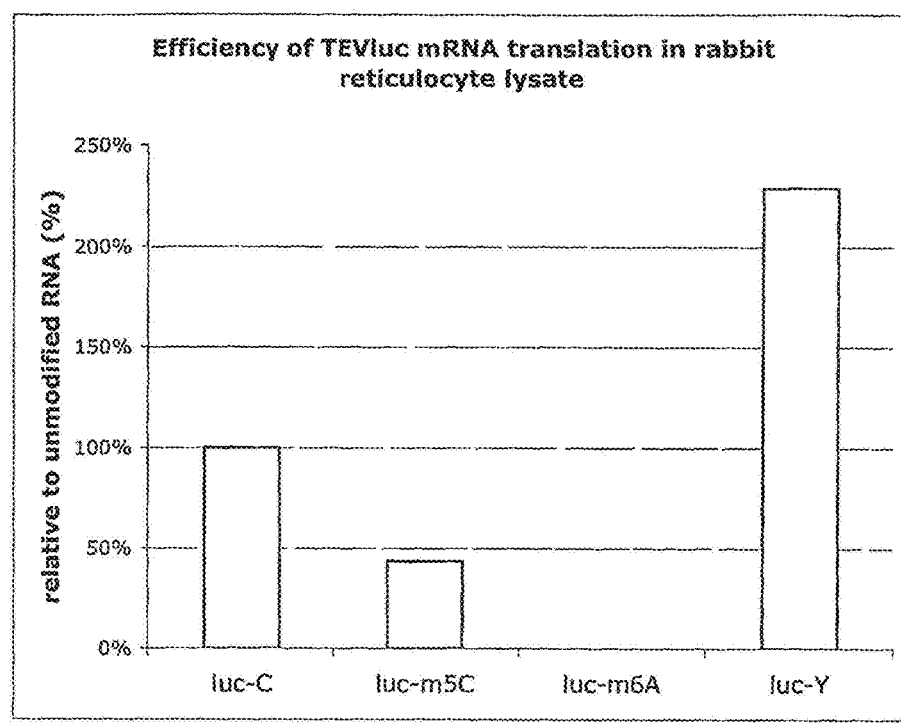
FIG. 9. Increased expression of luciferase from pseudouridine-containing mRNA in rabbit reticulocyte lysate. Luc-Y: mRNA with pseudouridine modification; luc-C: unmodified RNA. Data is expressed by normalizing luciferase activity to unmodified luciferase RNA.

To determine the effect of pseudouridine modification on RNA translation efficiency in vitro, (0.1 μg/μl) uncapped mRNA modified with pseudouridine encoding firefly luciferase was incubated in rabbit reticulocyte lysate for 1 h at 30° C., and luciferase activity was determined. mRNA containing pseudouridine was translated more than 2-fold more efficiently than RNA without pseudouridine in rabbit reticulocyte lysates, but not in wheat extract or *E. coli* lysate (FIG. 9), showing that pseudouridine modification increases RNA translation efficiency. Similar results were obtained with m⁵C-modified RNA. When a polyA tail was added to pseudouridine-containing mRNA, a further 10-fold increase in translation efficiency was observed. (Example 10).

Thus, pseudouridine and m⁵C modification increases RNA translation efficiency, and addition of a polyA tail to pseudouridine-containing mRNA further increases translation efficiency.

Example 11: Enhanced Translation of Proteins from Pseudouridine-Containing RNA in Cultured Cells Materials and Experimental Methods Translation Assays in Cells Plates with 96 wells were seeded with $5 \times 10^4$ cells per well 1 day before transfection. Lipofectin®-mRNA complexes were assembled and added directly to the cell monolayers after removing the culture medium (0.2 μg mRNA-0.8 μg lipofectin in 50 μl per well). Cells were incubated with the transfection mixture for 1 h at 37° C., 5% CO₂ incubator, then the mixture was replaced with fresh, pre-warmed medium containing 10% FCS, then cells were analyzed as described in the previous Example.

Results

Figure 10A:
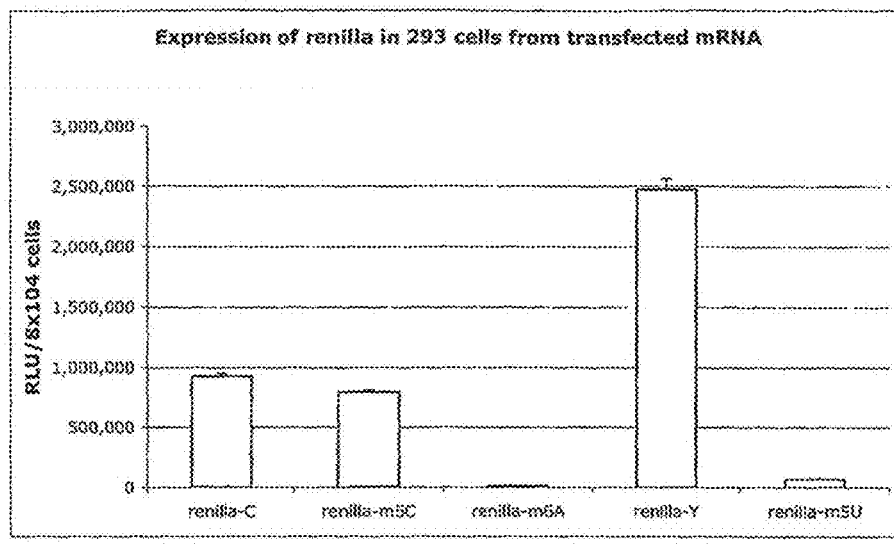
FIG. 10A. 293 cells.

To determine the effect of pseudouridine modification on RNA translation in cultured cells, 293 cells were transfected with in vitro-transcribed, nucleoside-modified, capped mRNA encoding the reporter protein *renilla*. Cells were lysed 3 h after initiation of transfection, and levels of *renilla* were measured by enzymatic assays. In 293 cells, pseudouridine- and m5C-modified DNA were translated almost 10 times and 4 times more efficiently, respectively, than unmodified mRNA (FIG. 10A).

Figure 10B:
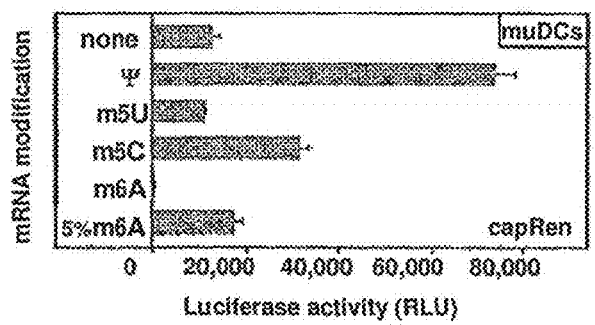
FIG. 10B. Murine primary, bone marrow-derived mouse dendritic cells. renilla-Y: mRNA with pseudouridine modification; renilla-C: unmodified RNA. RNA was modified with $m^5C$, $m^6A$, and $m^5U$ as noted.

Next, the experiment was performed with primary, bone marrow-derived mouse DC, in this case lysing the cells 3 h and 8 h after transfection. RNA containing the pseudouridine modification was translated 15-30 times more efficiently than unmodified RNA (FIG. 10B).

Similar expression results were obtained using human DC and other primary cells and established cell lines, including CHO and mouse macrophage-like RAW cells. In all cell types, pseudouridine modification produced the greatest enhancement of the modifications tested.

Thus, pseudouridine modification increased RNA translation efficiency in all cell types tested, including different types of both professional antigen-presenting cells and non-professional antigen-presenting cells, providing further evidence that pseudouridine modification increases the efficiency of RNA translation.

Figure 11A:
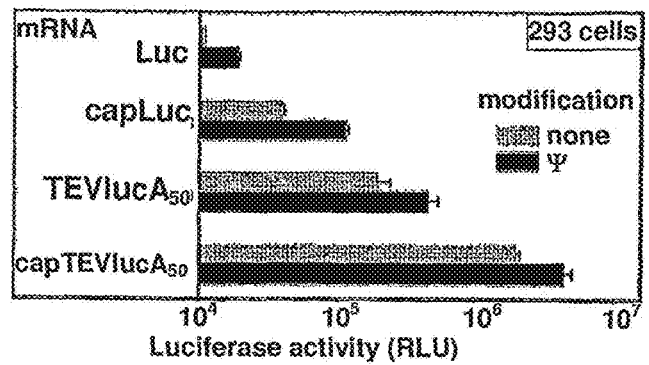
FIG. 11A. Additive effect of 3' and 5' elements on translation efficiency of ψmRNA. 293 cells were transfected with firefly luciferase conventional and ψmRNAs that had 5' cap (capLuc), 50 nt-long 3' polyA-tail (TEVlucA50), both or neither of these elements (capTEVlucA50 and Luc, respectively). Cells were lysed 4 h later and luciferase activities measured in aliquots (1/20th) of the total lysates.

Example 12: 5' and 3' Elements Further Enhance the Translation of ψmRNA in Mammalian Cells To test the effect of additional RNA structural elements on enhancement of translation by pseudouridine modification, a set of firefly luciferase-encoding ψmRNAs were synthesized that contained combinations of the following modifications: 1) a unique 5' untranslated sequence (TEV, a cap independent translational enhancer), 2) cap and 3) polyA-tail. The ability of these modifications to enhance translation of ψmRNA or conventional mRNA was assessed (FIG. 11A). These structural elements additively enhanced translational efficiency of both conventional and ψmRNA, with ψmRNA exhibiting greater protein production from all constructs.

Figure 11B:
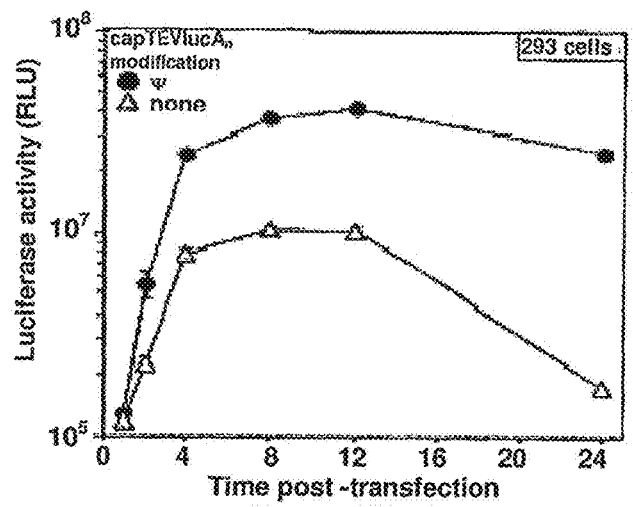
FIG. 11B. ψmRNA is more stable than unmodified mRNA. 293 cells transfected with capTEVlucA$_n$ containing unmodified or ψ-modified nucleosides were lysed at the indicated times following transfection. Aliquots (1/20th) of the lysates were assayed for luciferase. Standard errors are too small to be visualized with error bars.

Ability of protein expression from the most efficient firefly luciferase ψmRNA construct, capTEVlucA50 (containing TEV, cap, and an extended poly(A) tail) was next examined over 24 hours in 293 cells (FIG. 11B). ψmRNA produced more protein at every time point tested and conferred more persistent luciferase expression than equivalent conventional mRNA constructs, showing that ψ-modifications stabilize mRNA.

Figure 11C:
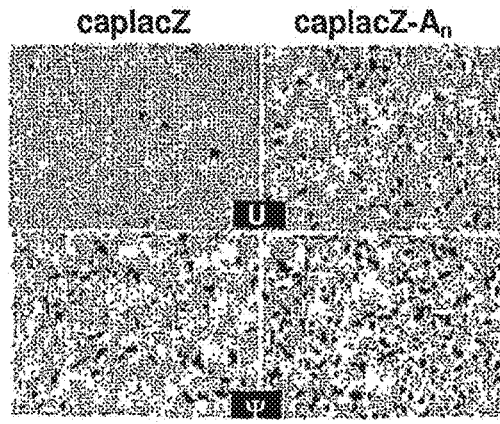
FIG. 11C. Expression of β-galactosidase is enhanced using ψmRNA compared with conventional mRNA. 293 cells seeded in 96-well plates were transfected with lipofectin-complexed mRNAs (0.25 μg/well) encoding bacterial β-galactosidase (lacZ). The transcripts had cap and 3' polyA-tail that were either 30 nt-long (caplacZ) or ~200 nt-long (caplacZ-An). Constructs made using conventional U or w nucleosides were tested. Cells were fixed and stained with X-gal, 24 h post-transfection. Images were taken by inverted microscopy (40 and 100× magnification) from representative wells.

To test whether ψ-modification of mRNA improved translation efficiency in mammalian cells in situ, caplacZ-ψmRNA constructs with or without extended polyA-tails ($A_n$) and encoding β-galactosidase (lacZ) were generated and used to transfect 293 cells. 24 h after mRNA delivery, significant increases in β-galactosidase levels were detected by X-gal visualization, in both caplacZ and caplacZ-$A_n$, compared to the corresponding control (conventional) transcripts (FIG. 11C). This trend was observed when either the number of cells expressing detectable levels of β-galactosidase or the signal magnitude in individual cells was analyzed.

Example 13: Enhanced Translation of Proteins from Pseudouridine-Containing RNA In Vivo Materials and Experimental Methods Intracerebral RNA Injections All animal procedures were in accordance with the *NIH Guide for Care and Use of Laboratory Animals* and approved by the Institutional Animal Care and Use Committee. Male Wistar rats (Charles River Laboratories, Wilmington, Mass.) were anesthetized by intraperitoneal injection of sodium pentobarbital (60 mg/kg body weight). Heads were placed in a stereotaxic frame, and eight evenly spaced 1.5 mm diameter burr holes were made bilaterally [coordinates relative to bregma: anterior/posterior +3, 0, −3, −6 mm; lateral ±2.5 mm] leaving the dura intact. Intracerebral injections were made using a 25 μl syringe (Hamilton, Reno, Nev.) with a 30 gauge, 1 inch sterile needle (Beckton Dickinson Labware, Franklin Lakes, N.J.) which was fixed to a large probe holder and stereotactic arm. To avoid air space in the syringe, the needle hub was filled with 55 µl complex before the needle was attached, and the remainder of the sample was drawn through the needle. Injection depth (2 mm) was determined relative to the surface of the dura, and 4 µl complex (32 ng mRNA) was administered in a single, rapid bolus infusion. 3 hours (h) later, rats were euthanized with halothane, and brains were removed into chilled phosphate buffered saline.

Injection of RNA into Mouse Tail Vein

Tail veins of female BALB/c mice (Charles River Laboratories) were injected (bolus) with 60 µl Lipofectin®-complexed RNA (0.26 µg). Organs were removed and homogenized in luciferase or Renilla lysis buffer in microcentrifuge tubes using a pestle. Homogenates were centrifuged, and supernatants were analyzed for activity.

Delivery of RNA to the Lung

Female BALB/c mice were anaesthetized using ketamine (100 mg/kg) and xylasine (20 mg/kg). Small incisions were made in the skin adjacent to the trachea. When the trachea was exposed, 50 µl of Lipofectin®-complexed RNA (0.2 µg) was instilled into the trachea towards the lung. Incisions were closed, and animals allowed to recover. 3 hours after RNA delivery, mice were sacrificed by cervical dislocation and lungs were removed, homogenized in luciferase or Renilla lysis buffer (250 µl), and assayed for activity. In a different set of animals, blood samples (100 µl/animal) were collected from tail veins, clotted, and centrifuged. Serum fractions were used to determine levels of TNF and IFN$\alpha$ by ELISA as described in the Examples above, using mouse-specific antibodies.

Results

To determine the effect of pseudouridine modification on RNA translation in vivo, each hemisphere of rat brain cortexes was injected with either capped, renilla-encoding pseudouridine-modified RNA or unmodified RNA, and RNA translation was measured. Pseudouridine-modified RNA was translated significantly more efficiently than unmodified RNA (FIG. 12A).

Next, expression studies were performed in mice. Firefly luciferase-encoding mRNAs because no endogenous mammalian enzyme interferes with its detection. Transcripts (unmodified and ψmRNA) were constructed with cap, TEV (capTEVA$_{50}$) and extended (~200 nt) poly(A) tails. 0.25 µg RNA Lipofectin®-complexed was injected into mice (intravenous (i.v.) tail vein). A range of organs were surveyed for luciferase activity to determine the optimum measurement site. Administration of 0.3 µg capTEVlucAn ψmRNA induced high luciferase expression in spleen and moderate expression in bone marrow, but little expression in lung, liver, heart, kidney or brain (FIG. 12B). In subsequent studies, spleens were studied.

Figure 12C:
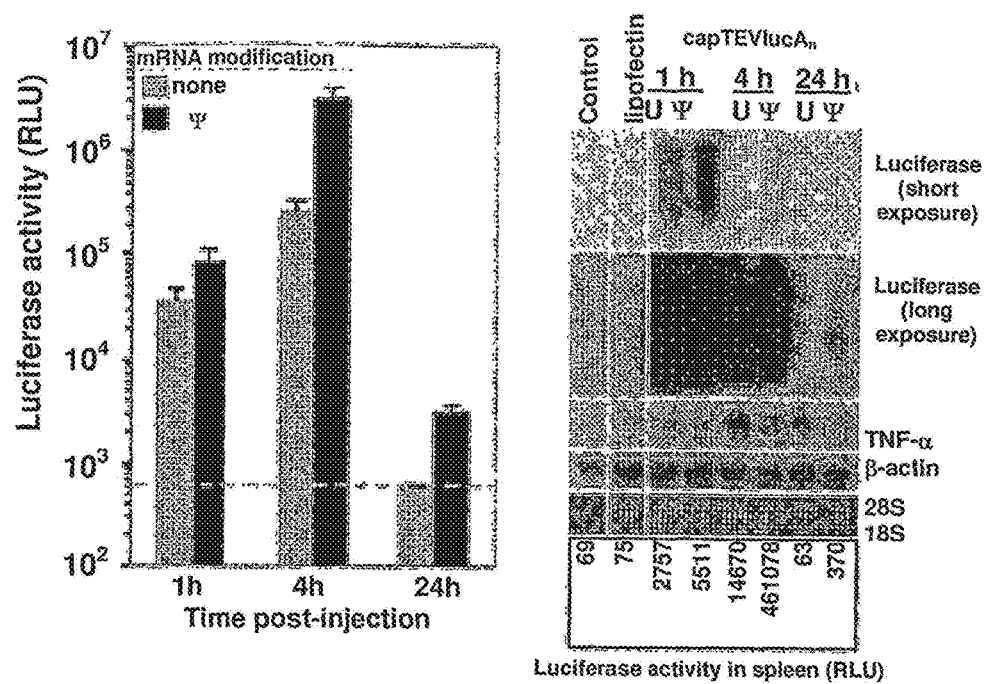
FIG. 12C. ψmRNA exhibits greater stability and translation in vivo. Lipofectin-complexed capTEVlucAn (0.3 μg/60 μl/animal) with or without N modifications was delivered i.v. to mice. Animals were sacrificed at 1, 4 and 24 h post-injection, and ½ of their spleens were processed for luciferase enzyme measurements (left panel) and the other half for RNA analyses (right panel). Luciferase activities were measured in aliquots (1/5th) of the homogenate made from half of the spleens. Plotted values represent luciferase activities in the whole spleen and are expressed as the mean±s.e.m. (n=3 or 4/point).

Translation efficiencies of conventional and ψmRNA (0.015 mg/kg; 0.3 µg/animal given intravenously) were next compared in time course experiments. Luciferase activity was readily detectable at 1 h, peaked at 4 h and declined by 24 h following administration of either conventional or ψmRNA, but at all times was substantially greater in animals given ψmRNA (FIG. 12C, left panel). By 24 h, only animals injected with ψmRNA demonstrated detectable splenic luciferase activity (4-fold above background). A similar relative pattern of expression (between modified and unmodified mRNA) was obtained when mRNAs encoding Renilla luciferase (capRen with or without ψ modifications) were injected into the animals instead of firefly luciferase, or when isolated mouse splenocytes were exposed to mRNA in culture.

Figure 12D:
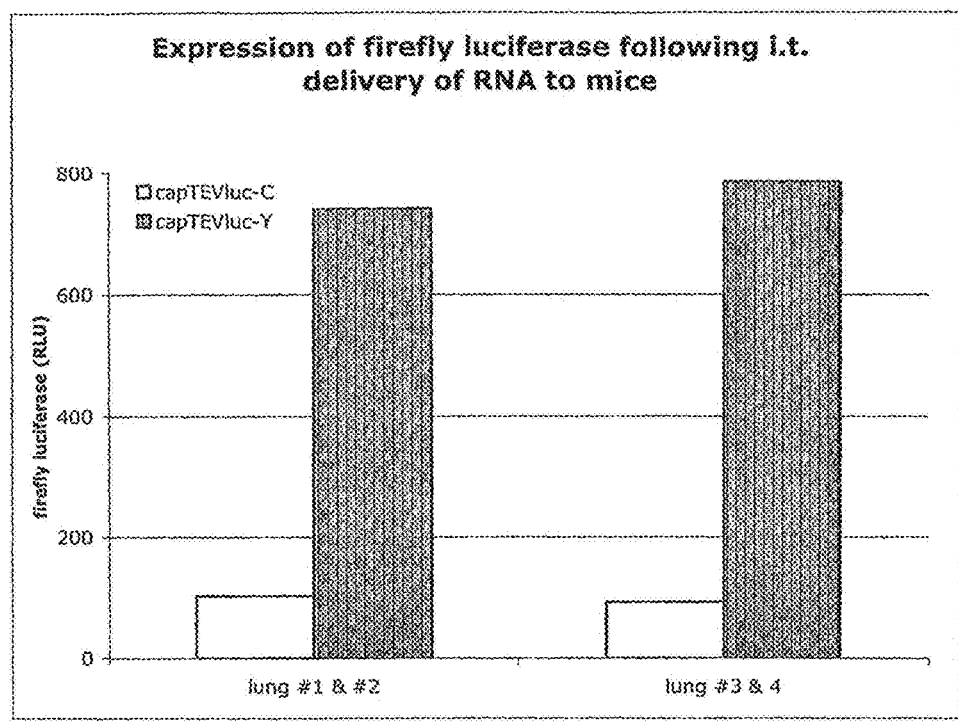
FIG. 12D. Expression of firefly luciferase following intratracheal injection of mRNA. capTEVluc-Y: capped, firefly luciferase-encoding pseudouridine-modified RNA. CapTEVluc-C: capped RNA with no nucleoside modification.

In the next experiment, 0.25 µg mRNA-Lipofectin® was delivered to mouse lungs by intra-tracheal injection. Capped, pseudouridine-modified RNA was translated more efficiently than capped RNA without pseudouridine modification (FIG. 12D).

Thus, pseudouridine modification increases RNA translation efficiency in vitro, in cultured cells, and in vivo—in multiple animal models and by multiple routes of administration, showing its widespread application as a means of increasing the efficiency of RNA translation.

Example 14: Pseudouridine Modification Enhances RNA Stability In Vivo

Northern analyses of splenic RNA at 1 and 4 h post injection in the animals from the previous Example revealed that the administered mRNAs, in their intact and partially degraded forms, were readily detectable (FIG. 12C, right panel). By contrast, at 24 h, unmodified capTEVlucAn mRNA was below the level of detection, while capTEVlucAn ψmRNA, though partially degraded, was still clearly detectable. Thus, ψmRNA is more stably preserved in vivo than control mRNA.

Figure 13:
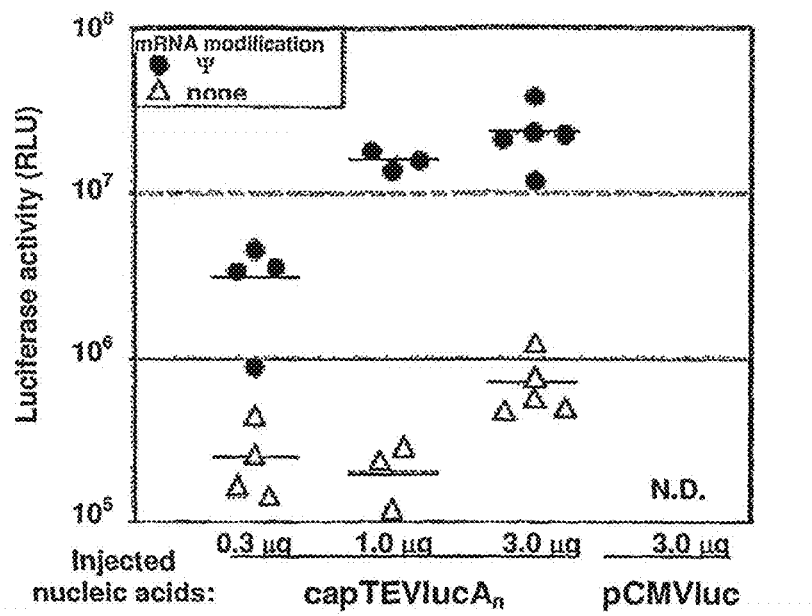
FIG. 13. Protein production is dependent on the amount of mRNA delivered intravenously in mice. The indicated amounts of lipofectin-complexed nucleic acids, capTEVlucAn mRNA with or without ψ constituents and pCMVluc plasmid DNA in a volume of 60 μl/animal were delivered by i.v. injection into mice. Animals injected with mRNA or plasmid DNA were sacrificed at 6 h or 24 h post-injection, respectively, and luciferase activities were measured in aliquots (1/10th) of their spleens homogenized in lysis buffer. The value from each animal is shown, and short horizontal lines indicate the mean; N.D., not detectable.

To test whether in vivo protein production is quantitatively dependent on the concentration of intravenously-delivered mRNA, mRNAs were administered to mice at 0.015-0.150 mg/kg (0.3-3.0 µg capTEVlucAn per animal) and spleens were analyzed 6 hours later as described above. Luciferase expression correlated quantitatively with the amount of injected RNA (FIG. 13) and at each concentration.

These findings confirm the results of Example 12, demonstrating that ψmRNA is more stable than unmodified RNA.

Further immunogenicity of ψ-mRNA was less than unmodified RNA, as described hereinabove (FIG. 7 and FIG. 12C, right panel).

To summarize Examples 13-14, the 3 advantages of ψ-mRNA compared with conventional mRNA (enhanced translation, increased stability and reduced immunogenicity) observed in vitro are also observed in vivo.

Figure 14:
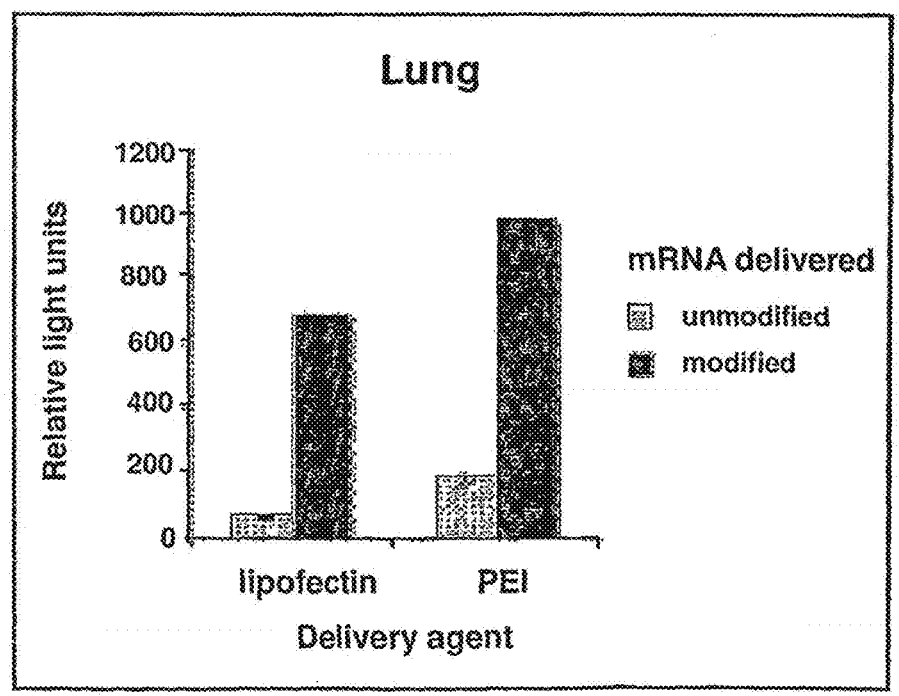
FIG. 14. Expression of firefly luciferase following intratracheal delivery of encoding mRNA. mRNA were complexed to lipofectin (or PEI, as noted) and animals were injected with 0.3 µg firefly luciferase-encoding mRNA with or without ψ modification, then sacrificed 3 hours later. Lungs were harvested and homogenized, and luciferase activity was measured in aliquots of the lysed organs.
Figure 15:
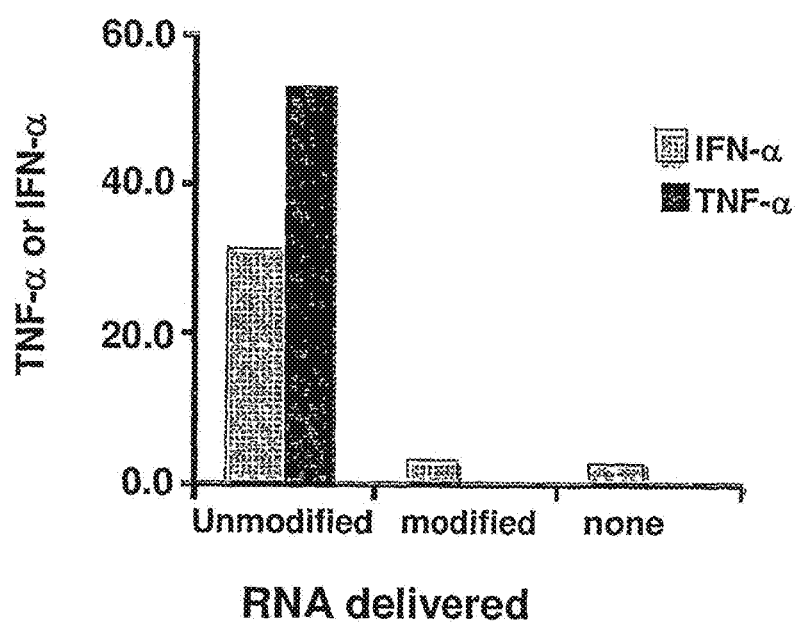
FIG. 15. ψmRNA does not induce inflammatory mediators after pulmonary delivery. Induction of TNF-α and IFN-α in serum following intratracheal delivery of luciferase-encoding mRNA or ψmRNA. Serum levels of TNF-α and IFN-α were determined by ELISA 24 hours after mRNA delivery.

Example 15: ψmRNA Delivered Via the Respiratory Tract Behaves Similarly to Intravenously Administered mRNA To test the ability of ψmRNA to be delivered by inhalation, Lipofectin®- or PEI-complexed mRNAs encoding firefly luciferase were delivered to mice by the intratracheal route, wherein a needle was placed into the trachea and mRNA solution sprayed into the lungs. Similar to intravenous delivery, significantly greater luciferase expression was observed with ψmRNA compared to unmodified mRNA (FIG. 14), although significantly less protein was produced with the intratracheal as compared to the intravenous routes. Unmodified mRNA administered by the intratracheal route was associated with significantly higher concentrations of inflammatory cytokines (IFN-$\alpha$ and TNF-$\alpha$) compared with vehicle controls, while ψmRNA was not (FIG. 15).

Thus, ψmRNA can be delivered by inhalation without activating the innate immune response.

Example 16: Delivery of EPO-ψmRNA to 293 Cells

ψmRNA was generated from a plasmid containing the human EPO cDNA. When 0.25 μg of EPO-ψmRNA was transfected into $10^6$ cultured 293 cells, greater than 600 mU/ml of EPO protein was produced. Thus, modified RNA molecules of the present invention are efficacious at delivering recombinant proteins to cells.

Example 17: Preparation of Improved EPO-Encoding ψmRNA Constructs

Materials and Experimental Methods

The EPO coding sequence is cloned using restriction enzyme techniques to generate 2 new plasmids, pTEV-EPO and pT7TS-EPO, that are used as templates for EPO-ψmRNA production. EPO-ψmRNAs will are produced from these templates by in vitro transcription (MessageMachine® and MegaScript® kits; Ambion) using T7 RNA polymerase (RNAP), incorporating nucleosides at equimolar (7.5 mM) concentrations. To incorporate the nucleoside-modifications, ψ triphosphate (TriLink, San Diego, Calif.) replaces UTP in the transcription reaction. To ensure capping of the ψmRNA, a non-reversible cap-analog, 6 mM 3'-O-Me-m7GpppG (New England BioLabs, Beverly, Mass.) is also included. The ψmRNAs are poly(A)-tailed in a reaction of ~1.5 μg/μl RNA, 5 mM ATP, and 60 U/μl yeast poly(A) polymerase (USB, Cleveland, Ohio) mixed at 30° C. for 3 to 24 h. Quality of ψmRNAs is assessed by denaturing agarose gel electrophoresis. Assays for LPS in mRNA preparations using the Limulus Amebocyte Lysate gel clot assay with a sensitivity of 3 pg/ml are also performed.

Results

The proximal 3'-untranslated region (3'UTR) of EPO-ψmRNA preserves a ~90 nt-long pyrimidine-rich stabilizing element from the nascent EPO mRNA, which stabilizes EPO mRNA by specific association with a ubiquitous protein, erythropoietin mRNA-binding protein (ERBP). To maximize the stability of EPO-ψmRNA, 2 alterations are incorporated into the EPO plasmid to improve the stability and translational efficiency of the transcribed mRNA: 1) A 5'UTR sequence of the tobacco etch virus (TEV) is incorporated upstream of the EPO coding sequence to generate pTEV-EPO. 2) A plasmid, pT7TS-EPO, is generated, wherein the EPO cDNA is flanked by sequences corresponding to β-globin 5' and 3'UTRs.

In addition, the length of the poly(A) tail during the production of ψmRNA from these plasmid templates is extended, by increasing the incubation period of the poly(A) polymerase reaction. The longer poly(A) tail diminishes the rate at which ψmRNA degrades during translation.

These improvements result in enhanced translation efficiency in vivo, thus minimizing the therapeutic dose of the final product.

Example 18: In Vitro Analysis of Protein Production from EPO mRNA Constructs Materials and Experimental Methods Preparation of Mammalian Cells.

Human embryonic kidney 293 cells (ATCC) are propagated in DMEM supplemented with glutamine (Invitrogen) and 10% FCS (Hyclone, Ogden, Utah) (complete medium). Leukopheresis samples are obtained from HIV-uninfected volunteers through an IRB-approved protocol. DCs are produced as described above and cultured with GM-CSF (50 ng/ml)+IL-4 (100 ng/ml) (R & D Systems) in AIM V Medium® (Invitrogen).

Murine spleen cells and DC are obtained by published procedures. Briefly, spleens from BALB/c mice are aseptically removed and minced with forceps in complete medium. Tissue fragments are sedimented by gravity and the single cell suspension washed and lysed with AKC lysis buffer (Sigma). Murine DCs are derived from bone marrow cells collected from femurs and tibia of 6-9-week-old BALB/c mice. Cells are cultured in DMEM containing 10% FCS (Invitrogen) and 50 ng/ml muGM-CSF (R&D) and used on day 7.

Transfection of Cells and Detection of EPO and Pro-Inflammatory Cytokines

Transfections are performed with Lipofectin in the presence of phosphate buffer, an effective delivery method for splenic and in vitro cell expression. EPO-ψmRNA (0.25 μg/well; 100,000 cells) is added to each cell type in triplicate for 1 hour, and supernatant replaced with fresh medium. 24 hours later, supernatant is collected for ELISA measurement of EPO, IFN-α or β, and TNF-α.

Results

To evaluate the impact of unique UTRs on enhancement of ψmRNA translational efficiency, EPO-ψmRNA containing, or not containing, each improvement (5' TEV element, β-globin 5' and 3'UTRs) with long poly(A) tails are tested for in vitro protein production and in vitro immune activation, with. EPO conventional-nucleoside mRNA used as controls. Efficiency of protein production from each mRNA is assessed in mammalian cell lines, (HEK293, CHO), human and murine primary DCs, and spleen cells for each mRNA. Measurement of total EPO produced in all cell types and immunogenicity (supernatant-associated proinflammatory cytokines) in primary cells is evaluated. The mRNA construct that demonstrates the optimum combination of high EPO production (in 1 or more cell types) and low cytokine elicitation is used in subsequent studies. Improvements in 5' and 3'UTRs of EPO-ψmRNA and longer poly(A) tails result in an estimated 2-10-fold enhancement in translation efficiency, with no increase in immunogenicity.

Example 19: Characterization of EPO Production and Biological Response to EPO-ψmRNA In Vivo Materials and Experimental Methods Administration of EPO-ψmRNA to Mice.

All animal studies described herein are performed in accordance with the NIH Guide for Care and Use of Laboratory Animals and approved by the Institutional Animal Care and Use Committee of the University of Pennsylvania. Female BALB/c mice (n=5 per experimental condition; 6 weeks, 18-23 g; Charles River Laboratories) are anesthetized using 3.5% halothane in a mixture of $N_2O$ and $O_2$ (70:30), then halothane reduced to 1% and anesthesia maintained using a nose mask. Animal body temperatures are maintained throughout the procedure using a 37° C. warmed heating pad. EPO-ψmRNA-lipofectin complexes (constructed by mixing varying amounts of nucleic acid with 1 μl lipofectin in 60 μl final volume are injected into the lateral tail vein. Blood samples are collected 3 times a day for 3 days post mRNA injection during the time-course study, at 1 optimal time point in dose-response studies, and daily from days 2-6 in studies for reticulocytosis.

Determination of Reticulocytes by Flow Cytometry.

Whole blood samples are stained using Retic-COUNT reagent (BD Diagnostics) and data events acquired on a FACScan flow cytometer. Red blood cells (RBCs) are selected by forward and side scatter properties and analyzed for uptake of Thiazole Orange. Cells stained with Retic-COUNT reagent are detected by fluorescence and reticulocytes expressed as the percentage of total RBC. At least 50,000 events are counted per sample.

Results

To optimize production of biologically functional human EPO protein (hEPO) in response to EPO-encoding mRNA, the following studies are performed:

Time Course of EPO Production after a Single Injection of EPO-ψmRNA.

Following intravenous administration of 1 μg PO-ψmRNA, hEPO is measured serially from 1-96 h after EPO-ψmRNA administration by ELISA, to determined the half-life of EPO protein in the serum will be determined. This half-life is a product of both the half-life of EPO protein and the functional half-life of the EPO-ψmRNA. The resulting optimal time point for measuring EPO protein after EPO-ψmRNA administration is utilized in subsequent studies.

Dose-Response of EPO Production after a Single Injection of EPO-ψmRNA.

To determine the correlation between the amount of EPO protein produced and the amount of EPO-ψmRNA administered, increasing concentrations of EPO-ψmRNA (0.01 to 1 μg/animal) are administered and EPO will be measured at the optimal time point.

Relationship Between hEPO Production and Reticulocytosis.

To measure the effect of EPO-ψmRNA on a biological correlate of EPO activity, flow cytometry is used to determine reticulocyte frequency in blood). Flow cytometry has a coefficient of variation of <3%. Mice receive a single dose of EPO-ψmRNA, and blood is collected from mice daily from days 2-6. The relationship between EPO-ψmRNA dose and reticulocyte frequency is then evaluated at the time point of maximal reticulocytosis. The dose of EPO-ψmRNA that leads to at least a 5% increase in reticulocyte count is used in subsequent studies. Serum hEPO concentrations in mice of an estimated 50 mU/ml and/or an increase in reticulocyte frequency of an estimated 5% are obtained.

Example 20: Measuring Immune Responses to EPO-ψmRNA In Vivo

Materials and Experimental Methods

Detection of Cytokines in Plasma

Serum samples obtained from blood collected at different times during and after 7 daily lipofectin-complexed mRNA administrations are analyzed for mouse IFN-α, TNF-α, and IL-12 using ELISA kits.

Northern Blot Analysis.

Aliquots (2.0 μg) of RNA samples isolated from spleen are separated by denaturing 1.4% agarose gel electrophoresis, transferred to charged membranes (Schleicher and Schuell) and hybridized in MiracleHyb® (Stratagene). Membranes are probed for TNF-α, down-stream IFN signaling molecules (e.g. IRF7, IL-12 p35 and p40, and GAPDH) and other markers of immune activation. Specificity of all probes is confirmed by sequencing. To probe the membranes, 50 ng of DNA is labeled using Redivue[α-$^{32}$P] dCTP® (Amersham) with a random prime labeling kit (Roche). Hybridized membranes are exposed to Kodak BioMax MS film using an MS intensifier screen at −70° C.

Histopathology.

Spleens from EPO-ψmRNA-treated and positive and negative control-treated mice are harvested, fixed, sectioned, stained with hematoxylin and eosin and examined by a veterinary pathologist for signs of immune activation.

Results

To confirm the reduced immunogenicity of RNA molecules of the present invention, mice (n=5) receive daily doses of EPO-ψmRNA for 7 days, then are evaluated for immune-mediated adverse events, as indicated by serum cytokine concentrations, splenic expression of mRNAs encoding inflammatory proteins, and pathologic examination. Maximum administered doses are 3 μg or 5× the effective single dose as determined above. Unmodified mRNA and Lipofectin® alone are used as positive and negative controls, respectively.

These studies confirm the reduced immunogenicity of RNA molecules of the present invention.

Example 21: Further Improvement of EPO-ψmRNA Delivery Methods

Nanoparticle Complexing.

Polymer and ψmRNA solutions are mixed to form complexes. Various formulation conditions are tested and optimized: (1) sub-22 nm polyethylenimine (PEI)/mRNA complexes are made by addition of 25 volumes of mRNA to 1 volume of PEI in water with no mixing for 15 minutes. (2) The rod-like poly-L-lysine-polyethylene glycol (PLL-PEG) with average dimensions of 12×150 nm is synthesized by slow addition of 9 volumes of mRNA to 1 volume of $CK_{30}$-$PEG_{10k}$ in acetate counterion buffer while vortexing. (3) For synthesis of biodegradable gene carrier polymer, polyaspartic anhydride-co-ethylene glycol (PAE) is synthesized by ring opening polycondensation of N-(Benzyloxycarbonyl)-L-aspartic anhydride and ethylene glycol. Then, the pendent amine of aspartic acid is deprotected and protonated by acidification with hydrogen chloride and condensed with mRNA. (4) For latest generation of nanoparticles, aliquot stock $CK_{30}PEG_{10k}$ as ammonium acetate (1.25 mL; 6.4 mg/mL) is added to siliconized Eppendorf tubes. Then mRNA is added slowly to $CK_{30}PEG_{10k}$ (2.5 mg in 11.25 mL RNase-free $H_2O$) over 1-2 mins. After 15 mins, it is diluted 1:2 in RNase-free $H_2O$.

Intratracheal Delivery.

Mice are anesthetized with 3% halothane (70% $N_2O$+30% $O_2$) in an anesthetic chamber and maintained with 1% halothane (70% $N_2O$+30% $O_2$) during operation using a nose cone. Trachea is exposed, and 50 μl of mRNA complex is infused with 150 μl air into the lung through the trachea using 250 μl Hamilton syringe (Hamilton, Reno, Nev.) with a 27 G ½" needle.

Results

To improve efficiency of delivery and expression of ψmRNA administered via the intratracheal (i.t.) route, ψmRNA is encapsulated in nanoparticles. Nanoparticle packaging involves condensing and encapsulating DNA (for example) into particles that are smaller than the pore of the nuclear membrane, using chemicals including poly-L-lysine and polyethylene glycol. RNA is packaged into 4 different nanoparticle formulations (PEI, PLL, PAE, and $CK_{30}PEG_{10k}$), and efficiency of ψmRNA delivery is compared for luciferase-encoding ψmRNA compare the (Luc-ψmRNA). Delivery kinetics and dose-response are then characterized using EPO-ψmRNA.

Example 22: Prevention of Restenosis by Delivery to the Carotid Artery of Recombinant Heat Shock Protein-Encoding, Modified mRNA Materials and Experimental Methods Experimental Design RNA is administered to the carotid artery of rats by intra-arterial injection near the time of balloon angioplasty, after which blood flow is reinstated. Rats are sacrificed 3 h following injection, carotid artery sections are excised, vascular endothelial cells are harvested and homogenized, and luciferase activity is determined as described in above Examples.

Results

Luciferase-encoding pseudouridine-modified RNA is administered to rat carotid arteries. 3 hours later, luciferase RNA can be detected at the delivery site but not the adjacent sites.

Next, this protocol is used to prevent restenosis of a blood vessel following balloon angioplasty in an animal restenosis model, by delivery of modified RNA encoding a heat shock protein, e.g. HSP70; a growth factor (e.g. platelet-derived growth factor (PDGF), vascular endothelial growth factor (V-EGF), or insulin-like growth factor (IGF); or a protein that down-regulates or antagonizes growth factor signaling. Administration of modified RNA reduces incidence of restenosis.

Example 23: Treatment of Cystic Fibrosis by Delivery of CFTR-Encoding Modified mRNA Molecules to Respiratory Epithelium CFTR-encoding pseudouridine- or nucleoside-modified RNA is delivered, as described in Example 13, to the lungs of a cystic fibrosis animal model, and its effect on the disease is assessed as described in Scholte B J, et al (Animal models of cystic fibrosis. J Cyst Fibros 2004; 3 Suppl 2: 183-90) or Copreni E, et al, Lentivirus-mediated gene transfer to the respiratory epithelium: a promising approach to gene therapy of cystic fibrosis. Gene Ther 2004; 11 Suppl 1: S67-75). Administration of the RNA ameliorates cystic fibrosis.

In additional experiments, modified mRNA molecules of the present invention are used to deliver to the lungs other recombinant proteins of therapeutic value, e.g. via an inhaler that delivers RNA.

Example 24: Treatment of XLA by Delivery of ADA-Encoding Modified mRNA Molecules to Hematopoietic Cells ADA-encoding pseudouridine- or nucleoside-modified RNA is delivered to the hematopoietic cells of an X-linked agammaglobulinemia animal model, and its effect on the disease is assessed as described in Tanaka M, Gunawan F, et al, Inhibition of heart transplant injury and graft coronary artery disease after prolonged organ ischemia by selective protein kinase C regulators. J Thorac Cardiovasc Surg 2005; 129(5): 1160-7) or Zonta S, Lovisetto F, et al, Ureteroneocystostomy in a swine model of kidney transplantation: a new technique. J Surg Res. 2005 April; 124(2):250-5). Administration of the RNA is found to improve XLA.

Example 25: Prevention of Organ Rejection by Delivery of Immuno-Modulatory Protein-Encoding Modified mRNA Molecules to a Transplant Site Pseudouridine- or nucleoside-modified RNA encoding a cytokine, a chemokine, or an interferon (e.g. IL-4, IL-13, IL-10, or TGF-β) is delivered to the transplant site of an organ transplant rejection animal model, and its effect on the incidence of rejection is assessed as described in Yu P W, Tabuchi R S et al, Sustained correction of B-cell development and function in a murine model of X-linked agammaglobulinemia (XLA) using retroviral-mediated gene transfer. Blood. 2004 104(5): 1281-90) or Satoh M, Mizutani A et al, X-linked immunodeficient mice spontaneously produce lupus-related anti-RNA helicase A autoantibodies, but are resistant to pristane-induced lupus. Int Immunol 2003, 15(9): 1117-24). Administration of the RNA reduces incidence of transplant rejection.

Example 26: Treatment of Niemann-Pick Disease, Mucopolysaccharidosis, and Other Inborn Metabolic Errors by Delivery of Modified mRNA to Body Tissues Sphingomyelinase-encoding pseudouridine- or nucleoside-modified RNA is delivered to the lung, brain, or other tissue of Niemann-Pick disease Type A and B animal models, and its effect on the disease is assessed as described in Passini M A, Macauley S L, et al, AAV vector-mediated correction of brain pathology in a mouse model of Niemann-Pick A disease. Mol Ther 2005; 11(5): 754-62) or Buccoliero R, Ginzburg L, et al, Elevation of lung surfactant phosphatidylcholine in mouse models of Sandhoff and of Niemann-Pick A disease. J Inherit Metab Dis 2004; 27(5): 641-8). Administration of the RNA is found to improve the disease.

Pseudouridine- or nucleoside-modified RNA encoding alpha-L-iduronidase, iduronate-2-sulfatase, or a related enzyme is delivered to the body tissues of a mucopolysaccharidosis animal model of, and its effect on the disease is assessed as described in Simonaro C M, D'Angelo M, et al, Joint and bone disease in mucopolysaccharidoses VI and VII: identification of new therapeutic targets and biomarkers using animal models. Pediatr Res 2005; 57(5 Pt 1): 701-7) or McGlynn R, Dobrenis K, et al, Differential subcellular localization of cholesterol, gangliosides, and glycosaminoglycans in murine models of mucopolysaccharide storage disorders. J Comp Neurol 2004 20; 480(4): 415-26). Administration of the RNA ameliorates the disease.

In additional experiments, modified mRNA molecules of the present invention are used to provide clotting factors (e.g. for hemophiliacs).

In additional experiments, modified mRNA molecules of the present invention are used to provide acid-b-glucosidase for treating Gaucher's.

In additional experiments, modified mRNA molecules of the present invention are used to provide alpha-galactosidase A for treating Fabry's diseases.

In additional experiments, modified mRNA molecules of the present invention are used to provide cytokines for treatment of infectious diseases.

In additional experiments, modified mRNA molecules of the present invention are used to correct other inborn errors of metabolism, by administration of mRNA molecules encoding, e.g. ABCA4; ABCD3; ACADM; AGL; AGT; ALDH4A1; ALPL; AMPD1; APOA2; AVSD1; BRCD2; C1QA; C1QB; C1QG; C8A; C8B; CACNA1S; CCV; CD3Z; CDC2L1; CHML; CHS1; CIAS1; CLCNKB; CMD1A; CMH2; CMM; COL11A1; COL8A2; COL9A2; CPT2; CRB1; CSE; CSF3R; CTPA; CTSK; DBT; DIO1; DISC1; DPYD; EKV; ENO1; ENO1P; EPB41; EPHX1; F13B; F5; FCGR2A; FCGR2B; FCGR3A; FCHL; FH; FMO3; FMO4; FUCA1; FY; GALE; GBA; GFND; GJA8; GJB3; GLC3B; HF1; HMGCL; HPC1; HRD; HRPT2; HSD3B2; HSPG2; KCNQ4; KCS; KIF1B; LAMB3; LAMC2; LGMD1B; LMNA; LOR; MCKD1; MCL1; MPZ; MTHFR; MTR; MUTYH; MYOC; NB; NCF2; NEM1; NPHS2; NPPA; NRAS; NTRK1; OPTA2; PBX1; PCHC; PGD; PHA2A; PHGDH; PKLR; PKP1; PLA2G2A; PLOD; PPOX; PPT1; PRCC; PRG4; PSEN2; PTOS1; REN; RFX5; RHD; RMD1; RPE65; SCCD; SERPINC1; SJS1; SLC19A2; SLC2A1; SPG23; SPTA1; TAL1; TNFSF6; TNNT2; TPM3; TSHB; UMPK; UOX; UROD; USH2A; VMGLOM; VWS; WS2B; ABCB11; ABCG5; ABCG8; ACADL; ACP1; AGXT; AHHR; ALMS1; ALPP; ALS2; APOB; BDE; BDMR; BJS; BMPR2; CHRNA1; CMCWTD; CNGA3; COL3A1; COL4A3; COL4A4; COL6A3; CPS1; CRYGA; CRYGEP1; CYP1B1; CYP27A1; DBI; DES; DYSF; EDAR; EFEMP1; EIF2AK3; ERCC3; FSHR; GINGF; GLC1B; GPD2; GYPC; HADHA; HADHB; HOXD13; HPE2; IGKC; IHH; IRS1; ITGA6; KHK; KYNU; LCT; LHCGR; LSFC; MSH2; MSH6; NEB; NMTC; NPHP1; PAFAH1P1; PAX3; PAX8; PMS1; PNKD; PPH1; PROC; REG1A; SAG; SFTPB; SLC11A1; SLC3A1; SOS1; SPG4; SRD5A2; TCL4; TGFA; TMD; TPO; UGT1A@; UV24; WSS; XDH; ZAP70; ZFHX1B; ACAA1; AGS1; AGTR1; AHSG; AMT; ARMET; BBS3; BCHE; BCPM; BTD; CASR; CCR2; CCR5; CDL1; CMT2B; COL7A1; CP; CPO; CRV; CTNNB1; DEM; ETM1; FANCD2; FIH; FOXL2; GBE1; GLB1; GLC1C; GNAI2; GNAT1; GP9; GPX1; HGD; HRG; ITIH1; KNG; LPP; LRS1; MCCC1; MDS1; MHS4; MITF; MLH1; MYL3; MYMY; OPA1; P2RY12; PBXP1; PCCB; POU1F1; PPARG; PROS1; PTHR1; RCA1; RHO; SCA7; SCLC1; SCN5A; SI; SLC25A20; SLC2A2; TF; TGFBR2; THPO; THRB; TKT; TM4SF1; TRH; UMPS; UQCRC1; USH3A; VHL; WS2A; XPC; ZNF35; ADH1B; ADH1C; AFP; AGA; AIH2; ALB; ASMD; BFHD; CNGA1; CRBM; DCK; DSPP; DTDP2; ELONG; ENAM; ETFDH: EVC; F11; FABP2; FGA; FGB; FGFR3; FGG; FSHMD1A; GC; GNPTA; GNRHR; GYPA; HCA; HCL2; HD; HTN3; HVBS6; IDUA; IF; JPD; KIT; KLKB1; LQT4; MANBA; MLLT2; MSX1; MTP; NR3C2; PBT; PDE6B; PEE1; PITX2; PKD2; QDPR; SGCB; SLC25A4; SNCA; SOD3; STATH; TAPVR1; TYS; WBS2; WFS1; WHCR; ADAMTS2; ADRB2; AMCN; AP3B1; APC; ARSB; B4GALT7; BHR1; C6; C7; CCAL2; CKN1; CMDJ; CRHBP; CSF1R; DHFR; DIAPH1; DTR; EOS; EPD; ERVR; F12; FBN2; GDNF; GHR; GLRA1; GM2A; HEXB; HSD17B4; ITGA2; KFS; LGMD1A; LOX; LTC4S; MAN2A1; MCC; MCCC2; MSH3; MSX2; NR3C1; PCSK1; PDE6A; PFB1; RASA1; SCZD1; SDHA; SGCD; SLC22A5; SLC26A2; SLC6A3; SM1; SMA@; SMN1; SMN2; SPINK5; TCOF1; TELAB1; TGFBI; ALDH5A1; ARG1; AS; ASSP2; BCKDHB; BF; C2; C4A; CDKN1A COL10A1; COL11A2; CYP21A2; DYX2; EJM1; ELOVL4; EPM2A; ESR1; EYA4; F13A1; FANCE; GCLC; GJA1; GLYS1; GMPR; GSE; HCR; HFE; HLA-A; HLA-DPB1; HLA-DRA; HPFH; ICS1; IDDM1; IFNGR1; IGAD1; IGF2R; ISCW; LAMA2; LAP; LCA5; LPA; MCDR1; MOCS1; MUT; MYB; NEU1; NKS1; NYS2; OA3; ODDD; OFC1; PARK2; PBCA; PBCRA1; PDB1; PEX3; PEX6; PEX7; PKHD1; PLA2G7; PLG; POLH; PPAC; PSORS1; PUJO; RCD1; RDS; RHAG; RP14; RUNX2; RWS; SCA1; SCZD3; SIASD; SOD2; ST8: TAP1; TAP2; TFAP2B; TNDM; TNF; TPBG; TPMT; TULP1; WISP3; AASS; ABCB1; ABCB4; ACHE; AQP1; ASL; ASNS; AUTS1; BPGM; BRAF; C7orf2; CACNA2D1; CCM1; CD36; CFTR; CHORDOMA; CLCN1; CMH6; CMT2D; COL1A2; CRS; CYMD; DFNA5; DLD; DYT11; EEC1; ELN; ETV1; FKBP6; GCK; GHRHR; GHS; GLI3; GPDS1; GUSB; HLXB9; HOXA13; HPFH2; HRX; IAB; IMMP2L; KCNH2; LAMB1; LEP; MET; NCF1; NM; OGDH; OPN1SW; PEX1; PGAM2; PMS2; PON1; PPP1R3A; PRSS1; PTC; PTPN12; RP10; RP9; SERPINE1; SGCE; SHFM1; SHH; SLC26A3; SLC26A4; SLOS; SMAD1; TBXAS1; TWIST; ZWS1; ACHM3; ADRB3; ANK1; CA1; CA2; CCAL1; CLN8; CMT4A; CNGB3; COH1; CPP; CRH; CYP11B1; CYP11B2; DECR1; DPYS; DURS1; EBS1; ECA1; EGI; EXT1; EYA1; FGFR1; GNRH1; GSR; GULOP; HR; KCNQ3; KFM; KWE; LGCR; LPL; MCPH1; MOS; MYC; NAT1; NAT2; NBS1; PLAT; PLEC1; PRKDC; PXMP3; RP1; SCZD6; SFTPC; SGM1; SPG5A; STAR; TG; TRPS1; TTPA; VMD1; WRN; ABCA1; ABL1; ABO; ADAMTS13; AK1; ALAD; ALDH1A1; ALDOB; AMBP; AMCD1; ASS; BDMF; BSCL; C5; CDKN2A; CHAC; CLA1; CMD1B; COL5A1; CRAT; DBH; DNAI1; DYS; DYT1; ENG; FANCC; FBP1; FCMD; FRDA; GALT; GLDC; GNE; GSM1; GSN; HSD17B3; HSN1; IBM2; INVS; JBTS1; LALL; LCCS1; LCCS; LGMD2H; LMX1B; MLLT3; MROS; MSSE; NOTCH1; ORM1; PAPPA; PIP5K1B; PTCH; PTGS1; RLN1; RLN2; RMRP: ROR2; RPD1; SARDH; SPTLC1; STOM; TDFA; TEK; TMC1; TRIM32; TSC1; TYRP1; XPA; CACNB2; COL17A1; CUBN; CXCL12; CYP7; CYP2C19; CYP2C9; EGR2; EMX2; ERCC6; FGFR2; HK1; HPS1; IL2RA; LGI1; LIPA; MAT1A; MBL2; MKI67; MXI1; NODAL; OAT; OATL3; PAX2; PCBD; PEO1; PHYH; PNLIP; PSAP; PTEN; RBP4; RDPA; RET; SFTPA1; SFTPD; SHFM3; SIAL; THC2; TLX1; TNFRSF6; UFS; UROS; AA; ABCC8; ACAT1; ALX4; AMPD3; ANC; APOA1; APOA4; APOC3; ATM; BSCL2; BWS; CALCA; CAT; CCND1; CD3E; CD3G; CD59; CDKN1C; CLN2; CNTF; CPT1A; CTSC; DDB1; DDB2; DHCR7; DLAT; DRD4; ECB2; ED4; EVR1; EXT2; F2; FSHB; FTH1; G6PT1; G6PT2; GIF; HBB; HBBP1; HBD; HBE1; HBG1; HBG2; HMBS; HND; HOMG2; HRAS; HVBS1; IDDM2; IGER; INS; JBS; KCNJ11; KCNJ1; KCNQ1; LDHA; LRP5; MEN1; MLL; MYBPC3; MYO7A; NNO1; OPPG; OPTB1; PAX6; PC; PDX1; PGL2; PGR; PORC; PTH; PTS; PVRL1; PYGM; RAG1; RAG2; ROM1; RRAS2; SAA1; SCA5; SCZD2; SDHD; SERPING1; SMPD1; TCIRG1; TCL2; TECTA; TH; TREH; TSG101; TYR; USH1C; VMD2; VRN1; WT1; WT2; ZNF145; A2M; AAAS; ACADS; ACLS; ACVRL1; ALDH2; AMHR2; AOM; AQP2; ATD; ATP2A2; BDC; C1R; CD4; CDK4; CNA1; COL2A1; CYP27B1; DRPLA; ENUR2; FEOM1; FGF23; FPF; GNB3; GNS; HAL; HBP1; HMGA2; HMN2; HPD; IGF1; KCNA1; KERA; KRAS2; KRT1; KRT2A; KRT3; KRT4; KRT5. KRT6A; KRT6B; KRTHB6; LDHB; LYZ; MGCT; MPE; MVK; MYL2; OAP; PAH; PPKB; PRB3; PTPN11; PXR1; RLS; RSN; SAS; SAX1; SCA2;

SCNN1A; SMAL; SPPM; SPSMA; TBX3; TBX5; TCF1; TPI1; TSC3; ULR; VDR; VWF; ATP7B; BRCA2; BRCD1; CLN5; CPB2; ED2; EDNRB; ENUR1; ERCC5; F10; F7; GJB2; GJB6; IPF1; MBS1; MCOR; NYS4; PCCA; RB1; RHOK; SCZD7; SGCG; SLC10A2; SLC25A15; STARP1; ZNF198; ACHM1; ARVD1; BCH; CTAA1; DAD1; DFNB5; EML1; GALC; GCH1; IBGC1; IGH@; IGHC group; IGHG1; IGHM; IGHR; IV; LTBP2; MCOP; MJD; MNG1; MPD1; MPS3C; MYH6; MYH7; NP; NPC2; PABPN1; PSEN1; PYGL; RPGRIP1; SERPINA1; SER-PINA3; SERPINA6; SLC7A7; SPG3A; SPTB; TCL1A; TGM1; TITF1; TMIP; TRA@; TSHR; USH1A; VP; ACCPN; AHO2; ANCR; B2M; BBS4; BLM; CAPN3; CDAN1; CDAN3; CLN6; CMH3; CYP19; CYP1A1; CYP1A2; DYX1; EPB42; ETFA; EYCL3; FAH; FBN1; FES; HCVS; HEXA; IVD; LCS1; LIPC; MYOSA; OCA2; OTSC1; PWCR; RLBP1; SLC12A1; SPG6; TPM1; UBE3A; WMS; ABCC6; ALDOA; APRT; ATP2A1; BBS2; CARD15; CATM; CDH1; CETP; CHST6; CLN3; CREBBP; CTH; CTM; CYBA; CYLD; DHS; DNASE1; DPEP1; ERCC4; FANCA; GALNS; GAN; HAGH; HBA1; HBA2; HBHR; HBQ1; HBZ; HBZP; HP; HSD11B2; IL4R; LIPB; MC1R; MEFV; MHC2TA; MLYCD; MMVP1; PHKB; PHKG2; PKD1; PKDTS; PMM2; PXE; SALL1; SCA4; SCNN1B; SCNN1G; SLC12A3; TAT; TSC2; VD1; WT3; ABR; ACACA; ACADVL; ACE; ALDH3A2; APOH; ASPA; AXIN2; BCL5; BHD; BLMH; BRCA1; CACD; CCA1; CCZS; CHRNB1; CHRNE; CMT1A; COL1A1; CORD5; CTNS; EPX; ERBB2; G6PC; GAA; GALK1; GCGR; GFAP; GH1; GH2; GP1BA; GPSC; GUCY2D; ITGA2B; ITGB3; ITGB4; KRT10; KRT12; KRT13; KRT14; KRT14L1; KRT14L2; KRT14L3; KRT16; KRT16L; KRT16L2; KRT17; KRT9; MAPT; MDB; MDCR; MG1; MHS2; MKS1; MPO; MYO15A; NAGLU; NAPB; NF1; NME1; P4HB; PAFAH1B1; PECAM1; PEX12; PHB; PMP22; PRKAR1A; PRKCA; PRKWNK4; PRP8; PRPF8; PTLAH; RARA; RCV1; RMSA1; RP17; RSS; SCN4A; SERPINF2; SGCA; SGSH; SHBG; SLC2A4; SLC4A1; SLC6A4; SMCR; SOST; SOX9; SSTR2; SYM1; SYNS1; TCF2; THRA; TIMP2; TOC; TOP2A; TP53; TRIM37; VBCH; ATP8B1; BCL2; CNSN; CORD1; CYB5; DCC; F5F8D; FECH; FEO; LAMA3; LCFS2; MADH4; MAFD1; MC2R; MCL; MYP2; NPC1; SPPK; TGFBRE; TGIF; TTR; AD2; AMH; APOC2; APOE; ATHS; BAX; BCKDHA; BCL3; BFIC; C3; CACNA1A; CCO; CEACAM5; COMP; CRX; DBA; DDU; DFNA4; DLL3; DM1; DMWD; EllS; ELA2; EPOR; ERCC2; ETFB; EXT3; EYCL1; FTL; FUT1; FUT2; FUT6; GAMT; GCDH; GP1; GUSM; HB1; HCL1; HHC2; HHC3; ICAM3; INSR; JAK3; KLK3; LDLR; LHB; LIG1; LOH19CR1; LYL1; MAN2B1; MCOLN1; MDRV; MLLT1; NOTCH3; NPHS1; OFC3; OPA3; PEPD; PRPF31; PRTN3; PRX; PSG1; PVR; RYR1; SLC5A5; SLC7A9; STK11; TBXA2R; TGFB1; TNNI3; TYROBP; ADA; AHCY; AVP; CDAN2; CDPD1; CHED1; CHED2; CHRNA4; CST3; EDN3; EEGV1; FTLL1; GDF5; GNAS; GSS; HNF4A; JAG1; KCNQ2; MKKS; NBIA1; PCK1; PI3; PPCD; PPGB; PRNP; THBD; TOP1; AIRE; APP; CBS; COL6A1; COL6A2; CSTB; DCR; DSCR1; FPDMM; HLCS; HPE1; ITGB2; KCNE1; KNO; PRSS7; RUNX1; SOD1; TAM; ADSL; ARSA; BCR; CECR; CHEK2; COMT; CRYBB2; CSF2RB; CTHM; CYP2D6; CYP2D7P1; DGCR; DIA1; EWSR1; GGT1; MGCR; MN1; NAGA; NF2; OGS2; PDGFB; PPARA; PRODH; SCO2; SCZD4; SERPIND1; SLC5A1; SOX10; TCN2; TIMP3; TST; VCF; ABCD1; ACTL1; ADFN; AGMX2; AHDS; AIC; AIED; AIH3; ALAS2; AMCD; AMELX; ANOP1; AR; ARAF1; ARSC2; ARSE; ARTS; ARX; ASAT; ASSP5; ATP7A; ATRX; AVPR2; BFLS; BGN: BTK; BZX; C1HR; CACNA1F; CALB3; CBBM; CCT; CDR1; CFNS; CGF1; CHM; CHR39C; CIDX; CLA2; CLCN5; CLS; CMTX2; CMTX3; CND; COD1; COD2; COL4A5; COL4A6; CPX; CVD1; CYBB; DCX; DFN2; DFN4; DFN6; DHOF; DIAPH2; DKC1; DMD; DSS; DYT3; EBM; EBP; ED1; ELK1; EMD; EVR2; F8; F9; FCP1; FDPSL5; FGD1; FGS1; FMR1; FMR2; G6PD; GABRA3; GATA1; GDI1; GDXY; GJB1; GK; GLA; GPC3; GRPR; GTD; GUST; HMS1; HPRT1; HPT; HTC2; HTR2C; HYR; IDS; IHG1; IL2RG; INDX; IP1; IP2; JMS; KAL1; KFSD; L1CAM; LAMP2; MAA; MAFD2; MAOA; MAOB; MCF2; MCS; MEAX; MECP2; MF4; MGC1; MIC5; MID1; MLLT7; MLS; MRSD; MRX14; MRX1; MRX20; MRX2; MRX3; MRX40; MRXA; MSD; MTM1; MYCL2; MYP1; NDP; NHS; NPHL1; NR0B1; NSX; NYS1; NYX; OA1; OASD; OCRL; ODT1; OFD1; OPA2; OPD1; OPEM; OPN1LW; OPN1MW; OTC; P3; PDHA1; PDR; PFC; PFKFB1; PGK1; PGK1P1; PGS; PHEX; PHKA1; PHKA2; PHP; PIGA; PLP1; POF1; POLA; POU3F4; PPMX; PRD; PRPS1; PRPS2; PRS; RCCP2; RENBP; RENS1; RP2; RP6; RPGR; RPS4X; RPS6KA3; RS1; S11; SDYS; SEDL; SERPINA7; SH2D1A; SHFM2; SLC25A5; SMAX2; SRPX; SRS; STS; SYN1; SYP; TAF1; TAZ; TBX22; TDD; TFE3; THAS; THC; TIMM8A; TIMP1; TKCR; TNFSF5; UBE1; UBE2A; WAS; WSN; WTS; WWS; XIC; XIST; XK; XM; XS; ZFX; ZIC3; ZNF261; ZNF41; ZNF6; AMELY; ASSP6; AZF1; AZF2; DAZ; GCY; RPS4Y; SMCY; SRY; ZFY; ABAT; AEZ; AFA; AFD1; ASAH1; ASD1; ASMT; CCAT; CECR9; CEPA; CLA3; CLN4; CSF2RA; CTS1; DF; DIH1; DWS; DYT2; DYT4; EBR3; ECT; EEF1A1L14; EYCL2; FANCB; GCSH; GCSL; GIP; GTS; HHG; HM1; HOAC; HOKPP2; HRPT1; HSD3B3; HTC1; HV1S; ICHQ; ICR1; ICR5; IL3RA; KAL2; KMS; KRT18; KSS; LCAT; LHON; LIMM; MANBB; MCPH2; MEB; MELAS; MIC2: MPFD; MS; MSS: MTATP6; MTCO1; MTCO3: MTCYB; MTND1; MTND2; MTND4; MTND5; MTND6; MTRNR1; MTRNR2; MTTE; MTTG; MTT1; MTTK; MTTL1; MTTL2; MTTN; MTTP; MTTS1; NAMSD; OCD1; OPD2; PCK2; PCLD; PCOS1; PFKM; PKD3; PRCA1; PRO1; PROP1; RBS; RFXAP; RP; SHOX; SLC25A6; SPG5B; STO: SUOX; THM; or TTD.

Example 27: Treatment of Vasospasm by Delivery of iNOS-Encoding Modified mRNA Molecules to Body Tissues Inducible nitric oxide synthase (iNOS)-encoding pseudouridine- or nucleoside-modified RNA is delivered to the vascular endothelium of vasospasm animals models (e.g. subarachnoid hemorrhage), and its effect on the disease is assessed as described in Pradilla G, Wang P P, et al, Prevention of vasospasm by anti-CD11/CD18 monoclonal antibody therapy following subarachnoid hemorrhage in rabbits. J Neurosurg 2004; 101(1): 88-92) or Park S, Yamaguchi M, et al, Neurovascular protection reduces early brain injury after subarachnoid hemorrhage. Stroke 2004; 35(10): 2412-7). Administration of the RNA ameliorates the disease.

Example 28: Restoration of Hair Growth by Delivery of Modified mRNA Encoding an Immunosuppressive Protein Pseudouridine- or nucleoside-modified RNA encoding a telomerase or an immunosuppressive protein (e.g. α-MSH, TGF-β1, or IGF-I is delivered to hair follicles of animals used as models of hair loss or balding, and its effect on hair growth is assessed as described in Jiang J, Tsuboi R. et al, Topical application of ketoconazole stimulates hair growth in C3H/HeN mice. J Dermatol 2005; 32(4): 243-7) or McElwee K J, Freyschmidt-Paul P, et al, Transfer of CD8(+) cells induces localized hair loss whereas CD4(+)/CD25(−) cells promote systemic alopecia areata and CD4(+)/CD25 (+) cells blockade disease onset in the C3H/HeJ mouse model. J Invest Dermatol 2005; 124(5): 947-57). Administration of the RNA restores hair growth.

Example 29: Synthesis of an In Vitro-Transcribed RNA Molecule with Altered Nucleosides Containing an siRNA A double-stranded RNA (dsRNA) molecule comprising pseudouridine or a modified nucleoside and further comprising a small interfering RNA (siRNA) or short hairpin RNA (shRNA) is synthesized by the following procedure: Complementary RNA strands with the desired sequence containing uridine or 1 or more modified nucleosides are synthesized by in vitro transcription (e.g. by T7, SP6, or T3 phage RNA polymerase) as described in Example 2. dsRNA molecules exhibit reduced immunogenicity. In other experiments, the dsRNA molecules are designed to be processed by a cellular enzyme to yield the desired siRNA or shRNA. Because dsRNA molecules of several hundred nucleotides are easily synthesized, each dsRNA may also be designed to contain several siRNA or shRNA molecules, to facilitate delivery of multiple siRNA or shRNA to a single target cell.

Example 30: Use of an In Vitro-Transcribed RNA Molecule with Altered Nucleosides to Deliver siRNA The dsRNA molecule of the previous Example is complexed with a transfection reagent (e.g a cationic transfection reagent, a lipid-based transfection reagent, a protein-based transfection reagent, a polyethyleneimine based transfection reagent, or calcium phosphate) and delivered to a target cell of interest. Enzymes in or on the surface of the target cell degrade the dsRNA to the desired siRNA or shRNA molecule(s). This method effectively silences transcription of 1 or more cellular genes corresponding to the siRNA or shRNA sequence(s).

Example 31: Testing the Effect of Additional Nucleoside Modifications on RNA Immunogenicity and Efficiency of Translation Additional nucleoside modifications are introduced into in vitro-transcribed RNA, using the methods described above in Examples 2 and 7, and their effects on immunogenicity translation efficiency are tested as described in Examples 1-8 and 9-15, respectively. Certain additional modifications are found to decrease immunogenicity and enhance translation. These modifications are additional embodiments of methods and compositions of the present invention.

Modifications tested include, e.g.:

$m^1A$; $m^2A$; Am; $ms^2m^6A$; $i^6A$; $ms^2i6A$; $io^6A$; $ms^2io^6A$; $g^6A$; $t^6A$; $ms^2t^6A$; $m^6t^6A$; $hn^6A$; $ms^2hn^6A$; Ar(p); I; $m^1I$; $m^1Im$; $m^3C$; Cm; $s^2C$; $ac^4C$; $f^5C$; $m^5Cm$; $ac^4Cm$; $k^2C$; $m^1G$; $m^2G$; $m^7G$; Gm; $m^2_2G$; $m^2Gm$; $m^2_2Gm$; Gr(p); yW; $o_2yW$; OHyW; OHyW*; imG; mimG; Q; oQ; galQ; manQ; $preQ_0$; $preQ_1$; $G^+$; D; $m^5Um$; mΨ; Ψm; $s^4U$; $m^5s^2U$; $s^2Um$; $acp^3U$; $ho^5U$; $mo^5U$; $cmo^5U$; $mcmo^5U$; $chm^5U$; $mchm^5U$; $mcm^5U$; $mcm^5Um$; $mcm^5s^2U$; $nm^5s^2U$; $mnm^5U$; $mnm^5s^2U$; $mnm^5se^2U$; $ncm^5U$; $ncm^5Um$; $cnnm^5U$; $cnnm^5Um$; $cnnm^5s^2U$; $m^6_2A$; Im; $m^4C$; $m^4Cm$; $hm^5C$; $m^3U$; $m^1acp^3Ψ$; $cm^5U$; $m^6Am$; $m^6_2Am$; $m^{2,7}G$; $m^{2,2,7}G$; $m^3Um$; $m^5D$; $m^3Ψ$; $f^5Cm$; $m^1Gm$; $m^1Am$; $τm^5U$; $τm^5s2U$; imG-14; imG2; and $ac^6A$.

---

What is claimed is:

1. A method for reducing the immunogenicity of in vitro-synthesized RNA comprising an open reading frame that encodes a functional protein, the method comprising:
   replacing a nucleotide of the in vitro-synthesized RNA with at least one modified nucleotide comprising a modified nucleoside selected from the group consisting of: pseudouridine ($\Psi$), 1-methylpseudouridine ($m^1\Psi$), 5-methyluridine ($m^5U$), 2-thiouridine ($s^2U$), 2'-O-methyl-U (Um) and 5-methylcytidine ($m^5C$),
   wherein when pseudouridine ($\Psi$) is selected, it replaces uridine, and
   wherein when 1-methylpseudouridine ($m^1\Psi$) is selected, it replaces uridine, and
   wherein when 5-methyluridine ($m^5U$) is selected, it replaces uridine, and
   wherein when 2-thiouridine ($s^2U$) is selected, it replaces uridine, and
   wherein when 2'-O-methyl-U (Um) is selected, it replaces uridine, and
   wherein when 5-methylcytidine ($m^5C$) is selected, it replaces cytidine, and
   thereby generating in vitro-synthesized RNA comprising a modified nucleotide and reducing the immunogenicity of said in vitro-synthesized RNA compared with an in vitro-synthesized RNA that does not comprise said modified nucleotide.

2. The method of claim 1, wherein the reduced immunogenicity is detected by at least one method selected from the group consisting of:

(i) detecting a decrease in immunogenicity such that the in vitro-synthesized RNA comprising a modified nucleotide can be repeatedly administered without eliciting an immune response sufficient to detectably reduce expression of said functional protein, whereas repeatedly administering the same quantity of in vitro-synthesized RNA that does not comprise said modified nucleotide does detectably reduce expression of said functional protein;

(ii) measuring less secretion of at least one cytokine in response to administration of in vitro-synthesized RNA comprising a modified nucleotide compared to the amount of said cytokine secreted in response to administration of the same quantity of in vitro-synthesized RNA comprising the unmodified uridine or cytidine nucleotide; or (iii) detecting a lower level of activation of toll-like receptor (TLR) signaling molecules in response to in vitro-synthesized RNA comprising a modified nucleotide compared to the level of activation of TLR signaling molecules in response to the same quantity of in vitro-synthesized RNA that does not comprise said modified nucleotide.

3. The method of claim 2, wherein said at least one cytokine in (ii) is selected from the group consisting of: IL-12, IFN-$\alpha$, TNF-$\alpha$, RANTES, MIP-1$\alpha$, MIP-1$\beta$, IL-6, IFN-$\beta$ and IL-8; or said TLR signaling molecule in (iii) is selected from the group consisting of TLR3, TLR7 and TLR8 signaling molecules.

4. The method of claim 1, wherein said replacing comprises replacing 100% of said uridine nucleotides with a modified nucleotide comprising a nucleoside selected from the group consisting of Ψ, m¹Ψ, m⁵U, s²U and Um and replacing 100% of said cytidine nucleotides with a modified nucleotide comprising m⁵C.

5. The method of claim 1, wherein said replacing comprises replacing 0.2% to 100% of said uridine nucleotides with a modified nucleotide comprising a modified nucleoside selected from the group consisting of Ψ, m¹Ψ, m⁵U, s²U and Um.

6. The method of claim 5, wherein said replacing further comprises replacing 0.2% to 100% of said cytidine nucleotides with a modified nucleotide comprising m⁵C.

7. The method of claim 1, wherein said replacing comprises replacing 0.2% to 100% of said cytidine nucleotides with a modified nucleotide comprising m⁵C.

8. The method of claim 1, wherein said replacing further comprises replacing 0.2% to 100% of the adenosine nucleotides with a modified nucleotide comprising N6-methyladenosine (m⁶A).

9. The method of claim 1, wherein said replacing comprises synthesizing said in vitro-synthesized RNA comprising a modified nucleotide in an in vitro transcription reaction comprising a DNA template comprising an open reading frame encoding said functional protein, an RNA polymerase, and a mixture of nucleoside triphosphates (NTPs) in which a desired percentage of a triphosphate derivative of each desired modified nucleoside is substituted for the unmodified NTP.

10. The method of claim 1, wherein said in vitro-synthesized RNA comprises at least one selected from the group consisting of:
   A. a poly-A tail;
   B. an m⁷GpppG cap; and
   C. a cap-independent translational enhancer.

11. The method of claim 1, wherein said protein encoded by said in vitro-synthesized RNA is selected from the group consisting of: erythropoietin (EPO); a detectable enzyme selected from firefly luciferase, *Renilla* luciferase, bacterial beta-galactosidase (lacZ), and green fluorescent protein (GFP); a transcription factor selected from MYC and SRY or MCOP; a growth factor or cytokine selected from the group consisting of platelet-derived growth factor (PDGF), vascular endothelial growth factor (VEGF), transforming growth factor-beta1 (TGF-beta1), insulin-like growth factor (IGF), alpha-melanocyte-stimulating hormone (alpha-MSH); insulin-like growth factor-I (IGF-I); IL-4; IL-13; and IL-10; inducible nitric oxide synthase (iNOS); a heat shock protein; Cystic Fibrosis Transmembrane Conductance Regulator (CFTR); an enzyme with antioxidant activity selected from among catalase, phospholipid hydroperoxide glutathione peroxidase, superoxide dismutase-1, and superoxide dismutase-2; Bruton's tyrosine kinase; adenosine deaminase; ecto-nucleoside triphosphate diphosphydrolase; ABCA4; ABCD3; ACADM; AGL; AGT; ALDH4A1; ALPL; AMPD1; APOA2; AVSD1; BRCD2; C1QA; C1QB; C1QG; C8A; C8B; CACNA1S; CCV; CD3Z; CDC2L1; CHML; CHS1; CIAS1; CLCNKB; CMD1A; CMH2; CMM; COL11A1; COL8A2; COL9A2; CPT2; CRB1; CSE; CSF3R; CTPA; CTSK; DBT; DIO1; DISC1; DPYD; EKV; ENO1; ENO1P; EPB41; EPHX1; F13B; F5; FCGR2A; FCGR2B; FCGR3A; FCHL; FH; FMO3; FMO4; FUCA1; FY; GALE; GBA; GFND; GJA8; GJB3; GLC3B; HF1; HMGCL; HPC1; HRD; HRPT2; HSD3B2; HSPG2; KCNQ4; KCS; KIF1B; LAMB3; LAMC2; LGMD1B; LMNA; LOR; MCKD1; MCL1; MPZ; MTHFR; MTR; MUTYH; MYOC; NB; NCF2; NEM1; NPHS2; NPPA; NRAS; NTRK1; OPTA2; PBX1; PCHC; PGD; PHA2A; PHGDH; PKLR; PKP1; PLA2G2A; PLOD; PPOX; PPTO; PRCC; PRG4; PSEN2; PTOS1; REN; RFX5; RHD; RMD1; RPE65; SCCD; SERPINC1; SJS1; SLC19A2; SLC2A1; SPG23; SPTA1; TAL1; TNFSF6; TNNT2; TPM3; TSHB; UMPK; UOX; UROD; USH2A; VMGLOM; VWS; WS2B; ABCB11; ABCG5; ABCG8; ACADL; ACP1; AGXT; AHHR; ALMS1; ALPP; ALS2; APOB; BDE; BDMR; BJS; BMPR2; CHRNA1; CMCWTD; CNGA3; COL3A1; COL4A3; COL4A4; COL6A3; CPS1; CRYGA; CRYGEP1; CYP1B1; CYP27A1; DBI; DES; DYSF; EDAR; EFEMP1; EIF2AK3; ERCC3; FSHR; GINGF; GLC1B; GPD2; GYPC; HADHA; HADHB; HOXD13; HPE2; IGKC; IHH; IRS1; ITGA6; KHK; KYNU; LCT; LHCGR; LSFC; MSH2; MSH6; NEB; NMTC; NPHP1; PAFAH1P1; PAX3; PAX8; PMS1; PNKD; PPH1; PROC; REG1A; SAG; SFTPB; SLC11A1; SLC3A1; SOS1; SPG4; SRD5A2; TCL4; TGFA; TMD; TPO; UGT1A@; UV24; WSS; XDH; ZAP70; ZFHX1B; ACAA1; AGS1; AGTR1; AHSG; AMT; ARMET; BBS3; BCHE; BCPM; BTD; CASR; CCR2; CCR5; CDL1; CMT2B; COL7A1; CP; CPO; CRV; CTNNB1; DEM; ETM1; FANCD2; FIH; FOXL2; GBE1; GLB1; GLCLC; GNAI2; GNAT1; GP9; GPX1; HGD; HRG; ITIH1; KNG; LPP; LRS1; MCCC1; MDS1; MHS4; MITF; MLH1; MYL3; MYMY; OPA1; P2RY12; PBXP1; PCCB; POU1F1; PPARG; PROS1; PTHR1; RCA1; RHO; SCA7; SCLC1; SCN5A; SI; SLC25A20; SLC2A2; TF; TGFBR2; THPO; THRB; TKT; TM4SF1; TRH; UMPS; UQCRC1; USH3A; VHL; WS2A; XPC; ZNF35; ADH1B; ADH1C; AFP; AGA; AIH2; ALB; ASMD; BFHD; CNGA1; CRBM; DCK; DSPP; DTDP2; ELONG; ENAM; ETFDH; EVC; F11; FABP2; FGA; FGB; FGFR3; FGG; FSHMD1A; GC; GNPTA; GNRHR; GYPA; HCA; HCL2; HD; HTN3; HVBS6; IDUA; IF; JPD; KIT; KLKB1; LQT4; MANBA; MLLT2; MSX1; MTP; NR3C2; PBT; PDE6B; PEE1; PITX2; PKD2; QDPR; SGCB; SLC25A4; SNCA; SOD3; STATH; TAPVR1; TYS; WBS2; WFS1; WHCR; ADAMTS2; ADRB2; AMCN; AP3B1; APC; ARSB; B4GALT7; BHR1; C6; C7; CCAL2; CKN1; CMDJ; CRHBP; CSF1R; DHFR; DIAPH1; DTR; EOS; EPD; ERVR; F12; FBN2; GDNF; GHR; GLRA1; GM2A; HEXB; HSD17B4; ITGA2; KFS; LGMDLA; LOX; LTC4S; MAN2A; MCC; MCCC2; MSH3; MSX2; NR3C1; PCSK1; PDE6A; PFBI; RASA1; SCZD1; SDHA; SGCD; SLC22A5; SLC26A2; SLC6A3; SM1; SMA@; SMN1; SMN2; SPINK5; TCOF1; TELAB1; TGFBI; ALDH5A1; ARG1; AS; ASSP2; BCKDHB; BF; C2; C4A; CDKN1A; COL10A1; COL11A2; CYP21A2; DYX2; EJM1; ELOVL4; EPM2A; ESR1; EYA4; F13A1; FANCE; GCLC; GJA1; GLYS1; GMPR; GSE; HCR; HFE; HLA-A; HLA-DPB1; HLA-DRA; HPFH; ICS1; IDDM1; IFNGR1; IGAD1; IGF2R; ISCW; LAMA2; LAP; LCA5; LPA; MCDR1; MOCS1; MUT; MYB; NEU1; NKS1; NYS2; OA3; ODDD; OFC0; PARK2; PBCA; PBCRA1; PDB1; PEX3; PEX6; PEX7; PKHD1; PLA2G7; PLG; POLH; PPAC; PSORS1; PUJO; RCD1; RDS; RHAG; RP14; RUNX2; RWS; SCA1; SCZD3; SIASD; SOD2; ST8; TAP1; TAP2; TFAP2B; TNDM; TNF; TPBG; TPMT; TULP1; WISP3; AASS; ABCB1; ABCB4; ACHE; AQP1; ASL; ASNS; AUTS1; BPGM; BRAF; C7orf2; CACNA2D1; CCM1; CD36; CFTR; CHORDOMA; CLCN1; CMH6; CMT2D; COL1A2; CRS; CYMD; DFNA5; DLD; DYT11; EEC1; ELN; ETV1; FKBP6; GCK; GHRHR; GHS; GLI3; GPDS1; GUSB; HLXB9; HOXA13; HPFH2; HRX; LAB; IMMP2L; KCNH2; LAMB1; LEP; MET; NCF1; NM; OGDH; OPN1SW; PEX1; PGAM2; PMS2; PON1;

PPP1R3A; PRSS1; PTC; PTPN12; RP10; RP9; SERPINE1; SGCE; SHFM1; SHH; SLC26A3; SLC26A4; SLOS; SMAD1; TBXAS1; TWIST; ZWS1; ACHM3; ADRB3; ANK1; CA1; CA2; CCAL1; CLN8; CMT4A; CNGB3; COH1; CPP; CRH; CYP11B1; CYP11B2; DECR1; DPYS; DURS1; EBS1; ECA1; EGI; EXT1; EYA1; FGFR1; GNRH1; GSR; GULOP; HR; KCNQ3; KFM; KWE; LGCR; LPL; MCPH1; MOS; MYC; NAT1; NAT2; NBS1; PLAT; PLEC1; PRKDC; PXMP3; RP1; SCZD6; SFTPC; SGM1; SPG5A; STAR; TG; TRPS1; TTPA; VMD1; WRN; ABCA1; ABL1; ABO; ADAMTS13; AK1; ALAD; ALDH1A1; ALDOB; AMBP; AMCD1; ASS; BDMF; BSCL; C5; CDKN2A; CHAC; CLA1; CMD1B; COL5A1; CRAT; DBH; DNAI1; DYS; DYT1; ENG; FANCC; FBP1; FCMD; FRDA; GALT; GLDC; GNE; GSM1; GSN; HSD17B3; HSN1; IBM2; INVS; JBTS1; LALL; LCCS1; LCCS; LGMD2H; LMX1B; MLLT3; MROS; MSSE; NOTCH1; ORM1; PAPPA; PIP5K1B; PTCH; PTGS1; RLN1; RLN2; RMRP; ROR2; RPD1; SARDH; SPTLC1; STOM; TDFA; TEK; TMC1; TRIM32; TSC1; TYRP1; XPA; CACNB2; COL17A1; CUBN; CXCL12; CYP17; CYP2C19; CYP2C9; EGR2; EMX2; ERCC6; FGFR2; HK1; HPS1; IL2RA; LGI1; LIPA; MAT1A; MBL2; MKI67; MXI1; NODAL; OAT; OATL3; PAX2; PCBD; PEO1; PHYH; PNLIP; PSAP; PTEN; RBP4; RDPA; RET; SFTPA1; SFTPD; SHFM3; SIAL; THC2; TLX1; TNFRSF6; UFS; UROS; AA; ABCC8; ACAT1; ALX4; AMPD3; ANC; APOAL; APOA4; APOC3; ATM; BSCL2; BWS; CALCA; CAT; CCND1; CD3E; CD3G; CD59; CDKNLC; CLN2; CNTF; CPT1A; CTSC; DDB1; DDB2; DHCR7; DLAT; DRD4; ECB2; ED4; EVR1; EXT2; F2; FSHB; FTH1; G6PT1; G6PT2; GIF; HBB; HBBP1; HBD; HBE1; HBG1; HBG2; HMBS; HND; HOMG2; HRAS; HVBS1; IDDM2; IGER; INS; JBS; KCNJ11; KCNJ1; KCNQ1; LDHA; LRP5; MEN1; MLL; MYBPC3; MYO7A; NNO1; OPPG; OPTB1; PAX6; PC; PDX1; PGL2; PGR; PORC; PTH; PTS; PVRL1; PYGM; RAG1; RAG2; ROM1; RRAS2; SAA1; SCA5; SCZD2; SDHD; SERPING1; SMPD1; TCIRG1; TCL2; TECTA; TH; TREH; TSG101; TYR; USH1C; VMD2; VRNI; WT1; WT2; ZNF145; A2M; AAAS; ACADS; ACLS; ACVRL1; ALDH2; AMHR2; AOM; AQP2; ATD; ATP2A2; BDC; CIR; CD4; CDK4; CNA1; COL2A1; CYP27B1; DRPLA; ENUR2; FEOM1; FGF23; FPF; GNB3; GNS; HAL; HBP1; HMGA2; HMN2; HPD; IGF1; KCNA1; KERA; KRAS2; KRT1; KRT2A; KRT3; KRT4; KRT5; KRT6A; KRT6B; KRTHB6; LDHB; LYZ; MGCT; MPE; MVK; MYL2; OAP; PAH; PPKB; PRB3; PTPN11; PXR1; RLS; RSN; SAS; SAX1; SCA2; SCNN1A; SMAL; SPPM; SPSMA; TBX3; TBX5; TCF1; TPI1; TSC3; ULR; VDR; VWF; ATP7B; BRCA2; BRCD1; CLN5; CPB2; ED2; EDNRB; ENUR1; ERCC5; F10; F7; GJB2; GJB6; IPF1; MBS1; MCOR; NYS4; PCCA; RB1; RHOK; SCZD7; SCGC; SLC10A2; SLC25A15; STARP1; ZNF198; ACHM1; ARVD1; BCH; CTAA1; DAD1; DFNB5; EML1; GALC; GCH1; IBGC1; IGH@; IGHC group; IGHG1; IGHM; IGHR; IV; LTBP2; MJD; MNG1; MPD1; MPS3C; MYH6; MYH7; NP; NPC2; PABPN1; PSEN1; PYGL; RPGRIP1; SERPINA1; SERPINA3; SERPINA6; SLC7A7; SPG3A; SPTB; TCL1A; TGM1; TITF1; TMIP; TRA@; TSHR; USHLA; VP; ACCPN; AHO2; ANCR; B2M; BBS4; BLM; CAPN3; CDAN1; CDAN3; CLN6; CMH3; CYP19; CYP1A1; CYP1A2; DYX1; EPB42; ETFA; EYCL3; FAH; FBN1; FES; HCVS; HEXA; IVD; LCS1; LIPC; MYO5A; OCA2; OTSC1; PWCR; RLBP1; SLC12A1; SPG6; TPM1; UBE3A; WMS; ABCC6; ALDOA; APRT; ATP2A1; BBS2; CARD15; CATM; CDH1; CETP; CHST6; CLN3; CREBBP; CTH; CTM; CYBA; CYLD; DHS; DNASE1; DPEP1; ERCC4; FANCA; GALNS; GAN; HAGH; HBA1; HBA2; HBHR; HBQ1; HBZ; HBZP; HP; HSD11B2; IL4R; LIPB; MC1R; MEFV; MHC2TA; MLYCD; MMVP1; PHKB; PHKG2; PKD1; PKDTS; PMM2; PXE; SALL1; SCA4; SCNN1B; SCNN1G; SLC12A3; TAT; TSC2; VDI; WT3; ABR; ACACA; ACADVL; ACE; ALDH3A2; APOH; ASPA; AXIN2; BCL5; BHD; BLMH; BRCA1; CACD; CCA1; CCZS; CHRNB1; CHRNE; CMT1A; COL1A1; CORD5; CTNS; EPX; ERBB2; G6PC; GAA; GALK1; GCGR; GFAP; GH1; GH2; GP1BA; GPSC; GUCY2D; ITGA2B; ITGB3; ITGB4; KRT10; KRT12; KRT13; KRT14; KRT14L1; KRT14L2; KRT14L3; KRT16; KRT16L1; KRT16L2; KRT17; KRT9; MAPT; MDB; MDCR; MGI; MHS2; MKS1; MPO; MYO15A; NAGLU; NAPB; NF1; NME1; P4HB; PAFAH1B1; PECAM1; PEX12; PHB; PMP22; PRKAR1A; PRKCA; PRKWNK4; PRP8; PRPF8; PTLAH; RARA; RCV1; RMSA1; RP17; RSS; SCN4A; SERPINF2; SGCA; SGSH; SHBG; SLC2A4; SLC4A1; SLC6A4; SMCR; SOST; SOX9; SSTR2; SYM1; SYNS1; TCF2; THRA; TIMP2; TOC; TOP2A; TP53; TRIM37; VBCH; ATP8B1; BCL2; CNSN; CORD1; CYB5; DCC; F5F8D; FECH; FEO; LAMA3; LCFS2; MADH4; MAFD1; MC2R; MCL; MYP2; NPC1; SPPK; TGFBRE; TGIF; TTR; AD2; AMH; APOC2; APOE; ATHS; BAX; BCKDHA; BCL3; BFIC; C3; CACNA1A; CCO; CEACAM5; COMP; CRX; DBA; DDU; DFNA4; DLL3; DM1; DMWD; E11S; ELA2; EPOR; ERCC2; ETFB; EXT3; EYCL1; FTL; FUT1; FUT2; FUT6; GAMT; GCDH; GPI; GUSM; HB1; HCL1; HHC2; HHC3; ICAM3; INSR; JAK3; KLK3; LDLR; LHB; LIG1; LOH19CR1; LYL1; MAN2B1; MCOLN1; MDRV; MLLT1; NOTCH3; NPHS1; OFC3; OPA3; PEPD; PRPF31; PRTN3; PRX; PSG1; PVR; RYR1; SLC5A5; SLC7A9; STK11; TBXA2R; TGFB1; TNNI3; TYROBP; ADA; AHCY; AVP; CDAN2; CDPD1; CHED1; CHED2; CHRNA4; CST3; EDN3; EEGV1; FTLL1; GDF5; GNAS; GSS; HNF4A; JAG1; KCNQ2; MKKS; NBIA1; PCK1; PI3; PPCD; PPGB; PRNP; THBD; TOP1; AIRE; APP; CBS; COL6A1; COL6A2; CSTB; DCR; DSCR1; FPDMM; HLCS; HPE1; ITGB2; KCNE1; KNO; PRSS7; RUNX1; SOD1; TAM; ADSL; ARSA; BCR; CECR; CHEK2; COMT; CRYBB2; CSF2RB; CTHM; CYP2D6; CYP2D7P1; DGCR; DIA1; EWSR1; GGT1; MGCR; MN1; NAGA; NE2; OGS2; PDGFB; PPARA; PRODH; SCO2; SCZD4; SERPIND1; SLC5A1; SOX10; TCN2; TIMP3; TST; VCF; ABCD1; ACTL1; ADFN; AGMX2; AHDS; AIC; AIED; AIH3; ALAS2; AMCD; AMELX; ANOP1; AR; ARAF1; ARSC2; ARSE; ARTS; ARX; ASAT; ASSP5; ATP7A; ATRX; AVPR2; BFLS; BGN; BTK; BZX; C1HR; CACNA1F; CALB3; CBBM; CCT; CDR1; CFNS; CGF1; CHM; CHR39c; CIDX; CLA2; CLCN5; CLS; CMTX2; CMTX3; CND; COD1; COD2; COL4A5; COL4A6; CPX; CVD1; CYBB; DCX; DFN2; DFN4; DFN6; DHOF; DIAPH2; DKC1; DMD; DSS; DYT3; EBM; EBP; ED1; ELK1; EMD; EVR2; F8; F9; FCP1; FDPSL5; FGD1; FGS1; FMR1; FMR2; G6PD; GABRA3; GATA1; GDI1; GDXY; GJB1; GK; GLA; GPC3; GRPR; GTD; GUST; HMS1; HPRT1; HPT; HTC2; HTR2c; HYR; IDS; IGH1; IL2RG; INDX; IP1; IP2; JMS; KAL1; KFSD; L1CAM; LAMP2; MAA; MAFD2; MAOA; MAOB; MCF2; MCS; MEAX; MECP2; MF4; MGC1; MIC5; MID1; MLLT7; MLS; MRSD; MRX14; MRX1; MRX20; MRX2; MRX3; MRX40; MRXA; MSD; MTM1; MYCL2; MYP1; NDP; NHS; NPHL1; NROB1; NSX; NYS1; NYX; OA1; OASD; OCRL; ODT1; OFD1; OPA2; OPD1; OPEM; OPN1LW; OPN1MW; OTC; P3; PDHA1; PDR; PFC; PFKFB1; PGK1; PGK1P1; PGS; PHEX; PHKA1; PHKA2; PHP; PIGA;

PLP1; POF1; POLA; POU3F4; PPMX; PRD; PRPS1; PRPS2; PRS; RCCP2; RENBP; RENS1; RP2; RP6; RPGR; RPS4X; RPS6KA3; RS1; S11; SDYS; SEDL; SERPINA7; SH2D1A; SHFM2; SLC25A5; SMAX2; SRPX; SRS; STS; SYN1; SYP; TAF1; TAZ; TBX22; TDD; TFE3; THAS; THC; TIMM8A; TIM1; TKCR; TNFSF5; UBE1; UBE2A; WAS; WSN; WTS; WWS; XIC; XIST; XK; XM; XS; ZFX; ZIC3; ZNF261; ZNF41; ZNF6; AMELY; ASSP6; AZF1; AZF2; DAZ; GCY; RPS4Y; SMCY; ZFY; ABAT; AEZ; AFA; AFD1; ASAH1; ASD1; ASMT; CCAT; CECR9; CEPA; CLA3; CLN4; CSF2RA; CTS1; DF; DIH1; DWS; DYT2; DYT4; EBR3; ECT; EEF1A1L14; EYCL2; FANCB; GCSH; GCSL; GIP; GTS; HHG; HMI; HOAC; HOKPP2; HRPT1; HSD3B3; HTC1; HV1S; ICHQ; ICR1; ICR5; IL3RA; KAL2; KMS; KRT18; KSS; LCAT; LHON; LIMM; MANBB; MCPH2; MEB; MELAS; MIC2; MPFD; MS; MSS; MTATP6; MTCO1; MTC03; MTCYB; MTND1; MTND2; MTND4; MTND5; MTND6; MTRNR1; MTRNR2; MTTE; MTTG; MTTI; MTTK; MTTL1; MTTL2; MTTN; MTTP; MTTS1; NAMSD; OCD1; OPD2; PCK2; PCLD; PCOS1; PFKM; PKD3; PRCA1; PRO1; PROP1; RBS; RFXAP; RP; SHOX; SLC25A6; SPG5B; STO; SUOX; THM; and TTD.

12. The method of claim 1, wherein said method further comprises introducing the in vitro-synthesized RNA that comprises a modified nucleotide into a mammalian cell, wherein said functional protein is translated.

13. The method of claim 12, wherein said mammalian cell is an antigen-presenting cell, a dendritic cell, a macrophage, a neural cell, a brain cell, an astrocyte, a microglial cell, and a neuron, a spleen cell, a lymphoid cell, a lung cell, a lung epithelial cell, a skin cell, a keratinocyte, an endothelial cell, an alveolar cell, an alveolar macrophage, an alveolar pneumocyte, a vascular endothelial cell, a mesenchymal cell, an epithelial cell, a colonic epithelial cell, a hematopoietic cell, a bone marrow cell, a Claudius' cell, a Hensen cell, a Merkel cell, a Müller cell, a Paneth cell, a Purkinje cell, a Schwann cell, a Sertoli cell, an acidophil cell, an acinar cell, an adipoblast, an adipocyte, a brown or white alpha cell, an amacrine cell, a beta cell, a capsular cell, a cementocyte, a chief cell, a chondroblast, a chondrocyte, a chromaffin cell, a chromophobic cell, a corticotroph, a delta cell, a Langerhans cell, a follicular dendritic cell, an enterochromaffin cell, an ependymocyte, an epithelial cell, a basal cell, a squamous cell, an endothelial cell, a transitional cell, an erythroblast, an erythrocyte, a fibroblast, a fibrocyte, a follicular cell, a germ cell, a gamete, an ovum, a spermatozoon, an oocyte, a primary oocyte, a secondary oocyte, a spermatid, a spermatocyte, a primary spermatocyte, a secondary spermatocyte, a germinal epithelium, a giant cell, a glial cell, an astroblast, an astrocyte, an oligodendroblast, an oligodendrocyte, a glioblast, a goblet cell, a gonadotroph, a granulosa cell, a haemocytoblast, a hair cell, a hepatoblast, a hepatocyte, a hyalocyte, a interstitial cell, a juxtaglomerular cell, a keratinocyte, a keratocyte, a lemmal cell, a leukocyte, a granulocyte, a basophil, an eosinophil, a neutrophil, a lymphoblast, a B-lymphoblast, a T-lymphoblast, a lymphocyte, a B-lymphocyte, a T-lymphocyte, a helper induced T-lymphocyte, a Th1 T-lymphocyte, a Th2 T-lymphocyte, a natural killer cell, a thymocyte, a Kupffer cell, an alveolar macrophage, a foam cell, a histiocyte, a luteal cell, a lymphocytic stem cell, a lymphoid cell, a lymphoid stem cell, a macroglial cell, a mammotroph, a mast cell, a medulloblast, a megakaryoblast, a megakaryocyte, a melanoblast, a melanocyte, a mesangial cell, a mesothelial cell, a metamyelocyte, a monoblast, a monocyte, a mucous neck cell, a myoblast, a muscle cell, a cardiac muscle cell, a skeletal muscle cell, a smooth muscle cell, a myelocyte, a myeloid cell, a myeloid stem cell, a myoblast, a myoepithelial cell, a myofibrobast, a neuroblast, a neuroepithelial cell, a neuron, an odontoblast, an osteoblast, an osteoclast, an osteocyte, an oxyntic cell, a parafollicular cell, a paraluteal cell, a peptic cell, a pericyte, a peripheral blood mononuclear cell, a phaeochromocyte, a phalangeal cell, a pinealocyte, a pituicyte, a plasma cell, a platelet, a podocyte, a proerythroblast, a promonocyte, a promyeloblast, a promyelocyte, a pronormoblast, a reticulocyte, a retinal pigment epithelial cell, a retinoblast, a small cell, a somatotroph, a stem cell, a sustentacular cell, a teloglial cell, and a zymogenic cell.

14. The method of claim 1, wherein said protein encoded by said in vitro-synthesized RNA that exhibits reduced immunogenicity is a recombinant protein of interest.

15. The method of claim 1, wherein said method further comprises increasing the number, percentage, or frequency of modified nucleotides containing one or more of said modified nucleosides replaced in said in vitro-synthesized RNA in order to further decrease immunogenicity.

* * * * *

UNITED STATES PATENT AND TRADEMARK OFFICE
CERTIFICATE OF CORRECTION

PATENT NO. : 10,232,055 B2
APPLICATION NO. : 15/339363
DATED : March 19, 2019
INVENTOR(S) : Katalin Kariko et al.

Page 1 of 1

It is certified that error appears in the above-identified patent and that said Letters Patent is hereby corrected as shown below:

In the Specification

Please replace Column 1, Lines 23-29 as follows:
-- STATEMENT REGARDING FEDERALLY SPONSORED RESEARCH OR DEVELOPMENT
This invention was made with government support under AI060505, AI050484, DE014825 and HL087688 awarded by the National Institutes of Health. The government has certain rights in the invention. --

Signed and Sealed this
Twenty-ninth Day of December, 2020

Andrei Iancu
*Director of the United States Patent and Trademark Office*